United States Patent
Virgin, IV et al.

(10) Patent No.: US 10,357,556 B2
(45) Date of Patent: Jul. 23, 2019

(54) METHODS AND COMPOSITIONS FOR T CELL GENERATION AND USES THEREOF

(71) Applicants: Herbert W. Virgin, IV, St. Louis, MO (US); Hiutung Chu, Pasadena, CA (US); Sarkis K. Mazmanian, Pasadena, CA (US)

(72) Inventors: Herbert W. Virgin, IV, St. Louis, MO (US); Hiutung Chu, Pasadena, CA (US); Sarkis K. Mazmanian, Pasadena, CA (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/430,800

(22) Filed: Feb. 13, 2017

(65) Prior Publication Data

US 2017/0232092 A1 Aug. 17, 2017

Related U.S. Application Data

(60) Provisional application No. 62/294,823, filed on Feb. 12, 2016.

(51) Int. Cl.
| | |
|---|---|
| A61K 39/00 | (2006.01) |
| C12N 5/0783 | (2010.01) |
| A61K 35/12 | (2015.01) |
| A61K 39/07 | (2006.01) |
| C12Q 1/6883 | (2018.01) |
| G01N 33/50 | (2006.01) |

(52) U.S. Cl.
CPC ............ *A61K 39/07* (2013.01); *A61K 35/12* (2013.01); *A61K 39/0008* (2013.01); *C12N 5/0637* (2013.01); *C12Q 1/6883* (2013.01); *G01N 33/5047* (2013.01); *C12Q 2600/118* (2013.01); *C12Q 2600/136* (2013.01); *C12Q 2600/156* (2013.01); *G01N 2333/54* (2013.01)

(58) Field of Classification Search
None
See application file for complete search history.

(56) References Cited

PUBLICATIONS

Shen et al. Cell Host Microbe. Oct. 18, 2012; 12(4):509-520.*
Murthy et al. Nature. Feb. 27, 2014; 506(7489):456-462.*
Lozano et al. J Immunol; 195:3180-3189 published online Aug. 2015.*
Allan et al. (2008) CD4+ T-regulatory cells: Toward therapy for human diseases, Immunological Reviews, 223(1), pp. 391-421.
Belkaid, Hand (2014) Role of the microbiota in immunity and inflammation, Cell, 157(1), pp. 121-141.
Brant (2011) Update on the heritability of inflammatory bowel disease: The importance of twin studies, Inflammatory Bowel Diseases, 17(1), pp. 1-5.
Brown, Sadarangani, Finlay (2013) The role of the immune system in governing host-microbe interactions in the intestine, Nature immunology, 14(7), pp. 660-667.
Cadwell et al. (2010) Virus-Plus-Susceptibility Gene Interaction Determines Crohn's Disease Gene Atg16L1 Phenotypes in Intestine, Cell, 141(7), pp. 1135-1145.
Consortium (2007) Genome-wide association study of 14 000 cases of seven common diseases and 3 000 shared controls, Nature, 447(7145), pp. 661-678.
Cooney et al. (2010) NOD2 stimulation induces autophagy in dendritic cells influencing bacterial handling and antigen presentation, Nature medicine, 16(1), pp. 90-97.
Coyne et al. (2001) Polysaccharide Biosynthesis Locus Required for Virulence of Bacteroides fragilis Polysaccharide Biosynthesis Locus Required for Virulence of Bacteroides fragilis, Infection and Immunity, 69(7), pp. 4342-4350.
Gardet, Xavier (2012) Common alleles that influence autophagy and the risk for inflammatory bowel disease, Current Opinion in Immunology, 24(5), pp. 522-529.
Halfvarson et al. (2003) Inflammatory bowel disease in a Swedish twin cohort: A long-term follow-up of concordance and clinical characteristics, Gastroenterology, 124(7), pp. 1767-1773.
Hampe et al. (2007) A genome-wide association scan of nonsynonymous SNPs identifies a susceptibility variant for Crohn disease in ATG16L1, Nature genetics, 39(2), pp. 207-211.
Hill, Artis (2010) Intestinal Bacteria and the Regulation of Immune Cell Homeostasis, Annu. Rev. Immunol, 28, pp. 623-667.
Honda, Littman (2012) The microbiome in infectious disease and inflammation, Annu Rev Immunol, 30, pp. 759-795.
Hooper, Littman, MacPherson (2012) Interactions Between the Microbiota and the Immune System, Science, 336(6086), pp. 1268-1273.
Hubbard-Lucey et al. (2014) Autophagy Gene Atg16l1 Prevents Lethal T Cell Alloreactivity Mediated by Dendritic Cells, Immunity, 41(4), pp. 579-591.
Hugot et al. (2001) Association of NOD2 leucine-rich repeat variants with susceptibility to Crohn's disease, Nature, 411(6837), pp. 599-603.
Hwang et al. (2012) Nondegradative role of Atg5-Atg12/Atg16L1 autophagy protein complex in antiviral activity of interferon gamma, Cell Host and Microbe, 11(4), pp. 397-409.
Jostins et al. (2012) Host-microbe interactions have shaped the genetic architecture of Inflammatory Bowel Disease, Nature 491(7422), pp. 119-124.
Kabat et al. (2016) The autophagy gene Atg16l1 differentially regulates Treg and TH2 cells to control intestinal inflammation, eLife, 5(Feb. 2016), pp. 1-27.
Kimmey et al. (2015) Unique role for ATG5 in PMN-mediated immunopathology during M. tuberculosis infection, Nature, 528(7583), pp. 565-569.
Kobayashi et al. (2005) Nod2-dependent regulation of innate and adaptive immunity in the intestinal tract, Science, 307(5710), pp. 731-734.

(Continued)

*Primary Examiner* — Oluwatosin A Ogunbiyi

(57) ABSTRACT

Among the various aspects of the present disclosure is the provision of a method of treating an inflammatory bowel disease. Another aspect provides the provision of a screening method for therapeutic agents. Another aspect provides a method of detecting $T_{reg}$ cells to determine if a subject has an inflammatory disease. The present disclosure provides for methods of treatment, diagnosis, and screening for drugs for colitis and ileitis.

14 Claims, 51 Drawing Sheets

(56) References Cited

PUBLICATIONS

Kundu et al. (2008) Ulk1 plays a critical role in the autophagic clearance of mitochondria and ribosomes during reticulocyte maturation, Blood, 112(4), pp. 1493-1502.
Kurtz et al. (2014) Extracellular adenosine regulates colitis through effects on lymphoid and nonlymphoid cells, Am J Physiol Gastrointest Liver Physiol, 307(3), pp. G338-G346.
Lassen et al. (2014) Atg16L1 T300A variant decreases selective autophagy resulting in altered cytokine signaling and decreased antibacterial defense, Proceedings of the National Academy of Sciences of the United States of America, 111(21), pp. 7741-7746.
Lu et al. (2016) Homeostatic Control of Innate Lung Inflammation by Vici Syndrome Gene Epg5 and Additional Autophagy Genes Promotes Influenza Pathogenesis, Cell Host and Microbe, 19(1), pp. 102-113.
Martinez et al. (2015) Molecular characterization of LC3-associated phagocytosis reveals distinct roles for Rubicon, NOX2 and autophagy proteins, Nature cell biology, 17(7), pp. 893-906.
Matsunaga et al. (2009) Two Beclin 1-binding proteins, Atg14L and Rubicon, reciprocally regulate autophagy at different stages, Nature cell biology, 11(4), pp. 385-396.
Mazmanian, Round, Kasper (2008) A microbial symbiosis factor prevents intestinal inflammatory disease, Nature, 453(7195), pp. 620-625.
Molodecky et al. (2012) Increasing incidence and prevalence of the inflammatory bowel diseases with time, based on systematic review, Gastroenterology, 142(1), pp. 46-54.e42.
Murthy et al. (2014) A Crohn/'s disease variant in Atg16l1 enhances its degradation by caspase 3, Nature, 506(7489), pp. 456-462.
Ogura et al. (2001) A frameshift mutation in NOD2 associated with susceptibility to Crohn's disease, Nature, 411(6837), pp. 603-606.
Orholm et al. (2000) Concordance of inflammatory bowel disease among Danish twins. Results of a nationwide study, Scand J Gastroenterol, 35(10), pp. 1075-1081.
Packey, Sartor (2009) Commensal Bacteria, Traditional an Opportunistic Pathogens, Dysbiosis and Bacterial Killing in Inflammatory Bowel Diseases, Current Opinions in Infectious Diseases, 22(3), pp. 292-301.
Park et al. (2016) Autophagy Genes Enhance Murine Gammaherpesvirus 68 Reactivation From Latency by Preventing Virus-induced Systemic Inflammation, Cell Host and Microbe, 19(1), pp. 91-101.
Parkes et al. (2007) Sequence variants in the autophagy gene IRGM and multiple other replicating loci contribute to Crohn's disease susceptibility, Nature genetics, 39(7), pp. 830-832.
Patrick, Reid (1983) Separation of capsulate and non-capsulate Bacteroides Fragilis on a discontinuous density gradient, Journal of Medical Microbiology, 16, pp. 239-241.
Peterson et al. (2008) Metagenomic Approaches for Defining the Pathogenesis of Inflammatory Bowel Diseases, Cell Host Microbe, 3(6), pp. 417-427.
Rioux et al. (2007) Genome-wide association study identifies new susceptibility loci for Crohn disease and implicates autophagy in disease pathogenesis, Nat Genet, 39(5), pp. 596-604.
Round, Mazmanian (2009) The gut microbiota shapes intestinal immune responses during health and disease, Nature Reviews Immunology, 9(5), pp. 313-323.
Round et al. (2011) The Toll-Like Receptor 2 Pathway Establishes Colonization by a Commensal of the Human Microbiota, Science, 332(6032), pp. 974-977.
Round, Mazmanian (2010) Inducible Foxp3+ regulatory T-cell development by a commensal bacterium of the intestinal microbiota, Proceedings of the National Academy of Sciences of the United States of America, 107(27), pp. 12204-12209.
Saitoh et al. (2008) Loss of the autophagy protein Atg16L1 enhances endotoxin-induced IL-1 beta production, Nature, 456(7219), pp. 264-U68.
Sanjuan et al. (2007) Toll-like receptor signalling in macrophages links the autophagy pathway to phagocytosis, Nature, 450(7173), pp. 1253-1257.
Shen et al. (2012) Outer membrane vesicles of a human commensal mediate immune regulation and disease protection, Cell Host and Microbe, 12(4), pp. 509-520.
Travassos, Carneiro, Ramjeet (2010) Nod1 and Nod2 direct autophagy by recruiting ATG16L1 to the plasma membrane at the site of bacterial entry, Nature Immunology, 11(1), pp. 55-63.
Tysk et al. (1988) Ulcerative colitis and Crohn's disease in an unselected population of monozygotic and dizygotic twins. A study of heritability and the influence of smoking, Gut, 29(7), pp. 990-996.
Wei et al. (2016) Autophagy enforces functional integrity of regulatory T cells by coupling environmental cues and metabolic homeostasis, Nature immunology, 17(3), pp. 277-286.
Wlodarska, Kostic, Xavier (2015) An integrative view of microbiome-host interactions in inflammatory bowel diseases, Cell Host and Microbe, 17(5), pp. 577-591.

* cited by examiner

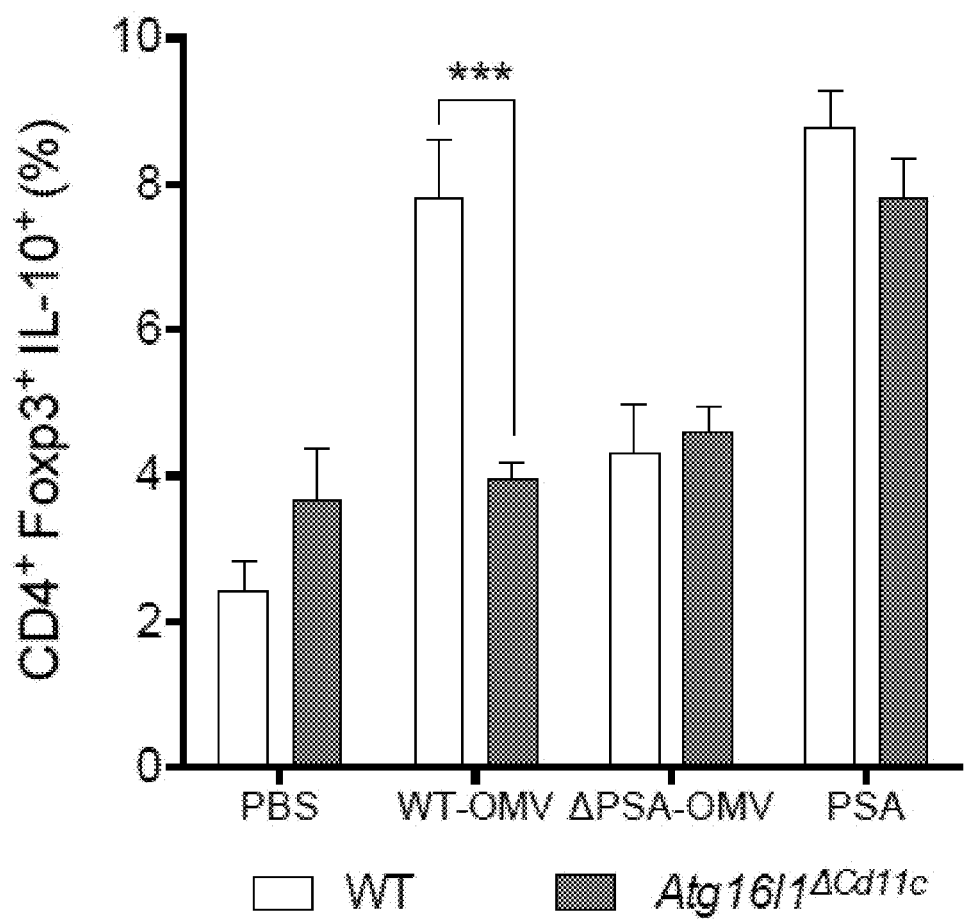

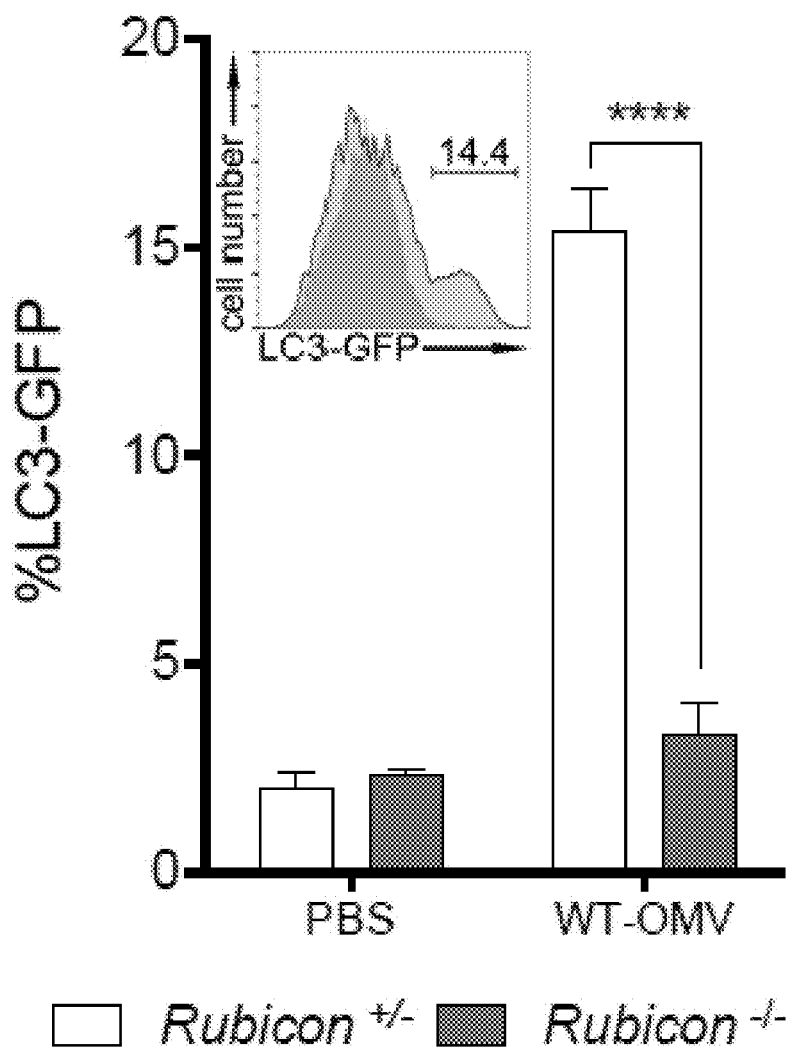

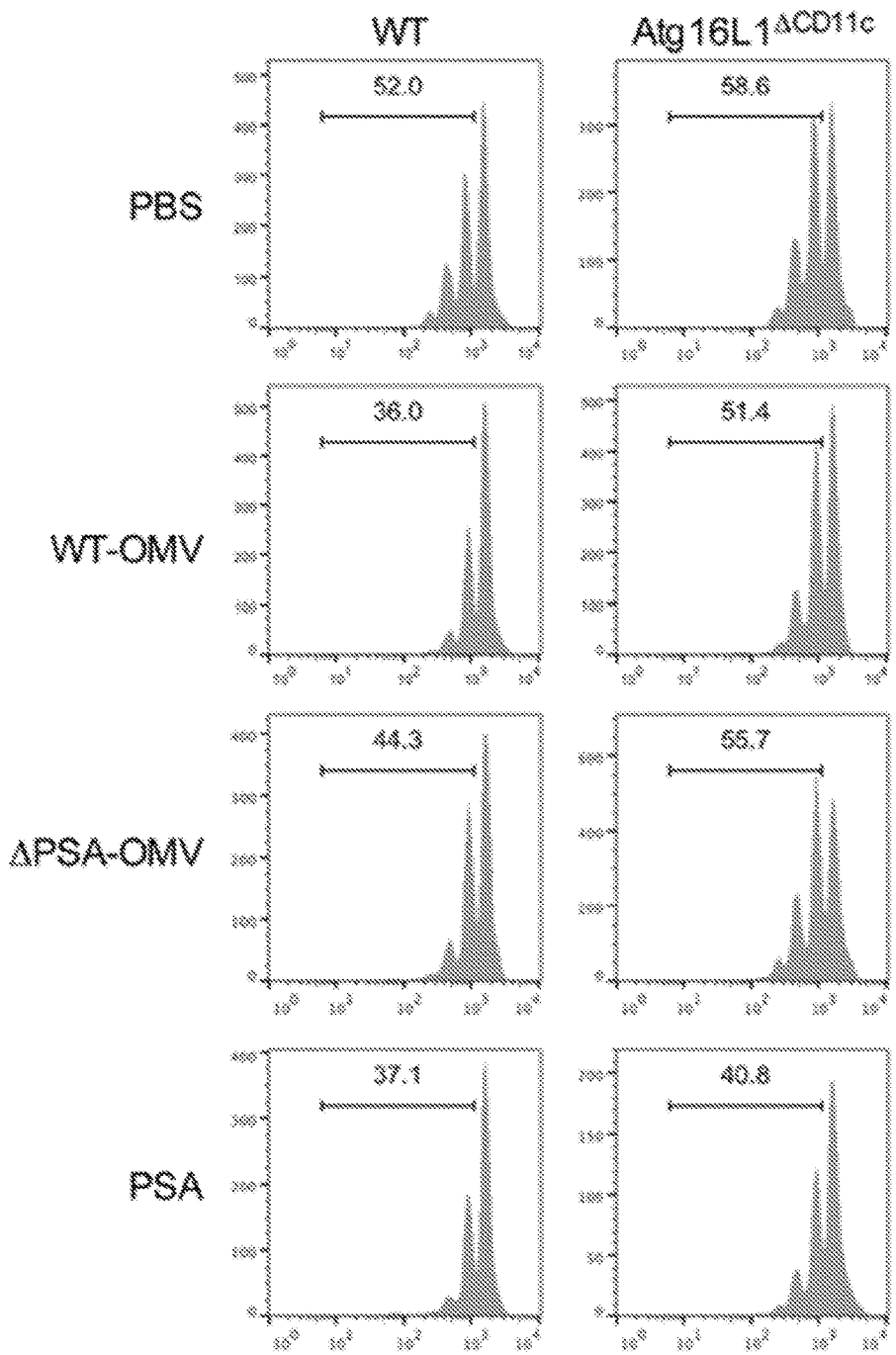

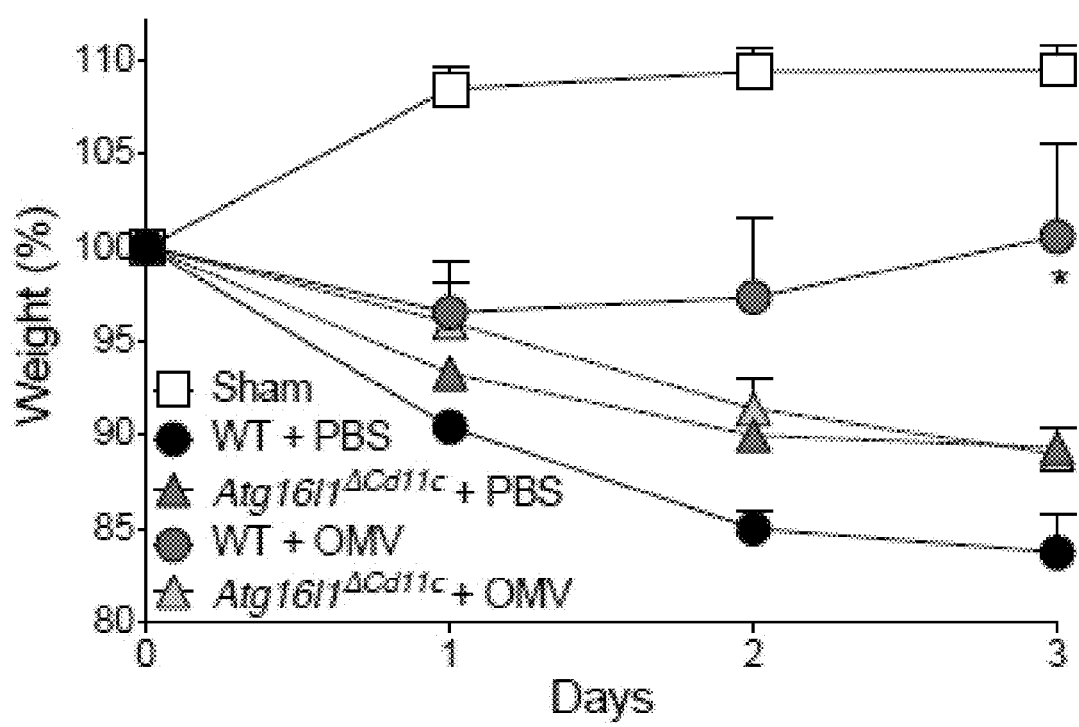

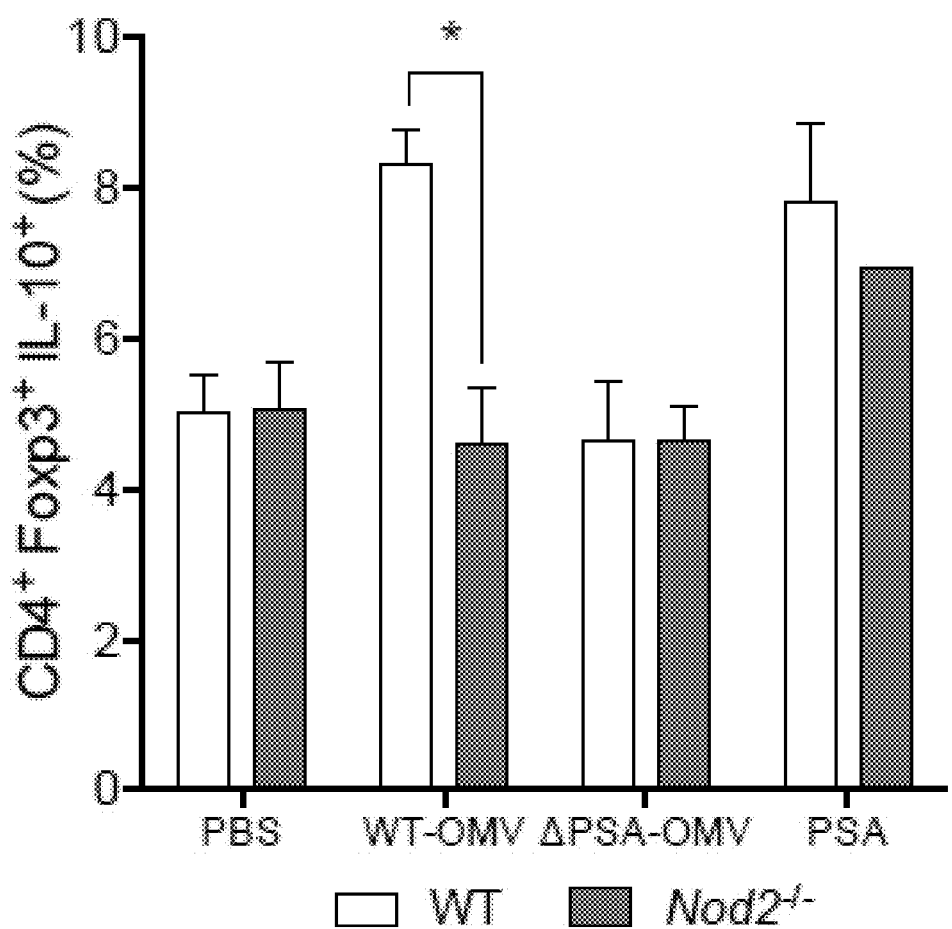

METHODS AND COMPOSITIONS FOR T CELL GENERATION AND USES THEREOF

CROSS-REFERENCE TO RELATED APPLICATIONS

This application claims priority from U.S. Provisional Application Ser. No. 62/294,823 filed on 12 Feb. 2016, which is incorporated herein by reference in its entirety.

STATEMENT REGARDING FEDERALLY SPONSORED RESEARCH OR DEVELOPMENT

This invention was made with government support under grant numbers DK078938, AI109725, GM099535, and DK100109 awarded by National Institutes of Health. The government has certain rights in the invention.

MATERIAL INCORPORATED-BY-REFERENCE

Not Applicable.

FIELD OF THE INVENTION

The present disclosure generally relates to methods and treating and methods of diagnosing colitis, ileitis, and inflammatory disease and screening methods for compositions for treatment thereof.

BACKGROUND OF THE INVENTION

IBD impacts over 1.5 million people in the US, with rates of diagnosis increasing and treatment options remaining limited. The etiology of IBD is complex and incompletely resolved.

Intestinal microbiota can modulate development and function of the immune system, and play a critical role in inflammatory bowel disease (IBD), a family of idiopathic intestinal disorders including Crohn's disease (CD), ulcerative colitis (UC), and ileitis. Concordance rates of 40-50% between monozygotic twins implicate gene-environment interactions contribute to CD, albeit in ways that are currently poorly understood.

Advances in DNA sequencing technologies can provide insights into the human genome and the gut microbiome in IBD, enabling detailed genomic characterization of patients and chronicling alterations in the composition and gene content of the gut microbiome (dysbiosis).

SUMMARY OF THE INVENTION

Among the various aspects of the present disclosure is the provision of a method of treating colitis, ileitis, or an inflammatory bowel disease. Another aspect provides the provision of a screening method for therapeutic agents for colitis, ileitis, or an inflammatory bowel disease. Another aspect provides a method of detecting $T_{reg}$ cells to determine if a subject has colitis, ileitis, or an inflammatory bowel disease.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A-FIG. 1F is a series of bar graphs, flow cytometry plots showing ATG16L1 signals via a non-canonical autophagy pathway during OMV-mediated $T_{reg}$ induction. (FIG. 1A) ELISA for IL-10 production during DC-T cell co-cultures with WT or Atg16L1$^{\Delta CD11c}$ BMDCs treated with PBS, B. fragilis WT-OMV, ΔPSA-OMV or purified PSA. (FIG. 1B and FIG. 1C) Representative flow cytometry plots (FIG. 1B) and frequency (FIG. 1C) of CD4$^+$Foxp3$^+$IL-10$^+$ $T_{regs}$ from DC-T cell co-cultures with WT or Atg16L1$^{\Delta CD11c}$ DCs treated with PBS, B. fragilis WT-OMV, ΔPSA-OMV or purified PSA. (FIG. 1D) T cell suppression assay analyzing in vitro generated $T_{regs}$ from WT or Atg16L1$^{\Delta CD11c}$ DCs treated with WT-OMVs. (FIG. 1E) Quantification of LC3-GFP accumulation by B. fragilis WT-OMV treatment of Rubicon$^{+/-}$ or Rubicon$^{-/-}$ DCs. Representative flow cytometry histogram plot (inset). PBS, grey; WT-OMV, blue. (FIG. 1F) Frequency of CD4$^+$Foxp3$^+$IL-10$^+$ $T_{regs}$ from Rubicon$^{+/-}$ or Rubicon$^{-/-}$ DC-T cell co-cultures treated with PBS, B. fragilis WT-OMV, ΔPSA-OMV or purified PSA. Error bars represent S.E.M. * $p<0.05$, * $p<0.001$, ** $p<0.0001$. Two-way ANOVA, followed by Tukey's post-hoc analysis. Data are representative of at least 2 independent experiments.

FIG. 2 shows vehicle treatment of WT and Atg16L1$^{\Delta CD11c}$ DCs does not induce significant production of IL-10 among CD4$^+$Foxp3$^+$ $T_{regs}$.

FIG. 3A-FIG. 3C is a series of histograms and line and scatter plots showing purified PSA does not require ATG16L1 to promote suppressive $T_{reg}$ activity. (FIG. 3A) Representative histograms measuring suppression of responder T cell proliferation by in vitro generated $T_{regs}$ from WT or Atg16L1$^{\Delta CD11c}$ DCs treated with PBS, B. fragilis WT-OMV, ΔPSA-OMV or purified PSA. (FIG. 3B and FIG. 3C) T cell suppression index of in vitro generated $T_{regs}$ from WT or Atg16L1$^{\Delta CD11c}$ DCs treated with (FIG. 3B) ΔPSA-OMV or (FIG. 3C) purified PSA at various $T_{reg}$:$T_{eff}$ ratios. Cell proliferation was stimulated with αCD3. Error bars represent S.E.M. * $p<0.05$. Data are representative of at least 2 independent experiments.

FIG. 9A-FIG. 9E is a series of graphs and histology images showing B. fragilis OMVs require ATG16L1 in CD11c$^+$ DCs for protection from colitis. (FIG. 9A and FIG. 9B) Weight loss (FIG. 9A), colon length and gross pathology (FIG. 9B) of WT and Atg16L1$^{ΔCD11c}$ mice orally treated with PBS or B. fragilis WT-OMV during DNBS colitis. Sham groups were treated with ethanol. (FIG. 9C) Colitis scores by a blinded pathologist using a standard scoring system, and representative H & E images. Scale bar represents 100 μm. (FIG. 9D and FIG. 9E) Mesenteric lymph node (MLN) lymphocytes isolated post-DNBS analyzed for IL-10 (FIG. 9D) and IL-17A (FIG. 9E) production among CD4$^+$Foxp3$^+$ T$_{regs}$, as assessed by flow cytometry. Error bars represent S.E.M. * p<0.05, * p<0.001, ** p<0.0001. Two-way ANOVA, followed by Tukey's post-hoc analysis. Data are representative of at least 3 independent experiments, with 3-9 mice/group.

(FIG. 10A) Survival cure of WT and Atg16L1$^{ΔCD11c}$ mice orally treated with PBS or B. fragilis WT-OMV during DNBS colitis. Data are representative of at least 6 independent experiments, with 4-10 mice/group. * p<0.05, Gehan-Breslow-Wilcoxon test. (FIG. 10B) MLNs isolated post-DNBS analyzed for Il10/Il12 transcripts, as assessed by quantitative real-time RT-PCR. Transcripts were normalized to β-actin. (FIG. 10C) cLP lymphocytes isolated post-DNBS analyzed for IL-10 production among CD4$^+$ Foxp3$^+$ T$_{regs}$. Error bars represent S.E.M. * p<0.05. Data are representative of at least 2 independent experiments, with 3-5 mice/group.

(FIG. 13A) MLN and (FIG. 13B) cLP lymphocytes isolated post-DNBS analyzed for IFN-γ production among CD4$^+$ T cells, as assessed by flow cytometry. Error bars represent S.E.M. ns, not significant. Data are representative of at least 2 independent experiments, with 3-4 mice/group.

(FIG. 16A) WT and Atg16L1$^{ΔCD11c}$ BMDCs were pulsed with WT-OMVs at indicated time points and analyzed for uptake of WT-OMVs. Treated DCs were analyzed by western blot and probed for PSA and β-actin. Δ, Atg16L1$^{ΔCD11c}$ DCs. Data are representative of at least 4 independent experiments. (FIG. 16B) WT and Atg16L1$^{ΔCD11c}$ BMDCs were pulsed with Click-iT-labeled-Alexa Fluor 647 WT- or ΔPSA-OMV for 3 h and analyzed for uptake of OMVs among live CD11c$^+$MHCII$^+$ cells. Data are representative of at least 2 independent experiments. (FIG. 16C to FIG. 16E) Representative histograms of MHC II (FIG. 16C), CD80 (FIG. 16D) and CD86 (FIG. 16E) expression among live, CD11c$^+$ cells upon PBS and WT-OMV treatment of WT or Atg16L1$^{ΔCD11c}$ BMDCs. Data are representative of at least 4 independent experiments.

FIG. 18A-FIG. 18D is a series of flow cytometry plots, bar graphs, line and scatter plots, and images showing NOD2 is required for OMV-mediated T$_{regs}$ induction and protection from colitis. (FIG. 18A and FIG. 18B) Representative flow cytometry plots (FIG. 18A) from WT-OMV (left) and ΔPSA-OMV (right) treated BMDCs co-cultured with CD4$^+$ T cells, and frequency (FIG. 18B) of CD4$^+$Foxp3$^+$ IL-10$^+$ T$_{regs}$ from DC-T cell co-cultures. (FIG. 18C and FIG. 18D) Weight loss (FIG. 18C), colon length and gross pathology (FIG. 18D) of WT or Nod2$^{-/-}$ mice treated with PBS or B. fragilis WT-OMV during DNBS colitis. Error bars represent S.E.M. * p<0.05, **** p<0.0001. Two-way ANOVA, followed by Tukey's post-hoc analysis. Data are representative of at least 3 independent experiments, with 3-5 mice/group.

(FIG. 19A) cLP lymphocytes isolated post-DNBS analyzed for IL-10 production among CD4$^+$Foxp3$^+$T$_{regs}$. (FIG. 19B) Proportions of CD4$^+$ Foxp3$^+$ T$_{regs}$ in MLNs of WT and Nod2$^{-/-}$ mice orally treated with PBS or *B. fragilis* WT-OMV during DNBS colitis. Error bars represent S.E.M. ** $p<0.01$. ns, not significant. Data are representative of at least 2 independent experiments, with 4-5 mice/group.

(FIG. 21A) Frequency of IL-10 among CD4$^+$Foxp3$^+$ T$_{regs}$ from DC-T cell co-cultures of WT and T300A BMDCs treated with PBS, *B. fragilis* WT-OMV, ΔPSA-OMV or purified PSA. (FIG. 21B) Weight loss and gross pathology, (FIG. 21C) colon length, (FIG. 21D) H & E sections, (FIG. 21E) and colitis scores of WT and T300A mice orally treated with PBS or *B. fragilis* WT-OMV during DNBS colitis. MLN lymphocytes isolated post-DNBS analyzed for (FIG. 21F) IL-10 and (FIG. 21G) IL-17A production among CD4$^+$Foxp3$^+$T$_{regs}$, as assessed by flow cytometry. Error bars represent S.E.M. * $p<0.05$,  $p<0.01$, ** $p<0.0001$. Data are representative of at least 3 independent experiments, with 3-5 mice/group.

(FIG. 22A and FIG. 22B) MoDCs with either the protective (FIG. 22A) or risk (FIG. 22B) allele were treated with PBS, *B. fragilis* WT-OMV, APSA-OMV or purified PSA, washed and co-cultured with syngeneic CD4$^+$ T cells. IL-10 expression was analyzed by flow cytometry among CD4$^+$Foxp3$^+$ T$_{regs}$. Human samples were processed and analyzed in a blinded fashion. CTL, control subjects; CD, Crohn's Disease subjects. Error bars represent S.E.M. * $p<0.05$,  $p<0.01$, * $p<0.001$, **** $p<0.0001$, ns, not significant. One-way ANOVA, followed by Tukey's post-hoc analysis.

DETAILED DESCRIPTION OF THE INVENTION

Figure 1A:
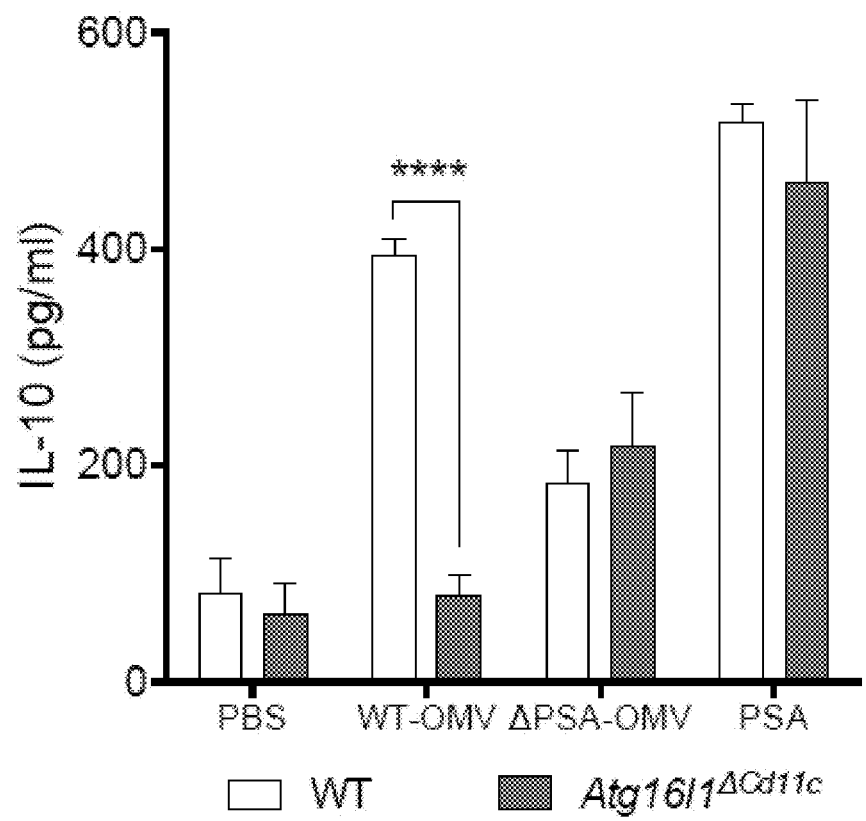
Figure 1B:
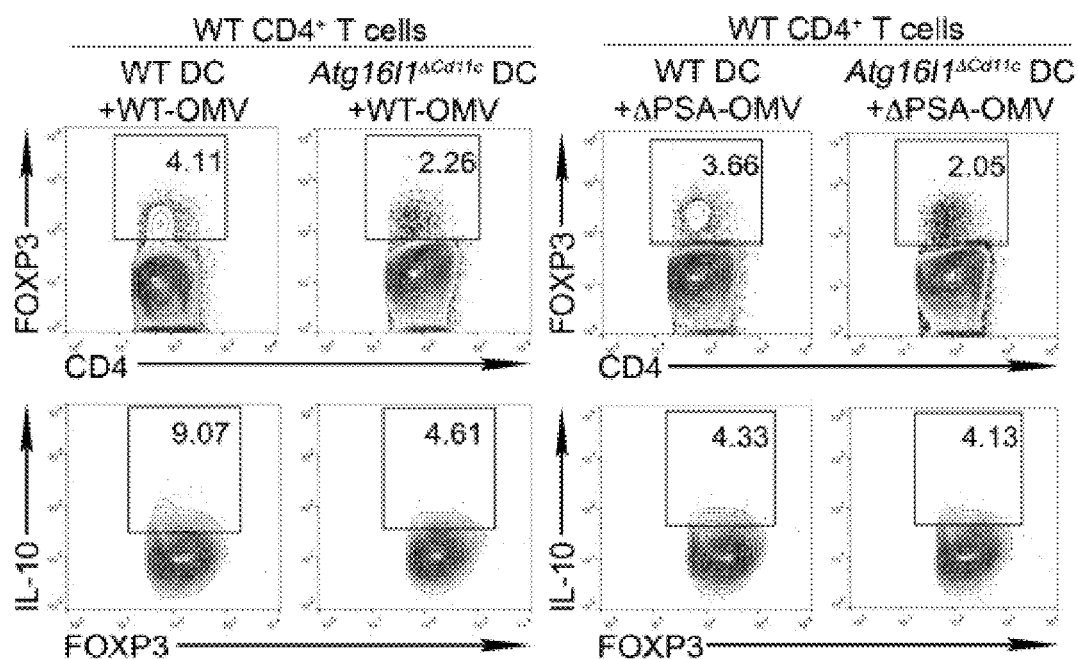

The present disclosure is based, at least in part, on the discovery that mouse and human DCs require functional ATG16L1 for induction of CD4$^+$Foxp3$^+$IL-10$^+$Tregs in response to *B. fragilis* OMVs. *Bacteroides fragilis* utilizes IBD-associated genes to promote mucosal tolerance. As shown herein, OMVs require IBD-associated genes, ATG16L1 and NOD2, to activate a non-canonical autophagy pathway during protection from colitis or ileitis. In addition to Atg16, Atg5 and Atg7 are required for the generation of Tregs. As shown herein, ATG16L1-deficient dendritic cells were shown not to induce regulatory T cells (T$_{reg}$) to suppress mucosal inflammation. As also shown herein, immune cells from human subjects with a major risk variant in ATG16L1 are defective in T$_{reg}$ responses to OMVs. As such, it has been shown that defects in ATG16L1 and NOD2 reduce protection from colitis or ileitis. Also, RUBICON was shown as a novel diagnostic tool for colitis or ileitis. As such, the present disclosure provides for methods of treatment, diagnosis, and screening for drugs for colitis or ileitis.

It is presently thought that inflammatory bowel disease (IBD) is associated with risk variants in the human genome and dysbiosis of the gut microbiome, though unifying principles for these findings remain largely undescribed. As described herein, the human commensal *Bacteroides* fragilis delivers immunomodulatory molecules to immune cells via secretion of outer membrane vesicles (OMVs).

As described herein, polymorphisms in susceptibility genes were shown to promote disease through defects in 'sensing' protective signals from the microbiome, defining a potentially critical gene-environment etiology for IBD.

Close to 200 risk loci have been proposed for CD, with several susceptibility genes linked to the regulation of autophagy (e.g., ATG16L1) or to microbial sensors that activate autophagy (e.g., NOD2). While previous studies have shown that disruption of ATG16L1 and NOD2 impacts CD susceptibility through defects in microbial clearance, recent reports reveal that immune cells impaired in autophagy are hyper-inflammatory.

It is currently believed that deficiencies in ATG16L1 or NOD2 may contribute to CD risk through impaired anti-inflammatory responses, a hypothesis that may not be mutually exclusive with microbial clearance functions.

Inflammatory Diseases, Disorders, or Conditions

Methods as described herein can treat inflammatory diseases, disorders, or conditions. Inflammatory diseases, disorders, or conditions can be any disease, disorder or condition, or symptoms thereof, associated with inflammation where the subject exhibits a diminished capacity to generate Treg cells.

In some embodiments, the inflammatory disease, disorder, or condition affects the small intestine or colon. For example, ATG16L1T300A provides risk for Crohn's disease. As another example, the inflammatory disease, disorder, or condition can include inflammation of both (or either of) the colon (e.g., ulcerative colitis), the ileum also called ileitis, or Crohn's disease. As such, the methods as described herein are of impact to methods of treatment, diagnosis, and screening for drugs for colitis and ileitis.

In some embodiments, inflammatory diseases, disorders, or conditions can be colitis, ileitis, inflammatory bowel disease, Crohn's disease, ulcerative colitis, ischemic colitis, colitis from allergic reactions, or microscopic colitis.

In some embodiments, methods as described herein can treat abdominal pain, cramping, or diarrhea, with or without blood in the stool associated with colitis or ileitis.

In some embodiments, methods as described herein can treat fever, chills, fatigue, dehydration, eye inflammation, joint swelling, canker sores, or skin inflammation associated with colitis.

Colitis and ileitis can refer to inflammation of the inner lining of the colon or the ileum, respectively.

Causes of colitis or ileitis can include infection, inflammatory bowel disease (e.g., Crohn's disease, ulcerative colitis), ischemic colitis, allergic reactions, or microscopic colitis.

Symptoms of colitis or ileitis can depend upon the cause and may include abdominal pain, cramping, or diarrhea, with or without blood in the stool (one of the hallmark symptoms of colitis).

Associated symptoms depend upon the cause of colitis or ileitis and may include fever, chills, fatigue, dehydration, eye inflammation, joint swelling, canker sores, or skin inflammation.

The cause of colitis or ileitis can be found by tests including blood tests (complete blood count, electrolytes, kidney function, or inflammatory marker tests), urine or stool samples, colonoscopy (including colonoscopy with biopsy of the ileum), or barium enema.

Conventional treatment of colitis or ileitis can depend upon the cause, and often is focused on symptom relief, supportive care, and maintaining adequate hydration and pain control. Antibiotics may be prescribed to treat infectious causes of colitis or ileitis. Some bacterial infections that cause colitis or ileitis resolve without any antibiotic treatment.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains.

Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6(\log_{10}[Na^+])+0.41$(fraction G/C content)$-0.63$(% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The $T_{reg}$ generating agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Regulatory T Cells ($T_{reg}$)

The regulatory T cells (Tregs), also previously known as suppressor T cells, are a subpopulation of T cells which modulate the immune system, maintain tolerance to self-antigens, and prevent autoimmune disease. Tregs are immunosuppressive and generally suppress or downregulate induction and proliferation of effector T cells. Tregs express the biomarkers CD4, FOXP3, and CD25 and are thought to be derived from the same lineage as naïve CD4 cells.

Because effector T cells also express CD4 and CD25, Tregs are very difficult to effectively discern from effector CD4+, making them difficult to study. Recent research has found that the cytokine TGFβ is essential for Tregs to differentiate from naïve CD4+ cells and is important in maintaining Treg homeostasis.

Mouse models have suggested that modulation of Tregs can treat autoimmune disease and cancer and can facilitate organ transplantation. Their implications for cancer are complicated. Tregs tend to be upregulated in individuals with cancer, and they seem to be recruited to the site of many tumors. Studies in both humans and animal models have implicated that high numbers of Tregs in the tumor microenvironment is indicative of a poor prognosis, and Tregs are thought to suppress tumor immunity, thus hindering the body's innate ability to control the growth of cancerous cells. Recent immunotherapy research is studying how regulation of T cells could possibly be utilized in the treatment of cancer.

Regulatory T cells (suppressor T cells) can be important for the maintenance of immunological tolerance. Their major role is to shut down T cell-mediated immunity toward the end of an immune reaction and to suppress autoreactive T cells that escaped the process of negative selection in the thymus. Suppressor T cells along with Helper T cells can collectively be called Regulatory T cells due to their regulatory functions.

Two major classes of CD4+ $T_{reg}$ cells have been described—FOXP3$^+$ $T_{reg}$ cells and FOXP3$^-$ Treg cells.

Regulatory T cells can develop either during normal development in the thymus, and are then known as thymic $T_{reg}$ cells, or can be induced peripherally and are called peripherally derived $T_{reg}$ cells. These two subsets have been previously called "naturally occurring", and "adaptive" or "induced", respectively. Both subsets require the expression of the transcription factor FOXP3 which can be used to identify the cells. Mutations of the FOXP3 gene can prevent regulatory T cell development, causing the fatal autoimmune disease IPEX.

Several other types of T cell have suppressive activity, but do not express FOXP3. These include Tr1 cells and Th3 cells, which are thought to originate during an immune response and act by producing suppressive molecules. Tr1 cells are associated with IL-10, and Th3 cells are associated with TGF-beta. Recently, Treg17 cells have been added to this list.

Regulatory T Cell Populations.

T regulatory cells are a component of the immune system that can suppress immune responses of other cells. This is an important "self-check" built into the immune system to prevent excessive reactions. Regulatory T cells come in many forms with the most well-understood being those that express CD4, CD25, and FOXP3 (CD4+CD25+ regulatory T cells). These "Tregs" are different from helper T cells. Another regulatory T cell subset is Treg17 cells. Regulatory T cells are involved in shutting down immune responses after they have successfully eliminated invading organisms, and also in preventing autoimmunity.

CD4+ Foxp3+ regulatory T cells have been called "naturally occurring" regulatory T cells to distinguish them from "suppressor" T cell populations that are generated in vitro. Additional regulatory T cell populations include Tr1, Th3, CD8+CD28−, and Qa-1 restricted T cells. The contribution of these populations to self-tolerance and immune homeostasis is less well defined. Foxp3 can be used as a good marker for mouse CD4+CD25+ T cells, although recent studies have also shown evidence for Foxp3 expression in CD4+CD25− T cells. In humans, Foxp3 is also expressed by recently activated conventional T-cells and thus does not specifically identify human Tregs.

Development.

T cells can come from progenitor cells from the bone marrow, which become committed to their lineage in the thymus. T cells begin as CD4−CD8−TCR− cells at the DN (double-negative) stage, where an individual cell will rearrange its T cell receptor genes to form a unique, functional molecule, which they, in turn, test against cells in the thymic cortex for a minimal level of interaction with self-MHC. If they receive these signals, they proliferate and express both CD4 and CD8, becoming double-positive cells. The selection of Tregs occurs on radio-resistant haemopoietically-derived MHC class II-expressing cells in the medulla or Hassal's corpuscles in the thymus. At the DP (double-positive) stage, they are selected by their interaction with the cells within the thymus, begin the transcription of Foxp3, and become Treg cells, although they may not begin to express Foxp3 until the single-positive stage, at which point they are functional Tregs. Tregs do not have the limited TCR expression of NKT or γ δ T cells; Tregs have a larger TCR diversity than effector T cells, biased towards self-peptides.

The process of Treg selection is determined by the affinity of interaction with the self-peptide MHC complex. Selection to become a Treg is a "Goldilocks" process; a T cell that receives very strong signals will undergo apoptotic death; a cell that receives a weak signal will survive and be selected to become an effector cell. If a T cell receives an intermediate signal, then it will become a regulatory cell. Due to the stochastic nature of the process of T cell activation, all T cell populations with a given TCR will end up with a mixture of Teff and Treg—the relative proportions determined by the affinities of the T cell for the self-peptide-MHC. Even in mouse models with TCR-transgenic cells selected on specific-antigen-secreting stroma, deletion or conversion is not complete.

Foxp3+ Treg generation in the thymus is delayed by several days compared to Teff cells and does not reach adult levels in either the thymus or periphery until around three weeks post-partum. Treg cells require CD28 co-stimulation and B7.2 expression is largely restricted to the medulla, the development of which seems to parallel the development of Foxp3+ cells. It has been suggested that the two are linked, but no definitive link between the processes has yet been shown. TGF-β is not required for Treg functionality, in the thymus, as thymic Tregs from TGF-β insensitive TGFβRII-DN mice are functional.

Function.

The immune system must be able to discriminate between self and non-self. When self/non-self discrimination fails, the immune system destroys cells and tissues of the body and as a result causes autoimmune diseases. Regulatory T cells can actively suppress activation of the immune system and prevent pathological self-reactivity, i.e. autoimmune disease. The critical role regulatory T cells play within the immune system is evidenced by the severe autoimmune syndrome that results from a genetic deficiency in regulatory T cells (IPEX syndrome).

The molecular mechanism by which regulatory T cells exert their suppressor/regulatory activity has not been definitively characterized and is the subject of intense research. In vitro experiments have given mixed results regarding the requirement of cell-to-cell contact with the cell being suppressed. The immunosuppressive cytokines TGF-beta and Interleukin 10 (IL-10) have also been implicated in regulatory T cell function.

Another control mechanism is through the IL-2 feedback loop. Antigen-activated T cells produce IL-2 which then acts on IL-2 receptors on regulatory T cells alerting them to the fact that high T cell activity is occurring in the region, and they mount a suppressory response against them. This is a negative feedback loop to ensure that overreaction is not occurring. If an actual infection is present other inflammatory factors downregulate the suppression. Disruption of the loop leads to hyperreactivity, regulation can modify the strength of the immune response.

Induced Regulatory T Cells.

Induced Regulatory T (iTreg) cells (CD4+CD25+ Foxp3+) are suppressive cells involved in tolerance. iTreg cells have been shown to suppress T cell proliferation and experimental autoimmune diseases. These cells include Treg17 cells. iTreg cells develop from mature CD4+ conventional T cells outside of the thymus: a defining distinction between natural regulatory T (nTreg) cells and iTreg cells. Though iTreg and nTreg cells share a similar function iTreg cells have recently been shown to be "an essential non-redundant regulatory subset that supplements nTreg cells, in part by expanding TCR diversity within regulatory responses". Acute depletion of the iTreg cell pool in mouse models has resulted in inflammation and weight loss. The contribution of nTreg cells versus iTreg cells in maintaining tolerance is unknown, but both are important. Epigenetic differences have been observed between nTreg and iTreg cells, with the former having more stable Foxp3 expression and wider demethylation.

Regulatory T Cells and Disease.

An important question in the field of immunology is how the immunosuppressive activity of regulatory T cells is modulated during the course of an ongoing immune response. While the immunosuppressive function of regulatory T cells prevents the development of autoimmune disease, it is not desirable during immune responses to infectious microorganisms. Current hypotheses suggest that, upon encounter with infectious microorganisms, the activity of regulatory T cells may be downregulated, either directly or indirectly, by other cells to facilitate elimination of the infection. Experimental evidence from mouse models suggests that some pathogens may have evolved to manipulate regulatory T cells to immunosuppress the host and so potentiate their own survival. For example, regulatory T cell activity has been reported to increase in several infectious contexts, such as retroviral infections (the most well-known of which is HIV), mycobacterial infections (like tuberculosis), and various parasitic infections including Leishmania and malaria.

Studies of human subjects with a history of leishmania infection suggest that modulation of CD8+ suppressor T cells is, at least partly, mediated by cytokines. Leishmania specific CD4+ helper T cells predominate in adults with strong protective immunity (skin-test positive with no history of clinical infection). When added to autologous leishmania infected macrophages these T cells cause parasite death and secretion of large amounts of interferon-gamma and lymphotoxin. CD8+ T suppressor cells predominate in patients with no protective immunity (visceral leishmaniasis patients). When added to autologous peripheral blood mononuclear cells isolated after successful treatment, these T cells inhibit interferon-gamma secretion and proliferation and increase interleukin-6 and interleukin-10 secretion. A soluble factor(s) generated by antigen or phytohemagglutinin stimulation of leishmania-specific CD4+ helper T cells from skin-test positive adults killed CD8+ T cells but not CD4+ helper T cells when added to culture media. Soluble factors generated by antigen stimulation of peripheral blood mononuclear cells from skin-test positive adults prevented CD8+ suppressor T cell mediated increases in interleukin-10 secretion. These findings suggest that antigen stimulation of CD4+ helper T cells results in production of cytokines that kill or down regulate CD8+ T suppressor cells. Once the leishmania infection has been eliminated and leishmania antigens are gone, CD8+ T suppressor cells down-regulate CD4+ T helper cells. Isolation of cytokines that inhibit and kill CD8+ T suppressor cells might be useful in treating diseases that involve immune suppression such as leishmaniasis, AIDS, and certain cancers.

CD4+ Regulatory T cells are often associated with solid tumors in both humans and murine models. Increased numbers of regulatory T cells in breast, colorectal and ovarian cancers is associated with a poorer prognosis.

CD70+ non-Hodgkin lymphoma B cells induce Foxp3 expression and regulatory function in intratumoral CD4+ CD25− T cells.

A recent study shows that cerebral ischemia can increase bone marrow CD4(+)CD25(+)Foxp3(+) regulatory T cells via signals from the sympathetic nervous system.

Regulatory T Cells and Cancer.

Most tumors elicit an immune response in the host that is mediated by tumor antigens, thus distinguishing the tumor from other non-cancerous cells. This causes large numbers of tumor-infiltrating lymphocytes (TILs) to be found in the tumor microenvironment. Although it is not entirely understood, it is thought that these lymphocytes target cancerous cells and therefore slow or terminate the development of the tumor. However, this process is complicated because Tregs seem to be preferentially trafficked to the tumor microenvironment. While Tregs normally make up only about 4% of CD4+ T Cells, they can make up as much as 20-30% of the total CD4+ population around the tumor microenvironment.

Although high levels of TILs were initially thought to be important in determining an immune response against cancer, it is now widely recognized that the ratio of Tregs to Teffectors in the tumor microenvironment is a determining factor in the success of the immune response against the cancer. High levels of Tregs in the tumor microenvironment are associated with poor prognosis in many cancers, such as ovarian, breast, renal, and pancreatic cancer. This indicates that Tregs suppress Teffector cells and hinder the body's immune response against the cancer. However, in some types of cancer the opposite is true, and high levels of Tregs are associated with a positive prognosis. This trend is seen in cancers such as colorectal carcinoma and follicular lymphoma. This could be due to Treg's ability to suppress general inflammation which is known to trigger cell proliferation and metastasis. These opposite effects indicate that Treg's role in the development of cancer is highly dependent on both type and location of the tumor.

Although it is still not entirely understood how Tregs are preferentially trafficked to the tumor microenvironment, the chemotaxis is probably driven by the production of chemokines by the tumor. Treg infiltration into the tumor microenvironment is facilitated by the binding of the chemokine receptor CCR4, which is expressed on Tregs, to its ligand CCL22, which is secreted by many types of tumor cells. Treg expansion at the site of the tumor could also explain the increased levels of Tregs. The cytokine, TGF-β, which is commonly produced by tumor cells, is known to induce the differentiation and expansion of Tregs.

In general, the immunosuppression of the tumor microenvironment has largely contributed to the unsuccessful outcomes of many cancer immunotherapy treatments. Depletion of Tregs in animal models has shown an increased efficacy of immunotherapy treatments, and therefore, many immunotherapy treatments are now incorporating Treg depletion.

Molecular Characterization.

Similar to other T cells, regulatory T cells develop in the thymus. The latest research suggests that regulatory T cells are defined by expression of the forkhead family transcription factor Foxp3 (forkhead box p3). Expression of Foxp3 is required for regulatory T cell development and appears to control a genetic program specifying this cell's fate. The large majority of Foxp3-expressing regulatory T cells are found within the major histocompatibility complex (MHC) class II restricted CD4-expressing (CD4+) population and express high levels of the interleukin-2 receptor alpha chain (CD25). In addition to the Foxp3-expressing CD4+CD25+, there also appears to be a minor population of MHC class I restricted CD8+ Foxp3-expressing regulatory T cells. These Foxp3-expressing CD8+ T cells do not appear to be functional in healthy individuals but are induced in autoimmune disease states by T cell receptor stimulation to suppress IL-17-mediated immune responses. Unlike conventional T cells, regulatory T cells do not produce IL-2 and are therefore anergic at baseline.

A number of different methods are employed in research to identify and monitor Treg cells. Originally, high expression of CD25 and CD4 surface markers was used (CD4+ CD25+ cells). This is problematic as CD25 is also expressed on non-regulatory T cells in the setting of immune activation such as during an immune response to a pathogen. As defined by CD4 and CD25 expression, regulatory T cells comprise about 5-10% of the mature CD4+ T cell subpopulation in mice and humans, while about 1-2% of Treg can be measured in whole blood. The additional measurement of cellular expression of Foxp3 protein allowed a more specific analysis of Treg cells (CD4+CD25+Foxp3+ cells). However, Foxp3 is also transiently expressed in activated human effector T cells, thus complicating a correct Treg analysis using CD4, CD25 and Foxp3 as markers in humans. Therefore, some research groups use another marker, the absence or low-level expression of the surface protein CD127 in combination with the presence of CD4 and CD25. Several additional markers have been described, e.g., high levels of CTLA-4 (cytotoxic T-lymphocyte associated molecule-4) and GITR (glucocorticoid-induced TNF receptor) are also expressed on regulatory T cells, however the functional significance of this expression remains to be defined. There is a great interest in identifying cell surface markers that are uniquely and specifically expressed on all Foxp3-expressing regulatory T cells. However, to date no such molecule has been identified.

In addition to the search for novel protein markers, a different method to analyze and monitor Treg cells more accurately has been described in the literature. This method is based on DNA methylation analysis. Only in Treg cells, but not in any other cell type, including activated effector T cells, a certain region within the Foxp3 gene (TSDR, Treg-specific-demethylated region) is found demethylated, which allows to monitor Treg cells through a PCR reaction or other DNA-based analysis methods. Interplay between the Th17 cells and regulatory T cells are important in many diseases like respiratory diseases.

Recent evidence suggests that mast cells may be important mediators of Treg-dependent peripheral tolerance.

Regulatory T Cell Epitopes.

Regulatory T cell epitopes ('Tregitopes') were discovered in 2008 and consist of linear sequences of amino acids contained within monoclonal antibodies and immunoglobulin G (IgG). Since their discovery, evidence has indicated Tregitopes may be crucial to the activation of natural regulatory T cells.

Potential applications of regulatory T cell epitopes have been hypothesised: tolerisation to transplants, protein drugs, blood transfer therapies, and type I diabetes as well as reduction of immune response for the treatment of allergies.

Genetic Deficiency: Atg, Rubicon, DAP-1.

Figure 4:
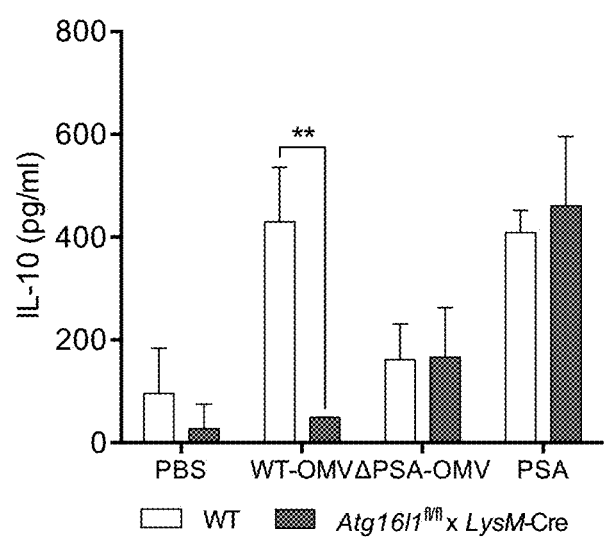
FIG. 4 is a bar graph showing Atg16l1$^{fl/fl}$ LysMCre DCs are unable to support B. fragilis OMV-induced IL-10 production. ELISA for IL-10 production from DC-T cell co-cultures with WT or Atg16l1$^{fl/fl}$ LysMCre DCs treated with PBS, B. fragilis WT-OMV, ΔPSA-OMV or purified PSA. Error bars represent S.E.M. ** $p<0.01$. Data are representative of at least 2 independent experiments.

As described herein, the Atg gene-dependent process of $T_{reg}$ cell generation was identified and shown to be relevant to human disease. In addition to Atg16, Atg5 and Atg7 are required for the generation of Tregs. It was shown that mutations in genetic pathways linked to IBD result in an inability to sense and/or respond to beneficial microbes. BMDCs from transgenic mice expressing the T300A allele (of ATG16L1) are also unable to promote IL-10 expression from Foxp3$^+$ Tregs in response to WT-OMVs. Further, ATG16L1 T300A transgenic mice are not protected from DNBS colitis and do not mount a potent Treg response when administered WT-OMV compared to WT mice. These findings prompted us to investigate if human immune cells from CD patients with the ATG16L1 T300A risk variant (TABLE 1, see Example 1) are also defective in promoting Foxp3+ Treg development by B. fragilis OMVs. Monocyte-derived dendritic cells (MoDC) from CD patients and healthy controls harboring either the protective allele (T300) or the risk allele (T300A) were pulsed with OMVs or PSA and co-cultured with syngeneic CD4+ T cells. Consistent with the mouse data, human cells homozygous for the risk allele are unable to support induction of IL-10 from Foxp3$^+$ Tregs by WT-OMVs compared to MoDCs carrying the protec-tive allele (FIG. 4). Remarkably, all samples tested display the predicted outcome based on genotype, and not disease status. However, cells from most subjects, regardless of genotype, respond to purified PSA (FIG. 4). Collectively, it was concluded that mouse and human DCs require functional ATG16L1 for induction of CD4$^+$Foxp3$^+$IL-10$^+$ Tregs in response to B. fragilis OMVs.

Genetic mutations in the gene encoding Foxp3 have been identified in both humans and mice based on the heritable disease caused by these mutations. This disease provides the most striking evidence that regulatory T cells play a critical role in maintaining normal immune system function. Humans with mutations in Foxp3 suffer from a severe and rapidly fatal autoimmune disorder known as Immune dysregulation, Polyendocrinopathy, Enteropathy X-linked (IPEX) syndrome.

The IPEX syndrome is characterized by the development of overwhelming systemic autoimmunity in the first year of life, resulting in the commonly observed triad of watery diarrhea, eczematous dermatitis, and endocrinopathy seen most commonly as insulin-dependent diabetes mellitus. Most individuals have other autoimmune phenomena including Coombs-positive hemolytic anemia, autoimmune thrombocytopenia, autoimmune neutropenia, and tubular nephropathy. The majority of affected males die within the first year of life of either metabolic derangements or sepsis. An analogous disease is also observed in a spontaneous Foxp3-mutant mouse known as "scurfy".

Because Rubicon is not a gene involved in standard or canonical autophagy, Rubicon can distinguish them from other autophagy patients. Thus, the requirement for a patient, as described herein, to have standard autophagy genes (atg5, atg16, atg7) and Rubicon is novel.

Figure 1D:
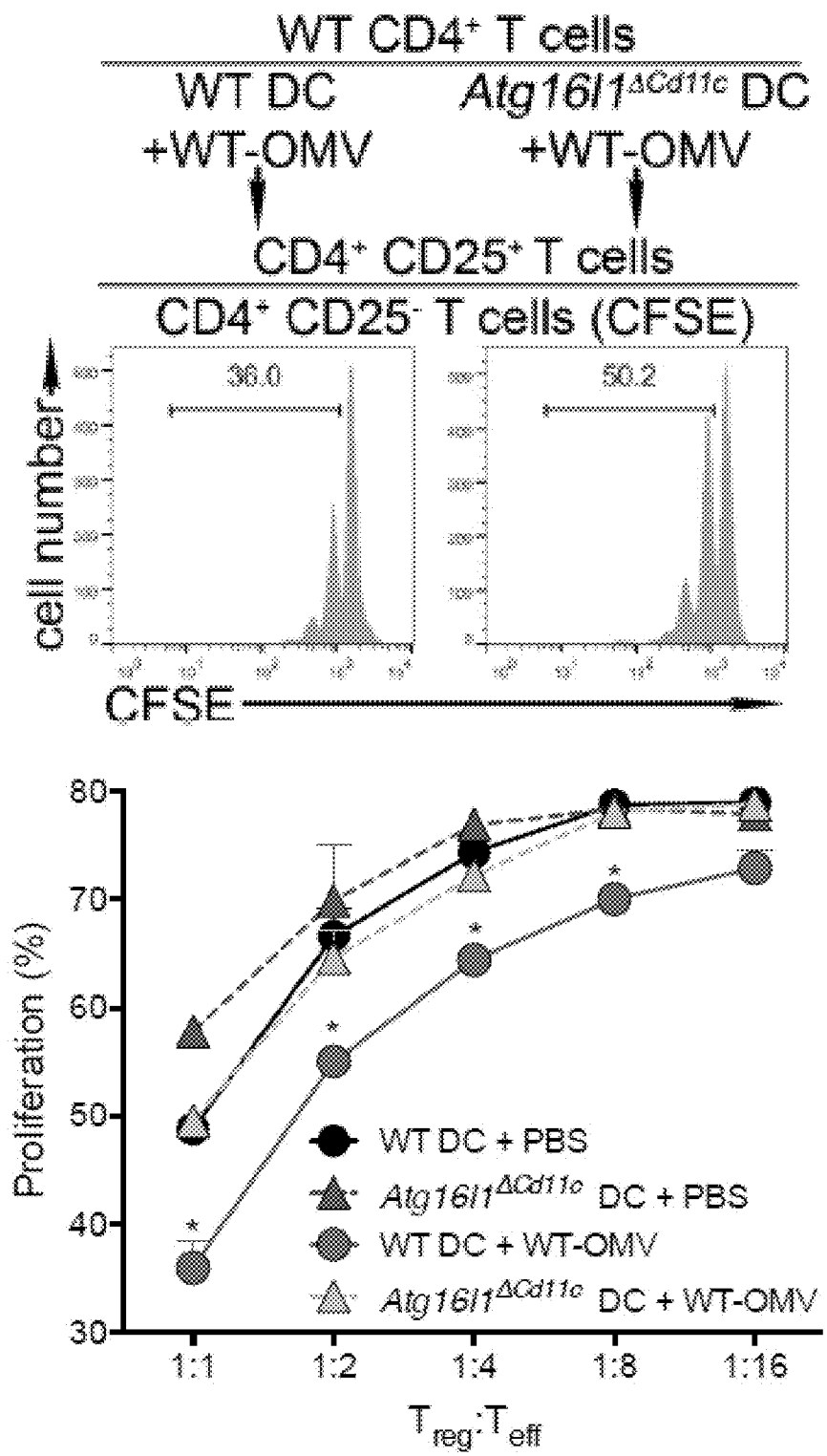
Figure 1F:
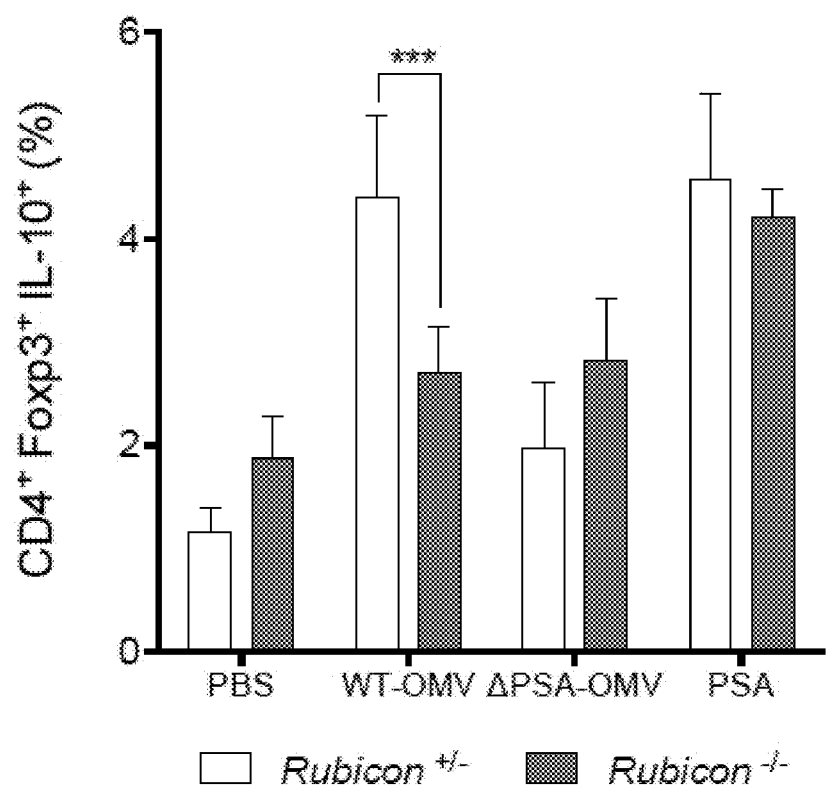
Figure 2:
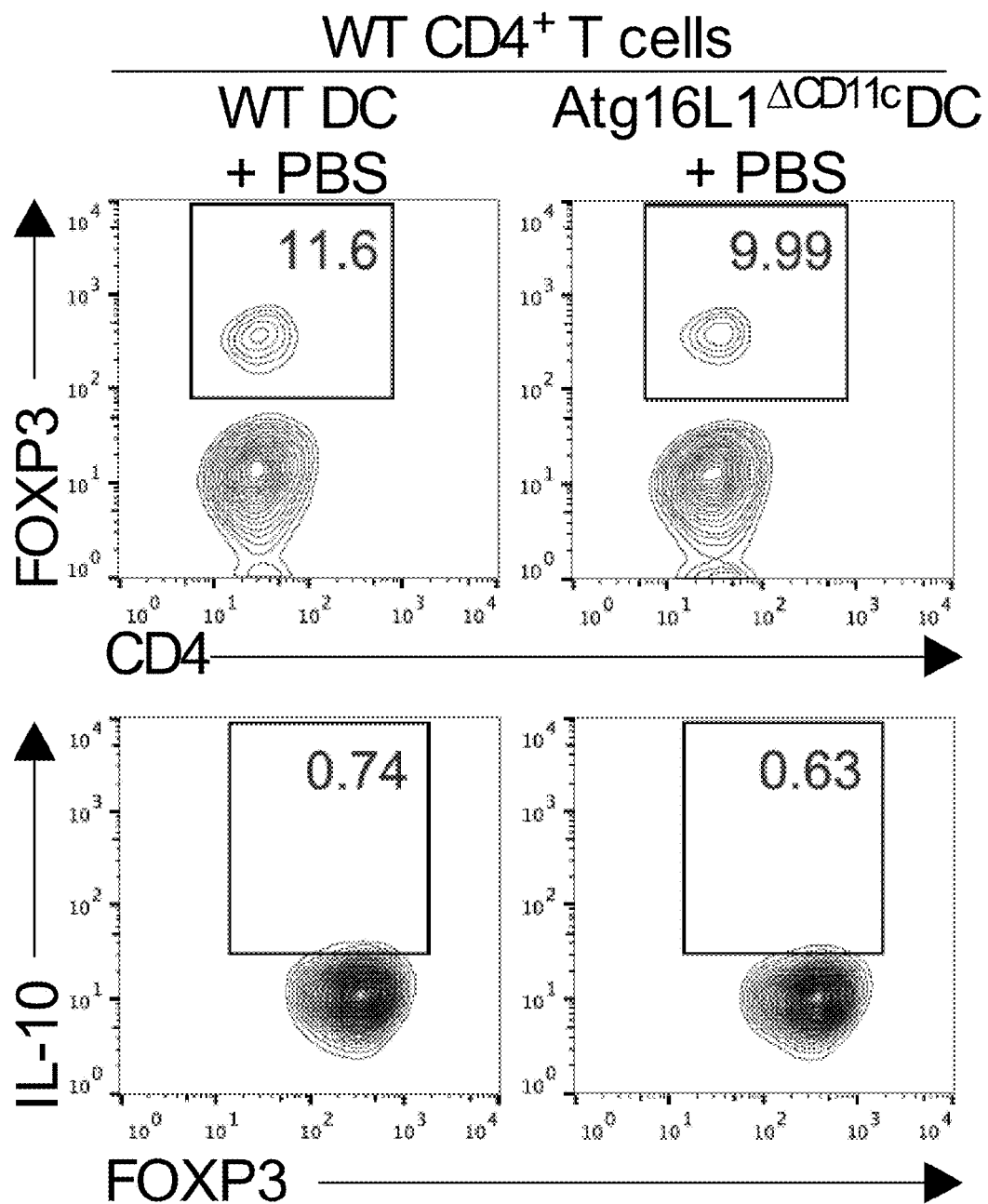
FIG. 2 is a series of representative flow cytometry plots of CD4$^+$Foxp3$^+$IL-10$^+$ $T_{regs}$ from DC-T cell co-cultures with WT and Atg16L1$^{\Delta CD11c}$ DCs treated with PBS (vehicle). Data are representative of at least 3 independent experiments.
Figure 8:
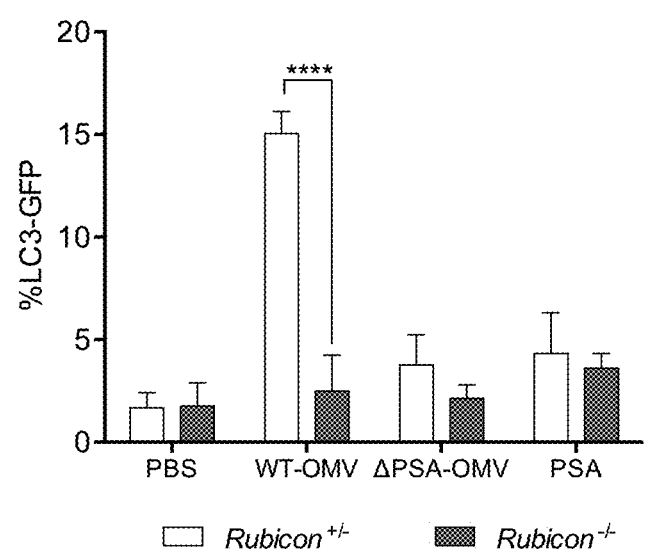
FIG. 8 is a bar graph showing B. fragilis WT-OMVs activate the LAP pathway. Quantification of LC3-GFP accumulation upon 2 h treatment of BMDCs with PBS, B. fragilis WT-OMV, ΔPSA-OMV or purified PSA in Rubicon$^{+/-}$ or Rubicon$^{-/-}$ DCs. Error bars represent S.E.M. **** p<0.0001. Data are representative of 3 independent experiments.

Example 2 describes LAP activation required RUBICON, which represses canonical autophagy. Rubicon+/− but not Rubicon−/− BMDCs display increased accumulation of lipidated, membrane-bound LC3-GFP (LC3-II) upon *B. fragilis* WT-OMV treatment (FIG. 1E). As expected, neither APSA-OMVs nor purified PSA are able to activate LAP (FIG. 8). Moreover, treatment of Rubicon−/− DCs fails to induce Treg responses (FIG. 1F). As RUBICON is upstream of ATG16L1 signaling, OMVs preferentially utilize the non-canonical autophagy pathway LAP to mediate tolerogenic responses to *B. fragilis*. Further, these data suggest a reconsideration of previous literature assigning the role of ATG16L1 in IBD to defects exclusively in autophagy.

DAP-1, implicated in ulcerative colitis, has a similar role in regulating Treg generation.

Therapeutic Methods

Also provided is a process of treating colitis, ileitis, or an inflammatory bowel disease in a subject in need thereof and administration of a therapeutically effective amount of a $T_{reg}$ (regulatory T cell) generating agent. For example, the treatment can protect from colitis, protect from ileitis, induce mucosal tolerance, or inhibit inflammatory response.

As described herein, because Atg16 is involved, and that the human risk gene mutation Atg16T300A exhibits the same defect that the loss of Atg16L1 exhibits, the findings in mice are directly linked to humans. As such, one can target the disclosed genes therapeutically and use as a diagnostic tool.

In some embodiments, treatment can include stem cells, antisense molecules, siRNA, down-/up-regulation, exon skipping, small organic molecules, fractions of tissues or cells, nucleic acids, polypeptides, aptamers, ribozymes, triple helix compounds, or antibodies. For example, the subject can be treated by repairing a defect in ATG16L1 or NOD2 gene. As another example, the defect in ATG16L1 can be T300A.

In some embodiments, the subject can be treated with ATG16L1 and NOD2 replacement therapy.

In some embodiments, the subject can be treated with gene therapy using a viral vector (e.g., adenovirus) to insert new gene into a cell, thereby making a functional ATG16L1 and NOD2 protein.

In some embodiments, the subject can be treated with gene repair using CRISPR-Cas9.

In some embodiments, exon skipping can be used to cause cells to "skip" over faulty or misaligned sections of genetic code, leading to a truncated but still functional protein despite the genetic mutation.

In some embodiments, antisense, siRNA can downregulate the gene variants implicated in colitis, ileitis, or inflammatory bowel disease.

Methods described herein are generally performed on a subject in need thereof. A subject in need of the therapeutic methods described herein can be a subject having, diagnosed with, suspected of having, or at risk for developing colitis, ileitis, inflammatory bowel disease, Crohn's disease, ulcerative colitis, ischemic colitis, colitis from allergic reactions, or microscopic colitis. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of $T_{reg}$ generating agent is, for example, that amount that would cause the desired therapeutic effect in a subject while minimizing undesired side effects. In various embodiments, an effective amount of a $T_{reg}$ generating agent described herein can substantially inhibit colitis, ileitis, or inflammatory disease, slow the progress of colitis, ileitis, or inflammatory disease, or limit the development of colitis, ileitis, or inflammatory disease.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a $T_{reg}$ generating agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to treat colitis, ileitis, or inflammatory disease.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a $T_{reg}$ generating agent can occur as a single event or over a time course of treatment. For example, a $T_{reg}$ generating agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for colitis, ileitis, or inflammatory disease.

A $T_{reg}$ generating agent can be administered simultaneously or sequentially with another agent, such as an antibiotic, an antiinflammatory, or another agent. For example, a $T_{reg}$ generating agent can be administered simultaneously with another agent, such as an antibiotic or an antiinflammatory. Simultaneous administration can occur through administration of separate compositions, each containing one or more of a $T_{reg}$ generating agent, an antibiotic, an antiinflammatory, or another agent. Simultaneous administration can occur through administration of one composition containing two or more of a $T_{reg}$ generating agent, an antibiotic, an antiinflammatory, or another agent. A $T_{reg}$ generating agent can be administered sequentially with an antibiotic, an antiinflammatory, or another agent. For example, a $T_{reg}$ generating agent can be administered before or after administration of an antibiotic, an antiinflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

In some embodiments, the $T_{reg}$ generating agent can be administered orally to directly target the lining of the gut Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening.

As described in Example 4, the present disclosure provides for screening for small molecules with (i) targeting the Atg gene-dependent process of presentation of bacterial pathogen associated molecular patterns (as embodied by PSA herein) to Treg cells to optimize the production of immunoregulatory Treg cells or screening for small molecules with (ii) targeting the specific genes identified herein as essential to this process such as for example Rubicon, Atg16L1 (including the disease-related mutation Atg16L1T300A), Atg7, and Atg5 with small molecules to optimize their function in this pathway.

The methods as described herein can be used in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Fragment-based lead discovery (FBLD) also known as fragment-based drug discovery (FBDD) is a method that can be used for finding lead compounds as part of the drug discovery process. It is based on identifying small chemical fragments, which may bind only weakly to the biological target, and then growing them or combining them to produce a lead with a higher affinity. FBLD can be compared with high-throughput screening (HTS). In HTS, libraries with up to millions of compounds, with molecular weights of around 500 Da, are screened, and nanomolar binding affinities are sought. In contrast, in the early phase of FBLD, libraries with a few thousand compounds with molecular weights of around 200 Da may be screened, and millimolar affinities can be considered useful.

In analogy to the rule of five, it has been proposed that ideal fragments should follow the 'rule of three' (molecular weight<300, ClogP<3, the number of hydrogen bond donors and acceptors each should be <3 and the number of rotatable bonds should be <3). Since the fragments have relatively low affinity for their targets, they must have high water solubility so that they can be screened at higher concentrations.

In fragment-based drug discovery, the low binding affinities of the fragments pose significant challenges for screening. Many biophysical techniques have been applied to address this issue. In particular, ligand-observe nuclear magnetic resonance (NMR) methods such as water-ligand observed via gradient spectroscopy (waterLOGSY), saturation transfer difference spectroscopy (STD-NMR), 19F NMR spectroscopy and inter-ligand Overhauser effect (ILOE) spectroscopy, protein-observe NMR methods such as 1H-15N heteronuclear single quantum coherence (HSQC) that utilises isotopically-labelled proteins, surface plasmon resonance (SPR) and isothermal titration calorimetry (ITC) are routinely-used for ligand screening and for the quantification of fragment binding affinity to the target protein.

Once a fragment (or a combination of fragments) have been identified, protein X-ray crystallography can be used to obtain structural models of the protein-fragment(s) complexes. Such information can then be used to guide organic synthesis for high-affinity protein ligands and enzyme inhibitors.

There can be advantages of screening low molecular weight fragment based libraries over traditional higher molecular weight chemical libraries, including:

More hydrophilic hits in which hydrogen bonding is more likely to contribute to affinity (enthalpically driven binding). It is generally much easier to increase affinity by adding hydrophobic groups (entropically driven binding), starting with a hydrophilic ligand increases the chances that the final optimized ligand will not be too hydrophobic (log P<5).

Higher ligand efficiency so that the final optimized ligand will more likely be relatively low in molecular weight (MW<500).

Since two to three fragments in theory can be combined to form an optimized ligand, screening a fragment library of N compounds is equivalent to screening $N^2$-$N^3$ compounds in a traditional library.

Fragments are less likely to contain sterically blocking groups that interfere with an otherwise favorable ligand-protein interaction, increasing the combinatorial advantage of a fragment library even further.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Materials and Methods

The following example describes the materials and methods. Unless noted otherwise, the following examples use the materials and methods described below.

Mice

C57BL/6 mice were purchased from Taconic Farms. Nod2$^{-/-}$ mice were purchased from the Jackson Laboratory. Atg16/1$^{fl/fl}$ Cd11c-Cre$^{-/-}$ (WT), Atg16/1$^{fl/fl}$ Cd11c-Cre$^{+/-}$ (Atg16L1$^{\Delta CD11c}$) Atg16l1$^{fl/fl}$ LysM-Cre, Atg5$^{fl/fl}$ LysM-Cre, Atg7$^{fl/fl}$ LysM-Cre, Atg14$^{fl/fl}$ LysM-Cre, Fip200$^{fl/fl}$ LysM-Cre mice and femurs were obtained from H. W. Virgin (41, 42), ATG16L1 T300A mice from R. J. Xavier (22), and Ulk1$^{-/-}$ and Rubicon$^{-/-}$ mice and femurs from M. Kundu (43) and D.

R. Green (35) under a materials transfer agreement with St. Jude Children's Research Hospital, respectively. For all studies performed with Cre-floxed mice, the Cre$^{-/-}$ littermates served as wildtype controls. 8-10 week old sex-matched mice were used in the study. All procedures were performed in accordance with the guidelines and approved protocols from the Institutional Animal Care and Use Committee at the California Institute of Technology.

Human Peripheral Blood Mononuclear Cells

Crohn's disease subjects were recruited from the IBD Center at Cedars-Sinai Medical Center following informed consent and IRB approval. ATG16L1 genotyping was performed using the Immunochip (Illumina, San Diego, Calif., USA) according to the manufacturer's instructions and as previously described (10). Patient sample information is described in TABLE 1.

TABLE 1

Human Subjects. Sample ID, disease status, ATG16L1 genotype, sex, age, and medications taken at time of blood collection. CTL, control; CD, Crohn's disease; F, female; M, male.

| Sample ID | Disease Status | Genotype | Sex | Age | Medications |
|---|---|---|---|---|---|
| CTL01 | Normal | T300 (AA) | F | 32 | N/A |
| CTL02 | Normal | T300 (AA) | F | 40 | N/A |
| CTL03 | Normal | T300 (AA) | F | 63 | N/A |
| CD04 | CD | T300 (AA) | M | 57 | N/A |
| CD05 | CD | T300 (AA) | M | 53 | N/A |
| CD06 | CD | T300 (AA) | M | 39 | N/A |
| CTL07 | Normal | T300A(GG) | F | 44 | N/A |
| CTL08 | Normal | T300A (GG) | F | 68 | N/A |
| CD09 | CD | T300A (GG) | F | 28 | mercaptopurine (Purinethol); mesalamine (Apriso) adallmumab (Humira); *Bifidobacterium infantis* (Align); multivitamin; |
| CD10 | CD | T300A (GG) | F | 27 | Noreth A-ET Estra/FE Fumarate (Lo Loestrin FE PO), Omega-3 Fatty Acids-Vitamin E (fish Oil); Resveratrol |
| CD11 | CD | T300A (GG) | M | 37 | N/A |
| CD12 | CD | T300A (GG) | | 23 | N/A |

Bacterial Strains, Culture Conditions and OMV Purification

*Bacteroides fragilis* strain NCTC9343, *Bacteroides thetaiotamicron* ATCC 29148 and *Bacteroides vulgatus* ATCC 8482 were obtained from the American Type Culture Collection, and *B. fragilis* ΔPSA has been described previously (44). *Bacteroides* strains were grown anaerobically (80% $N_2$, 10% $H_2$, 10% $CO_2$) at 37° C. in brain heart infusion broth (BD Biosciences) supplemented with 5 µg/ml hemin (Sigma) and 0.5 µg/ml vitamin K (Sigma). *Salmonella enterica* serovar Typhimurium (IR715), a nalidixic acid-resistant strain of 14028, was a generous gift from A. Bäumler. S. Typhimurium were grown aerobically at 37° C. in Luria-Bertani (LB) broth. For the induction of OMVs, *Bacteroides* strains were grown in minimal media, which consisted of RPMI 1640, no phenol red (Life Technologies) supplemented with 1% fetal bovine serum (Life Technologies), 8 mg/ml glucose (Sigma), 2.5 µg/ml hemin (Sigma) and 0.25 µg/ml vitamin K (Sigma). *B. fragilis* OMV isolation was performed as previously described (32). Briefly, electron dense layer-enriched *B. fragilis* (45) was grown in minimal media for 24 hr anaerobically. OMVs were recovered from the bacteria-free culture supernatant by ultracentrifugation, washed, resuspended in PBS and filtered through a 0.4 µm filter (Millipore) prior to treatment of cell cultures or oral gavage of mice.

Experimental Colitis

WT (Atg1611$^{fl/fl}$ Cd11c-Cre$^{-/-}$), ATG16L1-deficient (Atg1611$^{fl/fl}$ Cd11c-Cre$^{+/-}$, Atg16L1$^{\Delta CD11c}$), ATG16L1 T300A, or Nod2$^{-/-}$ mice were orally gavaged with PBS or WT-OMV (5 µg) every other day for one week prior to 2,4-dinitrobenzenesulfonic acid (DNBS; Sigma) administration. On day 7, mice were anesthetized with isofluorane, and rectal administration of 5% DNBS in 50% ethanol was applied through a 3.5F catheter (Instech Solomon), as previously described (32). Control groups received ethanol (Sham). Briefly, a flexible silicone catheter was inserted 4 cm into the colon, and the mice were held in a vertical position for at least 1 min after rectal administration. Mice were monitored and weighed daily for the duration of the experiment. Upon sacrifice, gut tissue was harvested, fixed in neutral 10% buffered formalin, embedded in paraffin, sectioned and stained with hematoxylin and eosin (H&E). All histology was evaluated in a blinded analysis by two veterinarians using a comprehensive scoring system. Hematoxylin-eosin-stained slides were scanned and digitally scored using a while slide imaging system (Hamamatsu NanoZoomer Slide Scanner 2.0HT). Slides were read using software (Hamamatsu NanoZoomer Viewer NDP.View 2.3.1) to allow the use of a web-based file-sharing platform. Colitis was classified into acute, chronic and chronic active, depending on the existence of vascular reaction (hyperemia, edema, hemorrhage). In addition, the predominant types of leukocytes in the infiltrates were considered (polymorphonuclear and/or mononuclear). The extension and the nature of the lesions allowed defining the distribution (focal, multifocal, locally extensive or diffuse) and the intensity (discrete, moderate, severe, transmural). Scoring was based on a modification of an approach described previously (46). Briefly, the number and distribution of mucosal polymorphonuclear cells as well as mononuclear cells and epithelial cell damage were scored from 0-4. The submucosa was scored for cellular infiltrates from 0-3 while the thickening and cellular infiltrates in the muscularis were scored from 0-2. All photomicrographs were captured using NanoZoomer Viewer NDP View 2.3.1 and scored using the same criteria by two people (P.B.E. and A.C.V.), including a comparative pathologist (A.C.V).

In Vitro DC-T Cell Co-Culture

Co-culture of bone marrow-derived dendritic cells (BM-DCs) and CD4$^+$ T cells were performed as previously described (30, 32, 36). Briefly, BMDCs were generated from bone marrow progenitor cells isolated from femurs of WT or Atg16L1$^{\Delta CD11c}$ mice in the presence of 20 ng/ml GM-CSF (Miltenyi) in complete RPMI media 1640 (10% fetal bovine serum, 50 U/ml penicillin, 50 µg/ml streptomycin, 2 mM L-glutamine, 1 mM sodium pyruvate, 1 mM HEPES, and non-essential amino acids, and β-mercaptoethanol). BMDCs were pulsed with PBS, WT-OMVs (10 µg/ml), ΔPSA-OMVs (10 µg/ml) or pure PSA (50 µg/ml) for 18-22 hrs; OMVs with a protein content of 10 µg contain 50 µg of PSA. BMDCs were washed, and co-cultured with splenic CD4$^+$ T cells at a ratio of 1:10 (DC:CD4$^+$ T cells) in the presence of 0.1 µg/ml anti-mouse CD3 and 5 ng/ml of recombinant human TGF-β (Peprotech). After 3-5 days of co-culture, supernatants were collected for enzyme-linked immunosorbent assay (ELISA) analysis and cells stained with specific antibodies and a viability dye for analysis by flow cytometry.

To generate monocyte-derived dendritic cell (MoDCs), human PBMCs were isolated from fresh whole blood the same day of harvest using Ficoll-Hypaque (GE Healthcare) gradient (density=1.070 g/ml), followed by monocyte enrichment using the Human Monocyte Isolation Kit II (Miltenyi). For differentiation into MoDCs, monocytes were incubated with recombinant human IL-4 and GM-CSF (Peprotech) every two days in complete RPMI 1640 (5% human AB serum, 50 U/ml penicillin, 50 µg/ml streptomycin, 2 mM L-glutamine, 1 mM sodium pyruvate, 1 mM HEPES, non-essential amino acids, 3-mercaptoethanol). MoDCs were pulsed with PBS, *B. fragilis* OMVs or PSA for 18-22 hrs, washed, and co-cultured with syngeneic CD4$^+$ T cells, isolated using the Human CD4 Isolation Kit II (Miltenyi), at a ratio of 1:10 (DC:CD4$^+$ T cells) in the presence of 1 mg/ml anti-human CD3 (eBiosciences) and 5 ng/ml of recombinant human TGF-β (Peprotech). After 6 days of co-culture, cells were restimulated with phorbol 12-myristate 13-acetate (PMA) (Sigma) and ionomycin (Calbiochem) in the presence of GolgiPlug (BD Biosciences) for 4.5 hr, and stained with specific antibodies and a viability dye for analysis by flow cytometry.

In Vitro T Cell Suppression Assay

CD4$^+$CD25$^+$ T$_{reg}$ cells were purified from in vitro BMDC-T cell co-cultures using magnetic microbeads (Miltenyi). CD4$^+$CD25$^-$ responder effector T cells (T$_{eff}$) were isolated from mouse spleens, labeled with 2.5 µM CFSE for 10 min at 37° C. in the dark, washed, and incubated with T$_{reg}$ cells at various T$_{reg}$:T$_{eff}$ ratios in the presence of 1 µg/ml anti-mouse CD3 (eBiosciences). Irradiated CD4-depleted mouse splenocytes served as antigen-presenting cells. Cultures were incubated for 48 and 72 hrs, cells were stained with specific antibodies and a viability dye, and analyzed by flow cytometry. Dilution of CFSE signal is a measure of proliferation, and inhibition of proliferation a measure of T$_{reg}$ activity.

Isolations of Cells from Tissues

Isolation of colon lamina propria (cLP) lymphocytes was performed, as previously described (30, 32, 36). Briefly, colons were cut open longitudinally, and luminal contents flushed with ice-cold PBS. Colons were cut into 1 cm pieces and incubated for 20 min in 10 mM dithiothreitol (Sigma) with gentle shaking, followed by two incubations at 20 min in 20 mM EDTA (Sigma). Supernatants were removed and remaining tissue was incubated in 1 mg/ml Collagenase D (Sigma), 0.25 U/ml Dispase (Roche), and 0.5 mg/ml DNase I (Worthington). Cells were filtered through a 70 µm cell strainer (BD Falcon) and separated by a 40%/80% (v/v) Percoll (GE Healthcare) density gradient. Cells were washed prior to staining for flow cytometry.

MLN and spleens were processed by grinding tissues through 100 µm cell strainer (BD Falcon) to generate single cell suspensions. Splenic cells were treated with RBC lysis buffer (Sigma) and washed prior to staining for flow cytometry.

Flow Cytometry, Intracellular Cytokine Staining, and ELISA

Cells were incubated in 5% mouse serum for 15 min and stained for 20 min at 4° C. with either LIVE/DEAD fixable green or far red dead stain kit (Life Technologies), with empirically titrated concentrations of the following antibodies: PerCP-Cy5.5-conjugated anti-mouse CD4 (clone: RM4-5), PerCP-Cy5.5-conjugated anti-human CD4 (clone: OKT4), and/or PE-Cy7-conjugated anti-mouse CD4 (clone: RM4-5). For intracellular staining, cells were fixed and permeabilized with the Foxp3/Transcription factor buffer kit (eBioscience). Intracellular staining was performed using the following antibodies: FITC-conjugated anti-mouse IFNγ (clone: XMG1.2), PE-conjugated anti-mouse IL-10 (clone: JESS-16E3), PE-conjugated anti-human Foxp3 (clone: PCH101), PerCP-Cy5.5 anti-mouse IL-17A (clone: eBio17B7), APC-conjugated anti-mouse Foxp3 (clone: FJK-16s), and/or APC-conjugated anti-human IL-10 (clone: JES3-9D7). All antibodies were purchased from eBioscience. ROS detection was performed as previously described (35). Briefly, BMDCs were incubated with 1 µM dihydroethidium (Life Technologies) for 30 min at 37° C. in the dark. Cells were washed and acquired immediately. Cell acquisition was performed on a BD FACS Calibur (BD Biosciences) or Miltenyi MACSQuant (Miltenyi), and data was analyzed using FlowJo software suite (TreeStar). For ELISAs, cell supernatant from in vitro DC-T cell co-culture were collected and mouse IL-10 and IL-17A were measured using commercially available kits (eBiosciences).

RNA Isolation and Quantitative Real Time RT-PCR

BMDCs were harvested, washed, and immediately lysed in RLT buffer for RNA isolation using the RNeasy Mini Kit, according to manufacturer's protocol (Qiagen). 1 µg of RNA was reverse transcribed using iScript cDNA Synthesis Kit, according to manufacturer's protocol (Bio-Rad) and diluted to 10 ng/µl based on the input concentration of total RNA.

Gene specific primers were designed using MacVector software and synthesized by Integrated DNA Technologies. Real-time PCR for the mammalian housekeeping gene β-actin was used to ensure that input RNA was equal among all samples. Real-time PCR was performed on cDNA using the ABI PRISM 7900 HT (ThermoFisher).

Western Blot

BMDCs were washed with PBS and lysed with 1×RIPA buffer (EMD Millipore) with protease inhibitor cocktail (Roche). Protein concentration was determined using BCA protein assay (Pierce). Samples were analyzed on 4-20% Tris-Glycine gels (Novex) and proteins were transferred to Immobilon-P PVDF membrane (EMD Millipore). The membrane was blocked in 5% nonfat dry milk and probed for α-PSA (1:1000) or α-mouse β-actin (1:3000) (Cell Signaling) rabbit polyclonal antibodies with a horseradish peroxidase (HRP)-conjugated goat α-rabbit secondary antibody (1:5000) (KPL) and developed using LumiGLO chemiluminescent substrate (KPL). Chemiluminescent signal was detected with the Gel Doc™ XR+ System (Bio-Rad).

Statistical Analyses

Student's t-test was used for pairwise comparisons. Survival curve was analyzed using the Grehan-Breslow-Wilcoxin test. One-way and two-way ANOVA with Post-hoc Tukey test were used for comparisons among one or two or more groups, respectively, using the GraphPad PRISM software.

Example 2: *Bacteroides* Fragilis Induced Immune Response

The microbiome of CD patients is altered, with emerging evidence for cause and effects relationships to disease. Among other recent examples of host-microbe interactions, the human commensal *Bacteroides* fragilis has evolved beneficial immunomodulatory properties. During colonization of mice, *B. fragilis* capsular Polysaccharide A (PSA) is packaged in outer membrane vesicles (OMVs) and delivered to intestinal dendritic cells to induce interleukin-10 (IL-10) production from CD4$^+$Foxp3$^+$ regulatory T cells (T$_{regs}$), which protect from experimental colitis.

To explore gene-environment interactions during host-microbiota symbiosis, genetic pathways linked to CD are involved in the immune response to *B. fragilis* OMVs were tested.

Figure 3B:
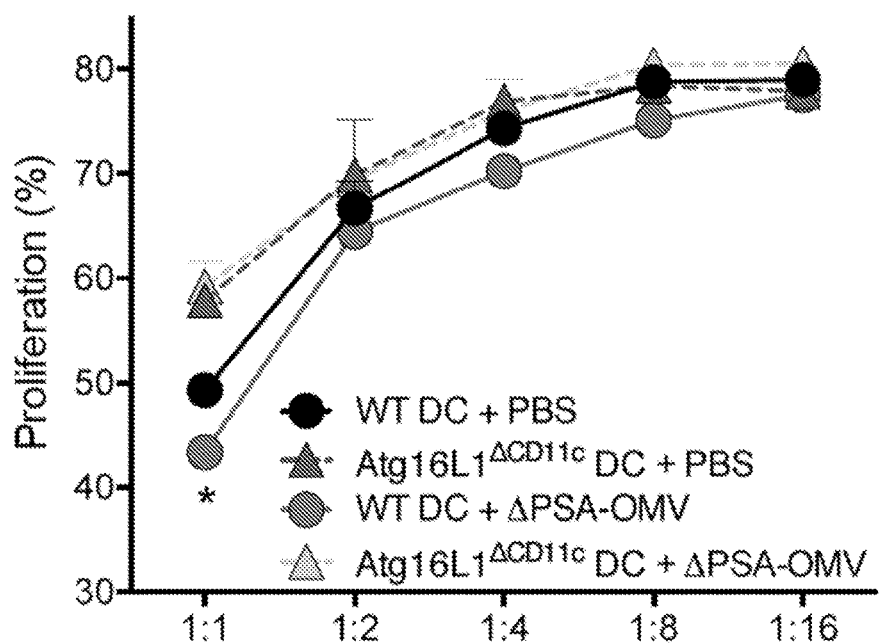
Figure 3C:
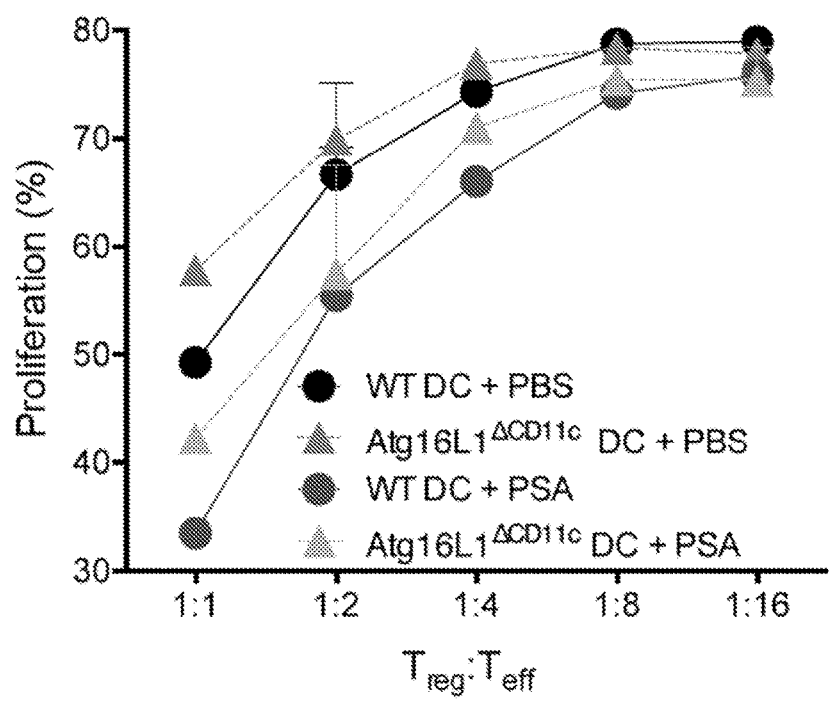
Figure 5:
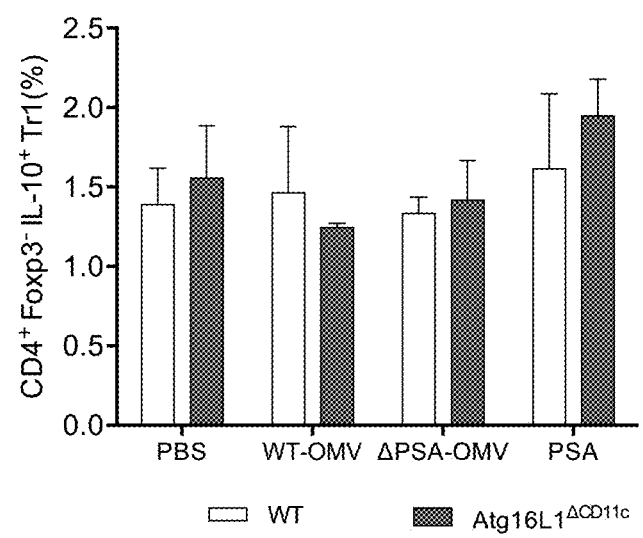
FIG. 5 is a bar graph showing B. fragilis OMVs do not induce IL-10 production among Foxp3$^-$ type 1 regulatory (Tr1) cells. Frequency of CD4$^+$ Foxp3$^-$IL-10$^+$$T_{regs}$ from DC-T cell co-cultures with WT or Atg16L1$^{\Delta CD11c}$ DCs treated with PBS, B. fragilis WT-OMV, ΔPSA-OMV or purified PSA. Data are representative of 3 independent experiments.
Figures 6A, 6B:
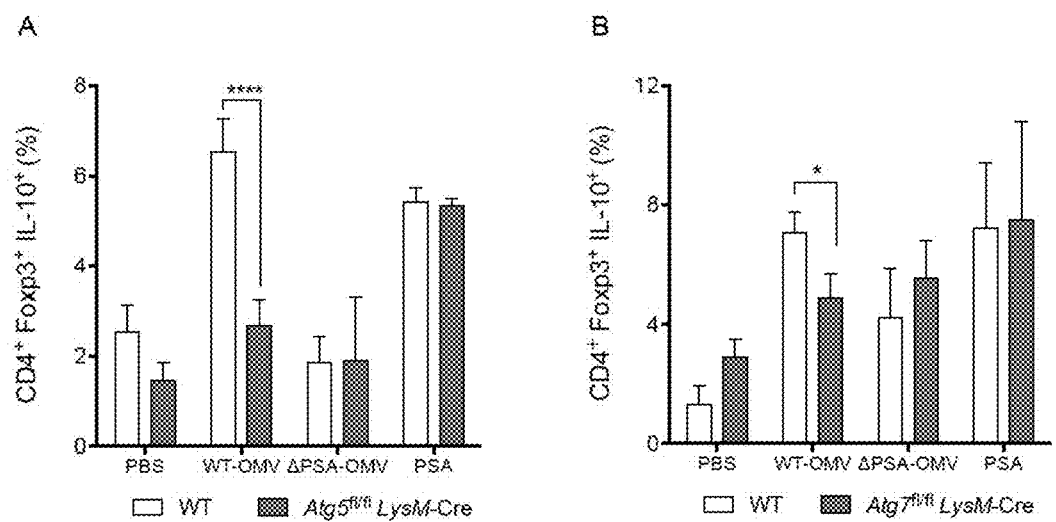
FIG. 6A-FIG. 6B is a series of bar graphs showing B. fragilis OMVs require Atg5 and Atg7 to promote IL-10 production from Foxp3$^+$$T_{regs}$. Proportions of IL-10 expression among CD4$^+$ Foxp3$^+$ $T_{regs}$ following PBS, B. fragilis WT-OMV, ΔPSA-OMV or purified PSA treatment of (FIG. 6A) WT and Atg5$^{fl/fl}$ LysMCre or (FIG. 6B) Atg7$^{fl/fl}$ LysMCre BMDCs co-cultured with CD4$^+$ T cells. Error bars represent S.E.M. * $p<0.05$, **** $p<0.0001$. Data are representative of at least 3 independent experiments.

Bone marrow-derived DCs (BMDCs) differentiated from wild-type (WT) and ATG16L1-deficient (Atg16l$^{fl/fl}$ Cd11cCre, Atg16L1$^{\Delta CD11c}$) mice were pulsed with OMVs harvested from wild-type *B. fragilis* (WT-OMV) or an isogenic mutant lacking PSA (ΔPSA-OMV), and co-cultured with CD4$^+$ T cells. As previously reported (33), WT-OMVs, but not vehicle or ΔPSA-OMVs, promote IL-10 production (FIG. 1A to FIG. 1C, FIG. 2 and FIG. 3). Conversely, ATG16L1-deficient DCs do not support IL-10 production in response to WT-OMVs (FIG. 1, A to C). Similar results were observed using Atg16L1$^{fl/fl}$ LysMCre mice (FIG. 4). Purified PSA does not require ATG16L1 for its activity (FIG. 1A and FIG. 1C, FIG. 3). Next, functional outcomes were tested using in vitro T cell suppression assays. T$_{regs}$ isolated from co-cultures with Atg16L1$^{\Delta CD11c}$ BMDCs treated with *B. fragilis* OMVs exhibit impaired suppressive activity (FIG. 1D and FIG. 3A). Neither WT-OMVs nor pure PSA have any effect on IL-10 production among CD4$^+$Foxp3$^-$ type 1 regulatory T cells (FIG. 5). ATG16L1, ATG5 and ATG7 are components of the autophagy elongation complex; BMDCs deleted in these genes likewise do not induce IL-10 production from T$_{regs}$ (FIG. 6). Further, recent reports reveal a role for autophagy components in T$_{reg}$ homeostasis. The findings indicate that ATG16L1-deficient DCs fail to respond to *B. fragilis* OMVs, demonstrating that autophagy components in DCs are required for commensal-driven T$_{reg}$ induction and function.

Figure 7A:
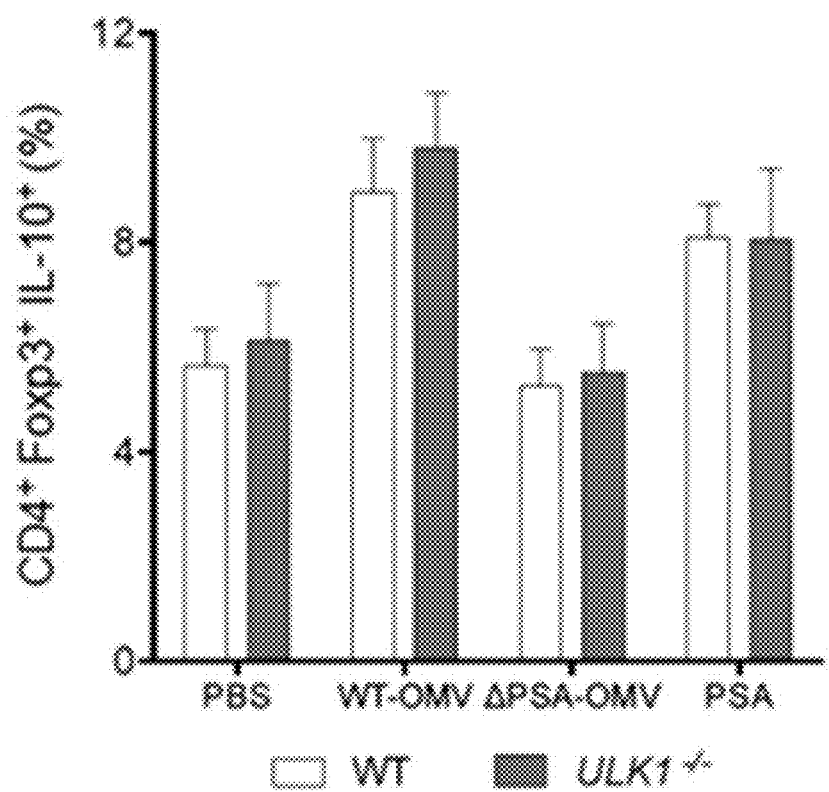
FIG. 7A-FIG. 7C is a series of bar graphs showing B. fragilis OMVs do not require canonical autophagy to promote IL-10 production in Foxp3$^+$T$_{regs}$. The requirement of canonical autophagy was examined using (FIG. 7A) Ulk1$^{-/-}$, (FIG. 7B) Fip200$^{fl/fl}$ LysMCre or (FIG. 7C) Atg14$^{fl/fl}$ LysMCre BMDCs treated with PBS, B. fragilis WT-OMV, ΔPSA-OMV or purified PSA, then co-cultured with CD4$^+$ T cells. Measurement of IL-10$^+$ cells among the Foxp3$^+$ T$_{reg}$ population by flow cytometry. Error bars represent S.E.M. Data are representative of at least 3 independent experiments.
Figure 7B:
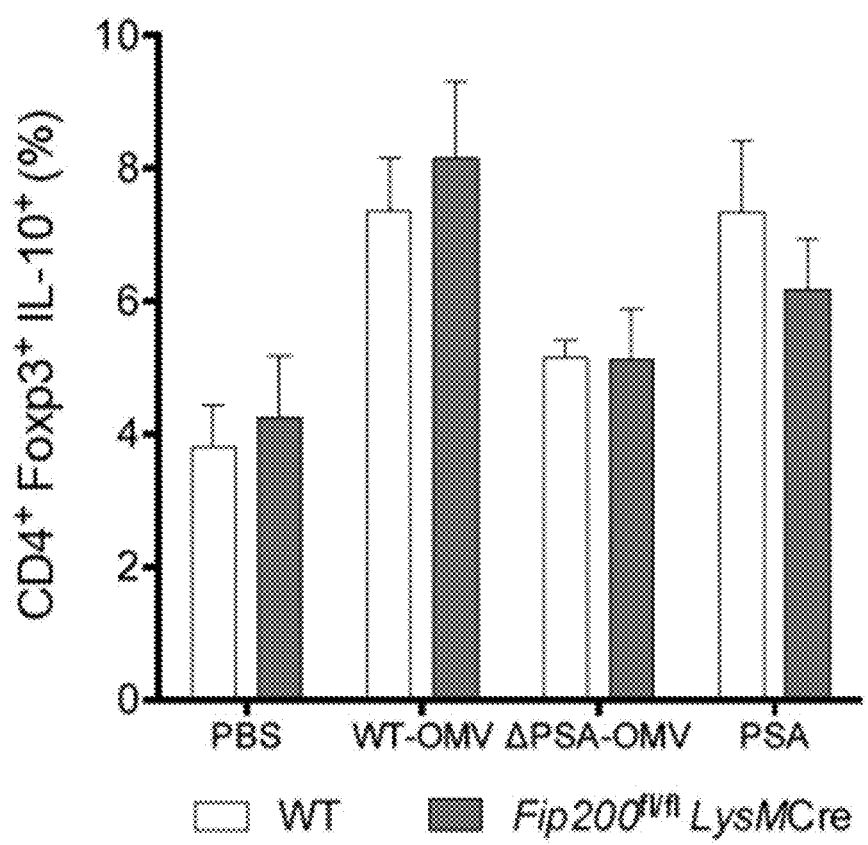
Figure 7C:
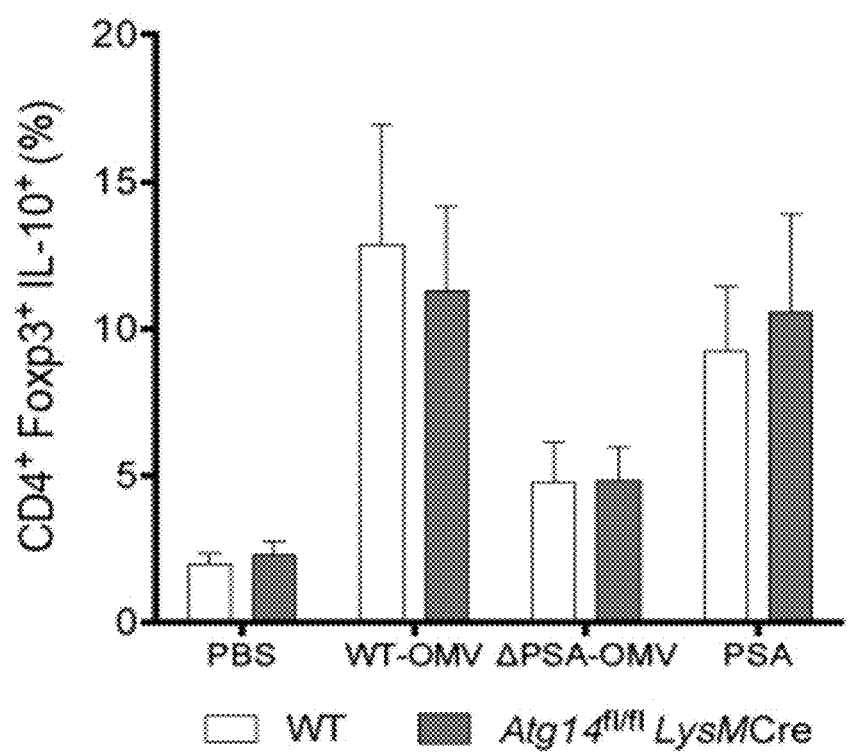

ATG16L1, ATG5 and ATG7 participate in both canonical and non-canonical autophagy pathways. Interestingly, the classical autophagy-specific genes Ulk1, Fip200 or Atg14 are not required for CD4$^+$Foxp3$^+$IL-10$^+$ T$_{reg}$ induction upon WT-OMV treatment (FIG. 7). It was hypothesized that OMVs utilize the non-canonical autophagy pathway, LC3-associated phagocytosis (LAP), which is specifically activated by microbial ligands delivered as particles rather than soluble molecules. LAP activation requires RUBICON, which represses canonical autophagy. Rubicon$^{+/-}$ but not Rubicon$^{-/-}$ BMDCs display increased accumulation of lipidated, membrane-bound LC3-GFP (LC3-II) upon *B. fragilis* WT-OMV treatment (FIG. 1E). As expected, neither APSA-OMVs nor purified PSA are able to activate LAP (FIG. 8). Moreover, treatment of Rubicon$^{-/-}$ DCs fails to induce T$_{reg}$ responses (FIG. 1F). As RUBICON is upstream of ATG16L1 signaling, OMVs preferentially utilize the non-canonical autophagy pathway LAP to mediate tolerogenic responses to *B. fragilis*. Further, these data suggest a reconsideration of previous literature assigning the role of ATG16L1 in IBD to defects exclusively in autophagy.

Figure 9B:
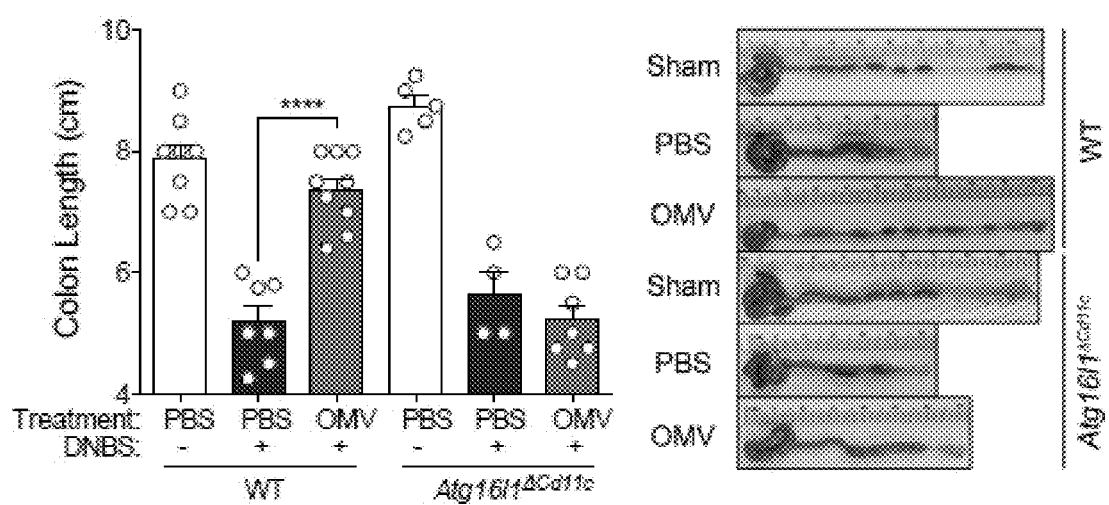
Figure 9C:
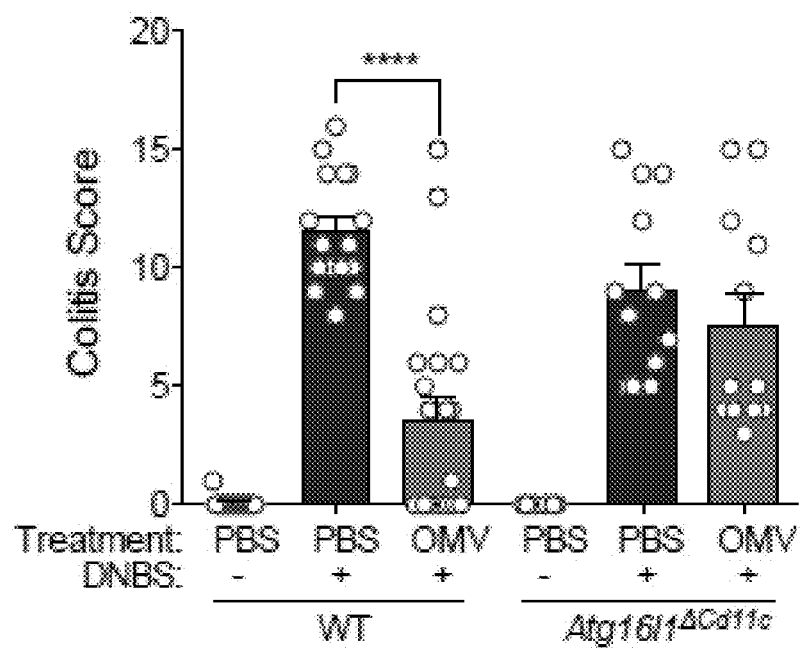
Figure 9C:
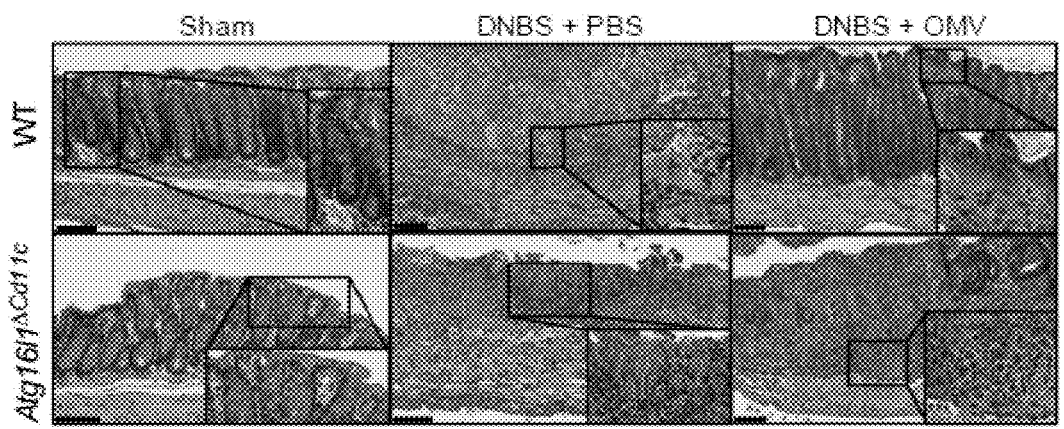
Figure 9D:
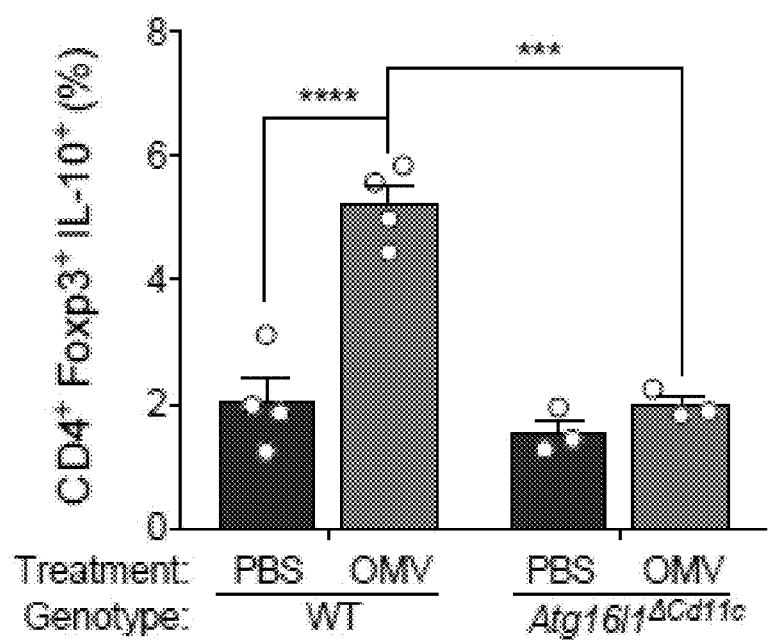
Figures 10A, 10B, 10C:
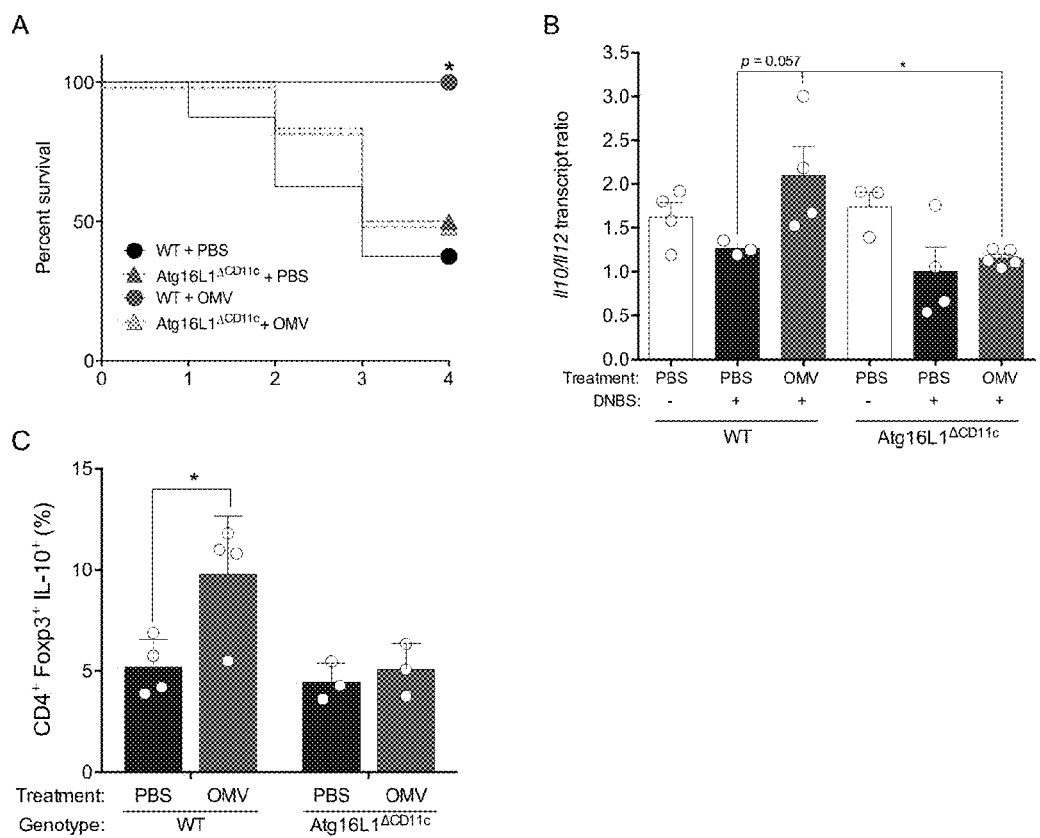
FIG. 10A-FIG. 10C is a plot and bar graphs showing B. fragilis OMV-mediated protection from colitis requires ATG16L1 in DCs.
Figures 11A, 11B, 11C:
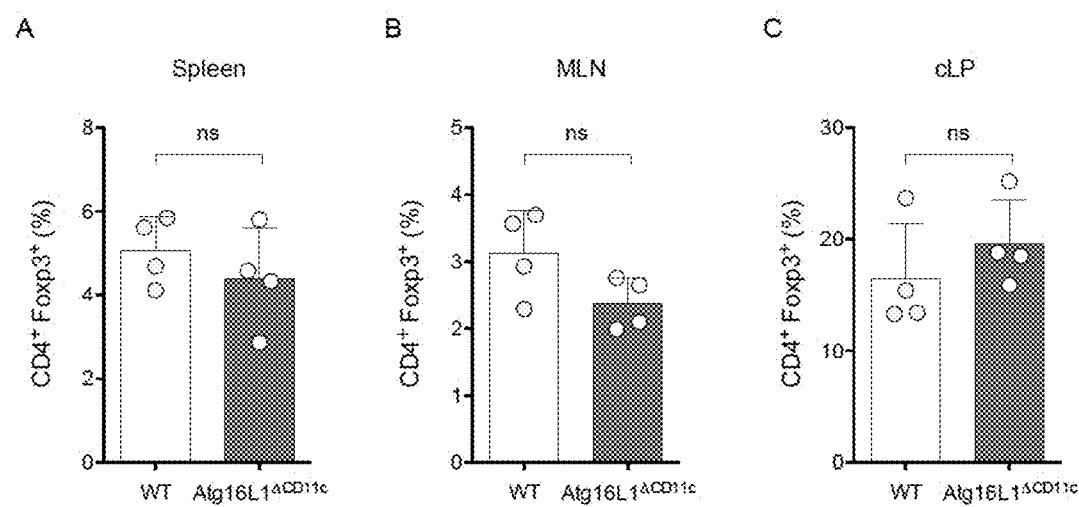
FIG. 11A-FIG. 11C is a series of bar graphs showing B. fragilis OMV-mediated protection is not due to an overall defect in T$_{reg}$ development in Atg16L1$^{ΔCD11c}$ mice under naïve conditions. Proportions of CD4$^+$Foxp3$^+$ T cells in (FIG. 11A) spleen, (FIG. 11B) MLNs and (FIG. 11C) cLP of WT and Atg16L1$^{ΔCD11c}$ naïve mice. Error bars represent S.E.M. ns, not significant. Data are representative of at least 2 independent experiments, with 3-5 mice/group.
Figures 12A, 12B:
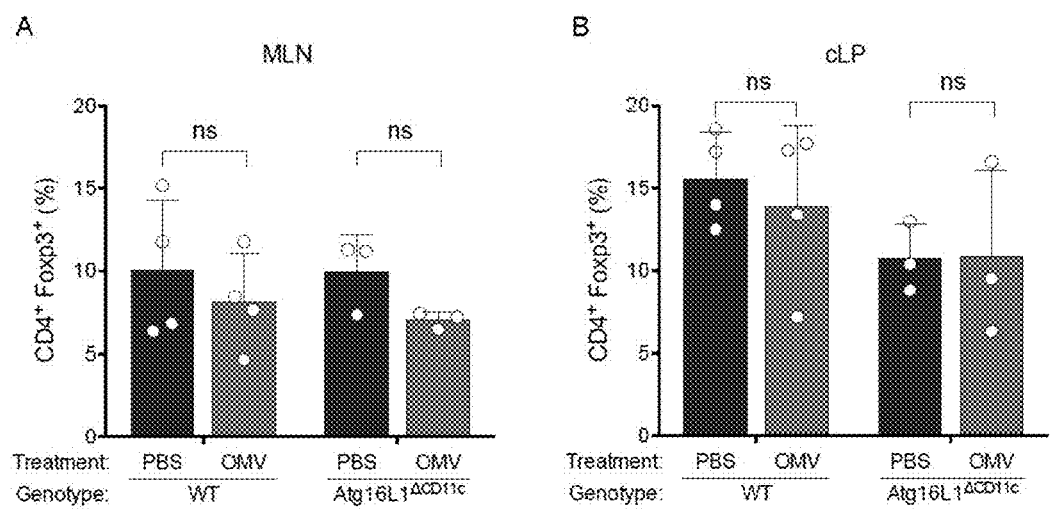
FIG. 12A-FIG. 12B is a series of bar graphs showing B. fragilis OMV-mediated protection is not due to an overall defect in T$_{reg}$ development in Atg16L1$^{ΔCD11c}$ mice during colitis. Proportions of CD4$^+$Foxp3$^+$ T cells in (FIG. 12A) MLNs and (FIG. 12B) cLP of WT and Atg16L1$^{ΔCD11c}$ mice orally treated with PBS or B. fragilis WT-OMV during DNBS colitis. Error bars represent S.E.M. ns, not significant. Data are representative of at least 3 independent experiments, with 3-5 mice/group.

As a CD-risk gene, the in vivo requirement for ATG16L1 in CD11c DCs during OMV-mediated protection from experimental colitis was investigated. Indeed, WT mice treated by oral gavage with WT-OMVs are protected from 2,4-dinitrobenzenesulfonic acid (DNBS) colitis, whereas Atg16L1$^{\Delta CD11c}$ mice exhibit acute weight loss and increased mortality similar to untreated mice (FIG. 9A and FIG. 10A). WT, but not Atg16L1$^{\Delta CD11c}$ mice, orally administered OMVs are protected from shortening of the colon, a hallmark of colitis models (FIG. 9B), with colitis scoring and cytokine profiles verifying protection from disease (FIG. 9C and FIG. 10B). Prevention of colitis is not due to an overall defect in T$_{reg}$ development in Atg16L1$^{\Delta CD11c}$ mice (FIG. 11). Further, while proportions of CD4$^+$Foxp3$^+$ cells are comparable in all groups of mice during colitis (FIG. 12), Atg16L1$^{\Delta CD11c}$ mice produce significantly less IL-10 from gut Foxp3$^+$ T$_{regs}$ compared to WT mice following WT-OMV treatment (FIG. 9D and FIG. 10C). Thus, WT-OMVs require ATG16L1 within DCs to induce IL-10 expression from Foxp3$^+$T$_{regs}$ and to suppress intestinal inflammation in a colitis model.

Figure 9E:
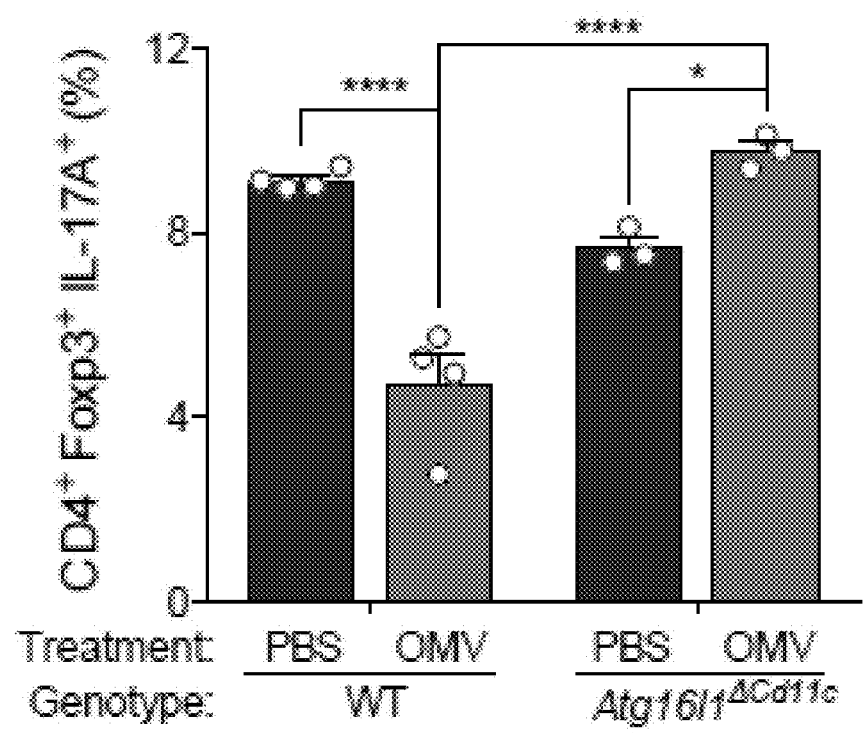
Figures 13A, 13B:
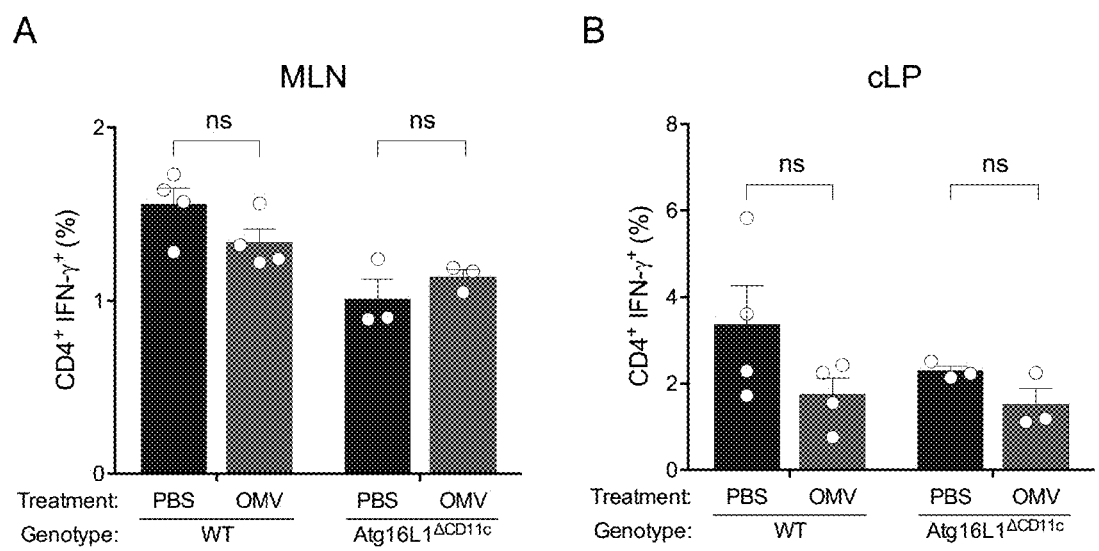
FIG. 13A-FIG. 13B is a series of bar graphs showing CD4$^+$IFN-γ$^+$ populations are not significantly altered by B. fragilis WT-OMV treatment during DNBS colitis.
Figures 14A, 14B:
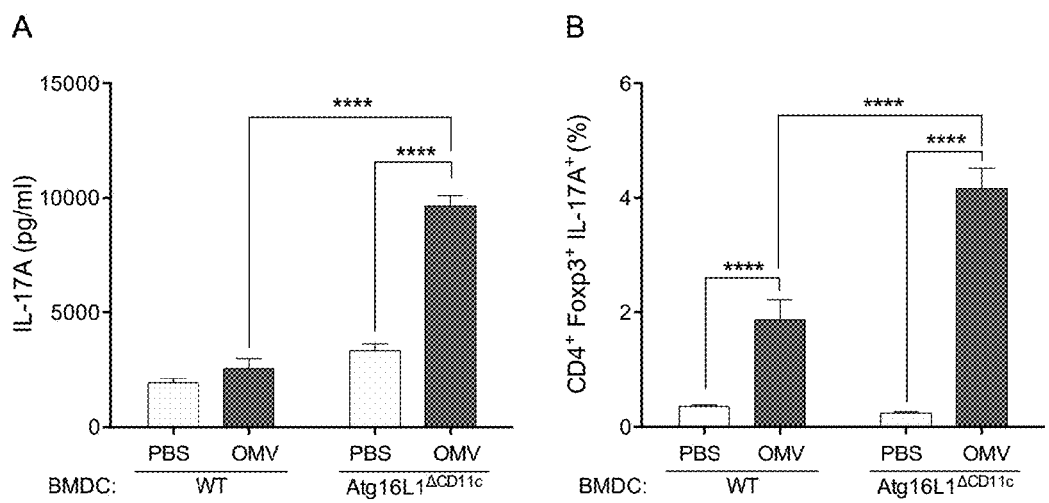
FIG. 14A-FIG. 14B is a series of bar graphs showing OMV treatment of Atg16L1$^{ΔCD11c}$ DCs promotes IL-17A production. In vitro DC-T cell co-cultures with WT or Atg16L1$^{ΔCD11c}$ DCs treated with PBS or B. fragilis WT-OMVs and analyzed for IL-17A by (FIG. 14A) ELISA and (FIG. 14B) ICCS among CD4$^+$Foxp3$^+$T$_{regs}$. Error bars represent S.E.M. **** p<0.0001. Data are representative of at least 3 independent experiments.
Figure 15A:
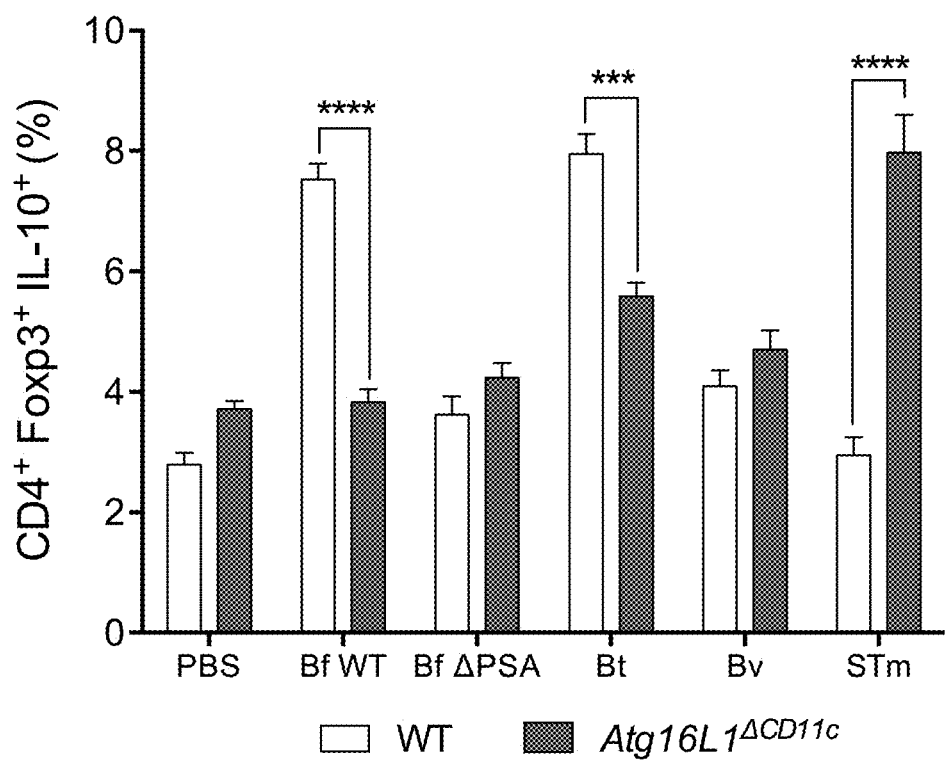
FIG. 15A-FIG. 15C is a series of bar graphs showing commensal and pathogen-derived OMVs differentially utilize ATG16L1 in CD11c$^+$ BMDCs. Frequency of (FIG. 15A) CD4$^+$Foxp3$^+$IL-10$^+$ T$_{regs}$, (FIG. 15B) CD4$^+$Foxp3$^+$IL-17A$^+$ T cells and (FIG. 15C) CD4$^+$IFN-γ$^+$ T cells from DC-T cell co-cultures with WT or Atg16L1$^{ΔCD11c}$ DCs treated with PBS, B. fragilis WT-OMV, ΔPSA-OMV, Bt-OMV, Bv-OMV, or S.Tm OMVs. Error bars represent S.E.M. * p<0.001, ** p<0.0001. Data are representative of 3 independent experiments. Bt, Bacteroides thetaiotamicron; By, Bacteroides vulgatus; STm, Salmonella enterica serovar Typhimurium.
Figure 15B:
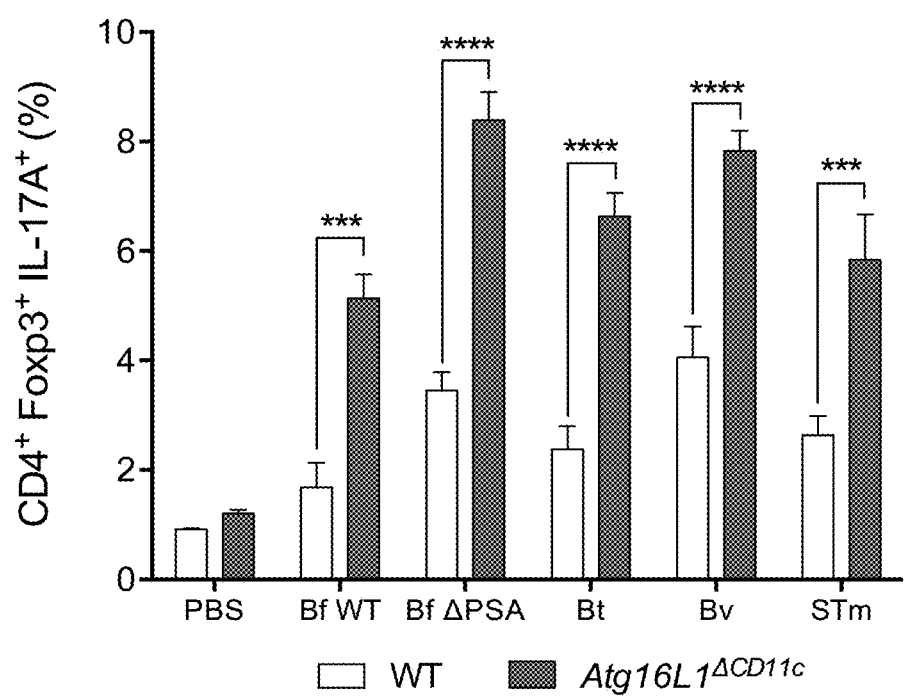
Figure 15C:
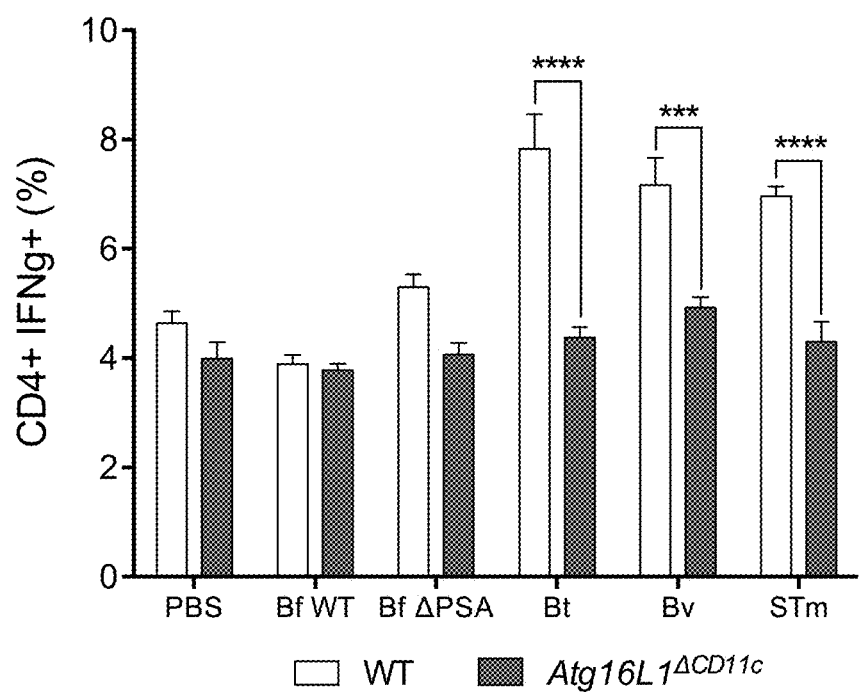
Figure 16A:
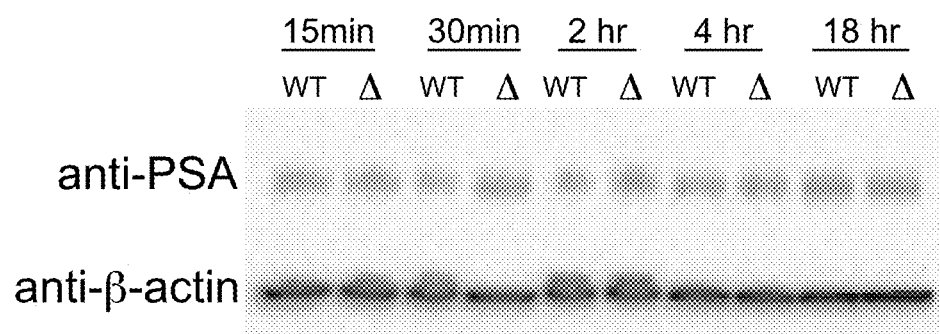
FIG. 16A-FIG. 16E is a series of western blot images and plots showing Atg16L1$^{ΔCD11c}$ DCs are not impaired in uptake of B. fragilis-labeled OMVs.
Figure 16B:
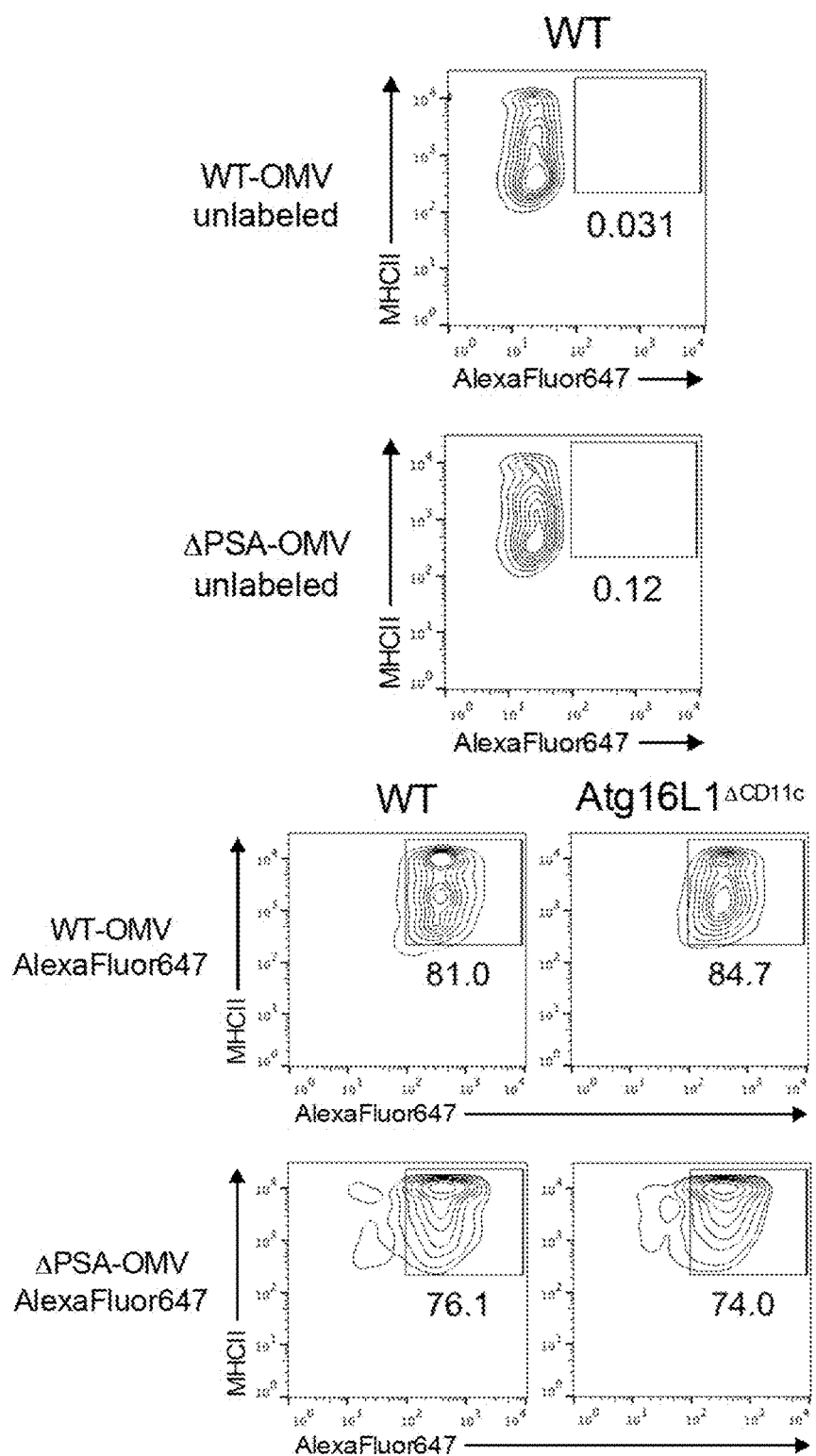
Figure 16C:
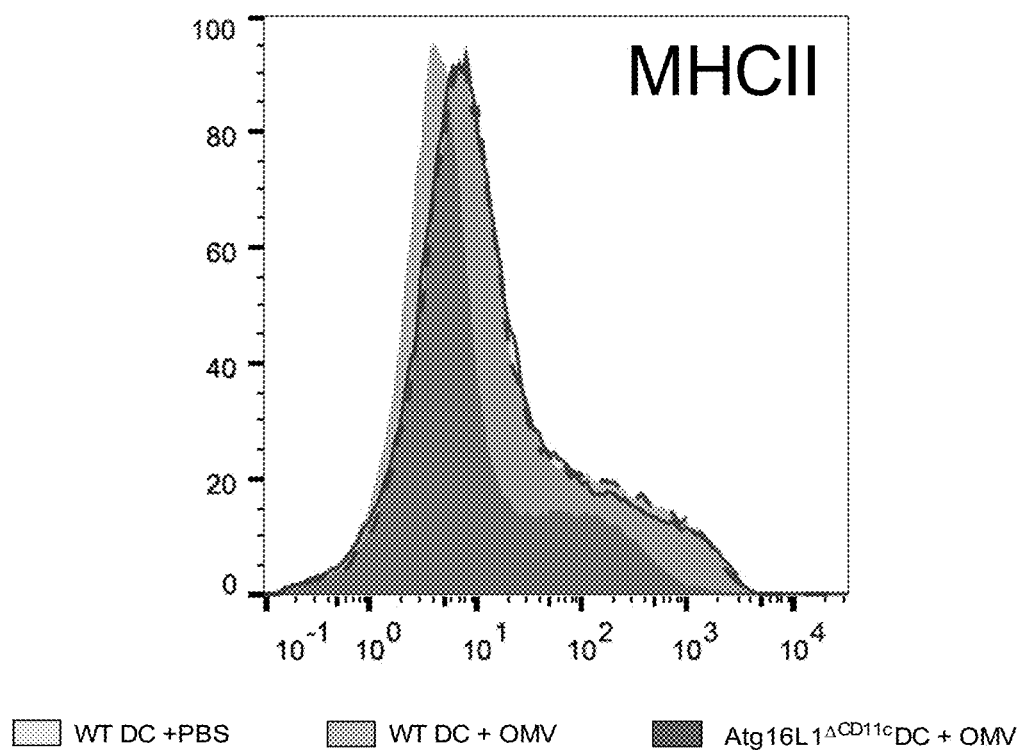
Figure 16D:
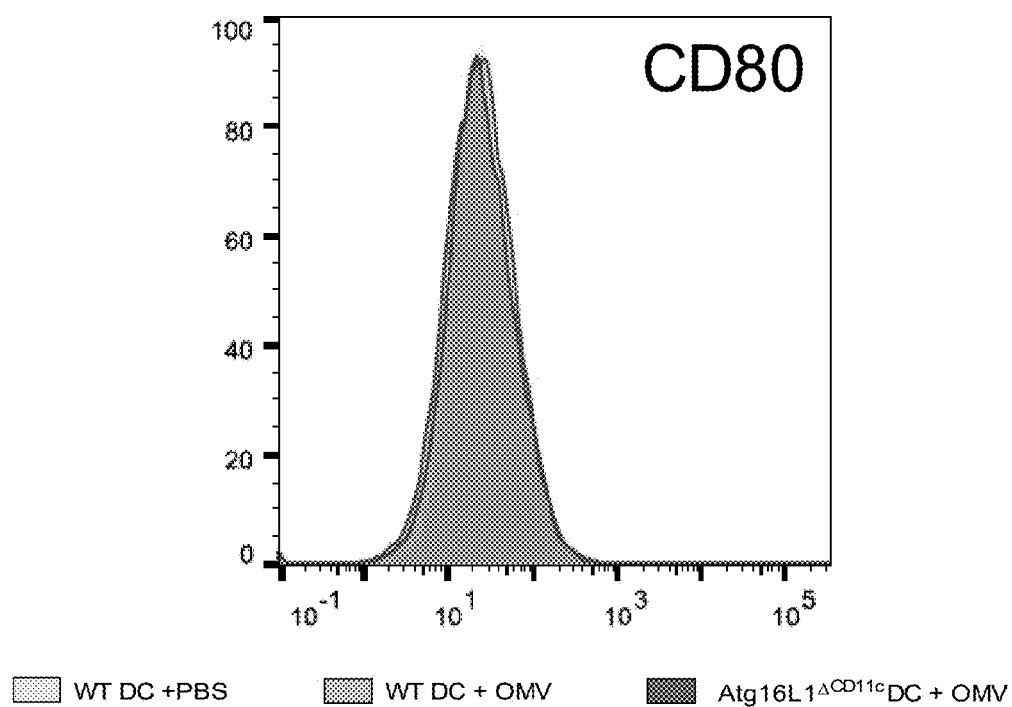
Figure 16E:
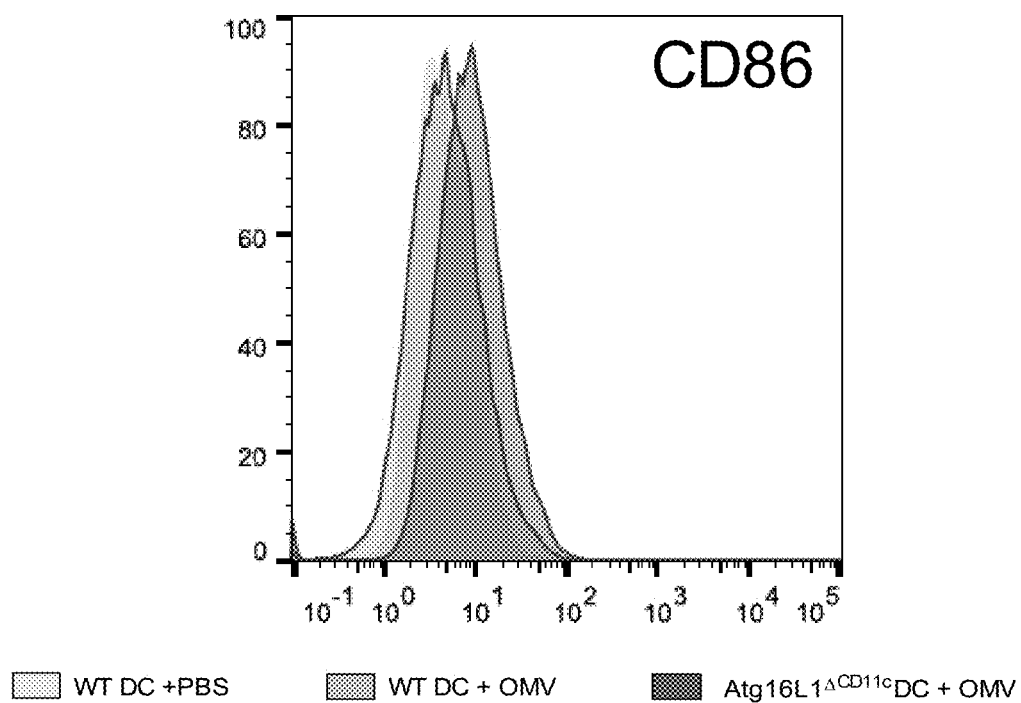

In addition to impaired IL-10 production in response to OMV treatment, Atg16L1$^{\Delta CD11c}$ mice display an increase in IL-17A expression (FIG. 9E), but not IFC-γ (FIG. 13), among mucosal CD4$^+$Foxp3$^+$ T cells during colitis. Further, in vitro co-cultures of OMV-pulsed Atg16L1$^{\Delta CD11c}$ BMDCs result in impaired IL-10 expression among T$_{regs}$ (FIG. 10), and increased IL-17A production in CD4$^+$Foxp3$^+$ T cells (FIG. 14). Interestingly, while OMVs from other enteric bacteria each elicited a unique ATG16L1-dependent immune profile, only *B. fragilis* OMVs exclusively induce an anti-inflammatory response (FIG. 15). Together, these data suggest ATG16L1-deficiency in DCs alters the quality of the T cell response to OMVs.

Figures 17A, 17B, 17C:
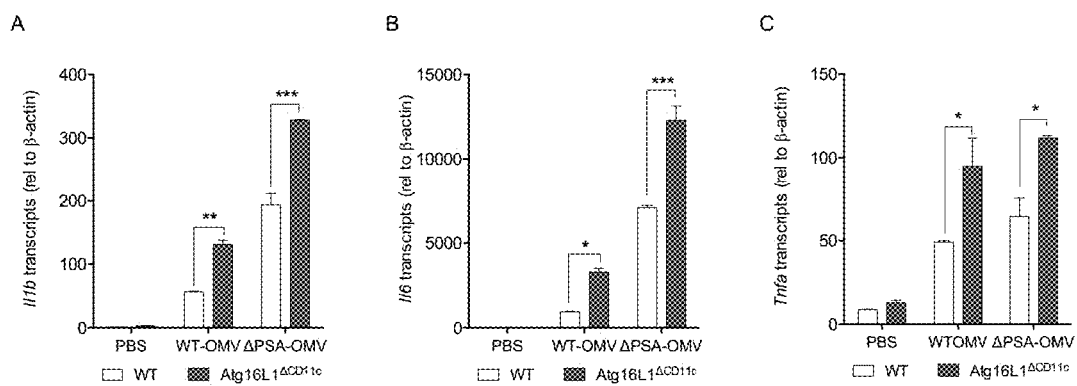
FIG. 17A-FIG. 17C is a series of bar graphs showing Atg16L1$^{ΔCD11c}$ DCs display a hyper-inflammatory cytokine profile. Quantitative RT-PCR of (FIG. 17A) Il1b, (FIG. 17B) Il6, and (FIG. 17C) Tnfa in WT or Atg16L1$^{ΔCD11c}$ BMDCs treated with PBS, WT-OMV or ΔPSA-OMV, relative to the β-actin. Error bars represent S.E.M. * p<0.05,  p<0.01, and * p<0.001. Data are representative of at least 4 independent experiments.

As DCs coordinate adaptive immunity, it was sought to determine how Atg16L1$^{\Delta CD11c}$ DCs are impaired in promoting tolerogenic responses. Following OMV stimulation, no differences were observed by WT or Atg16L1$^{\Delta CD11c}$ DCs in internalizing OMVs, or in surface expression of MHC II, CD80 and CD86 (FIG. 16). However, stimulation with OMVs results in an increase transcription of multiple pro-inflammatory cytokines in Atg16L1$^{\Delta CD11c}$ DCs compared to WT cells (FIG. 17). These data are consistent with previous reports of a hyper-inflammatory response in ATG16L1-deficient macrophages and DCs stimulated with other microbial ligands (24, 26). Abrogation of T$_{reg}$ responses by ATG16L1-deficient DCs is likely due to increased pro-inflammatory cytokine production, which may impair DC-T cell interactions. Atg16L1$^{\Delta CD11c}$ mice do not display more severe colitis than WT mice in the absence of OMV treatment (FIG. 9), suggesting that lack of protection is not due to more fulminant inflammation, but rather an inability to induce T$_{regs}$ in mice deficient in ATG16L1 among CD11c$^+$ DCs.

Figure 18A:
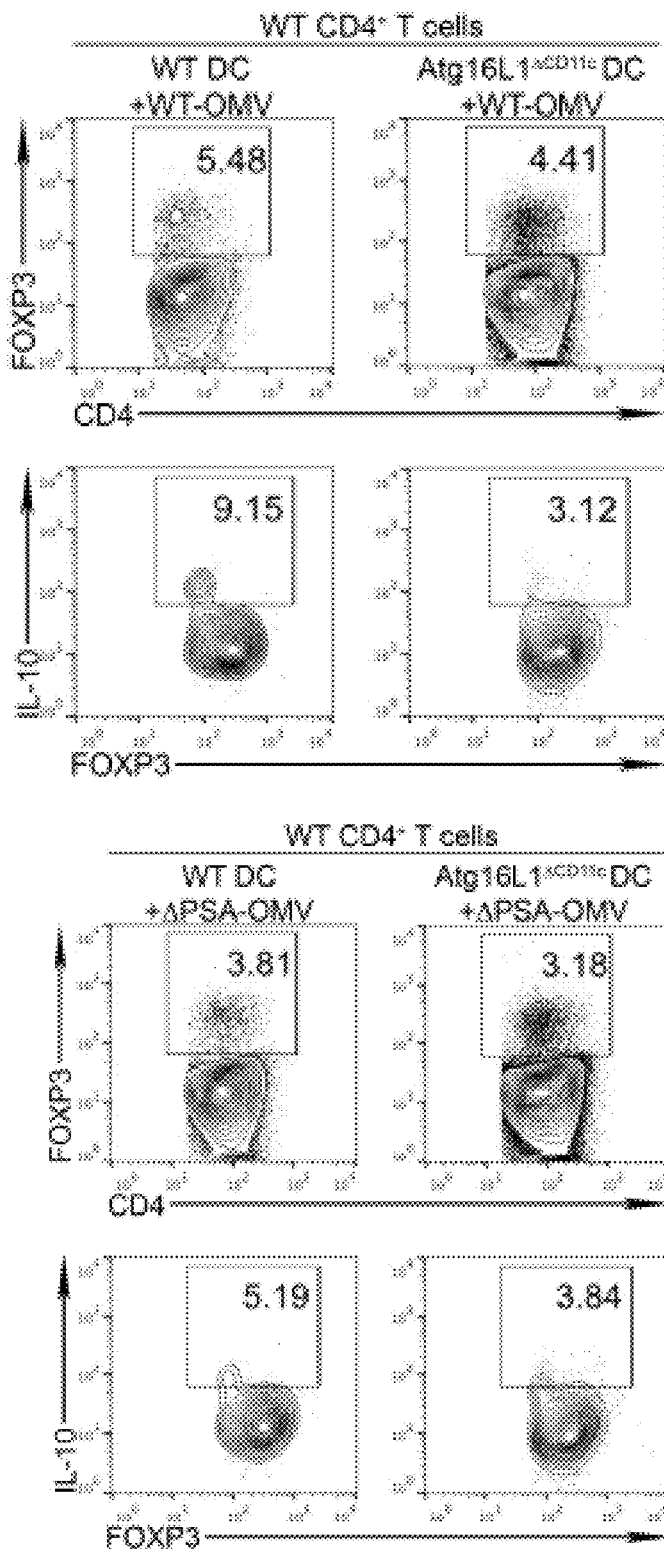
Figure 18C:
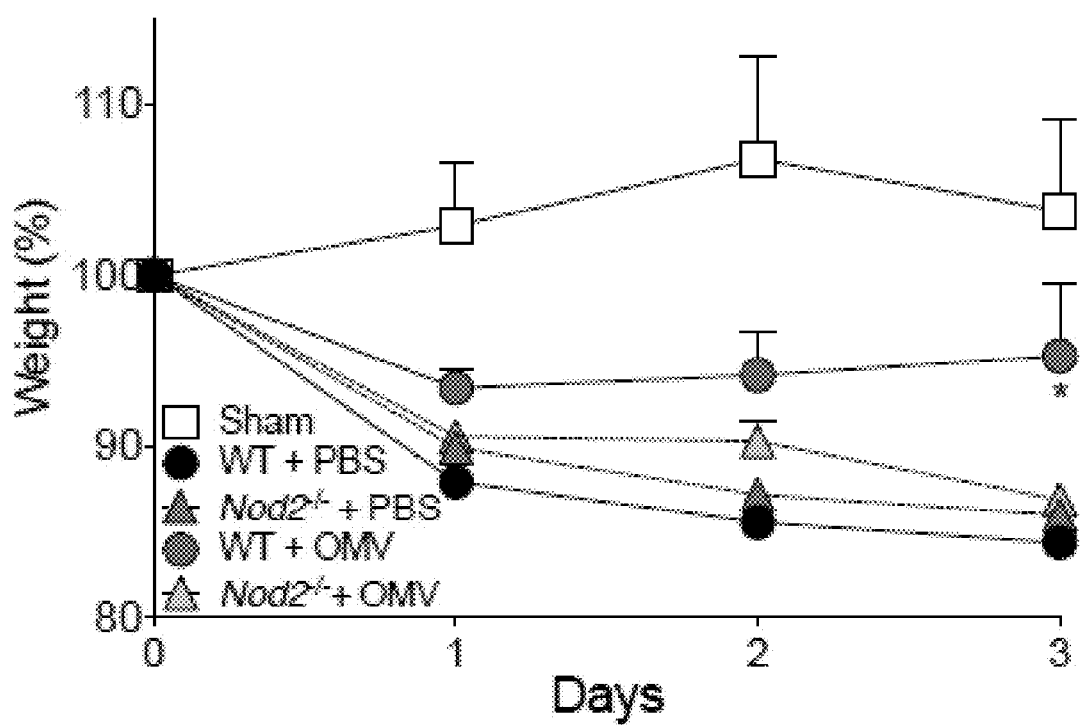
Figure 18D:
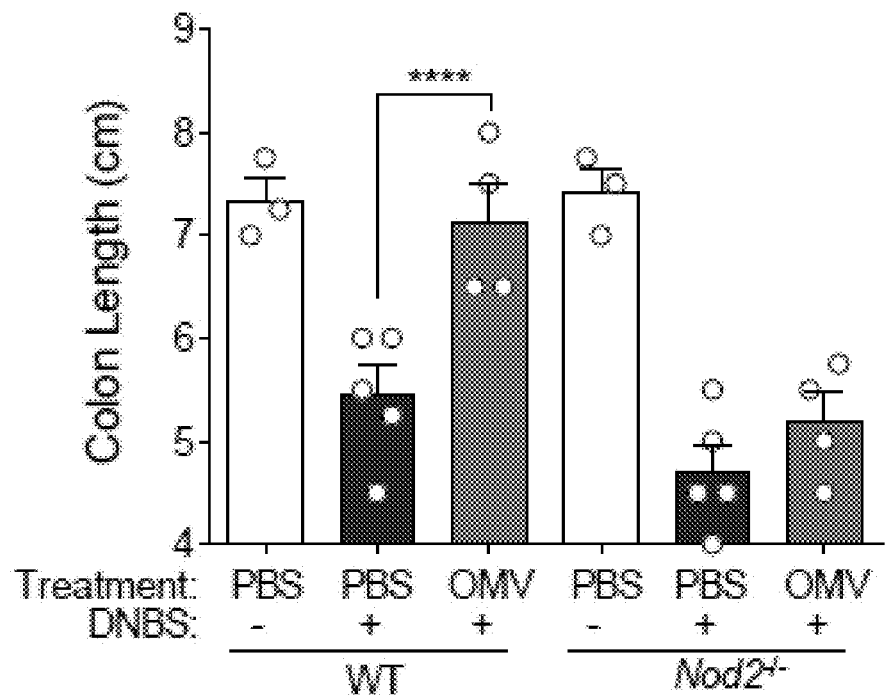
Figure 18D:
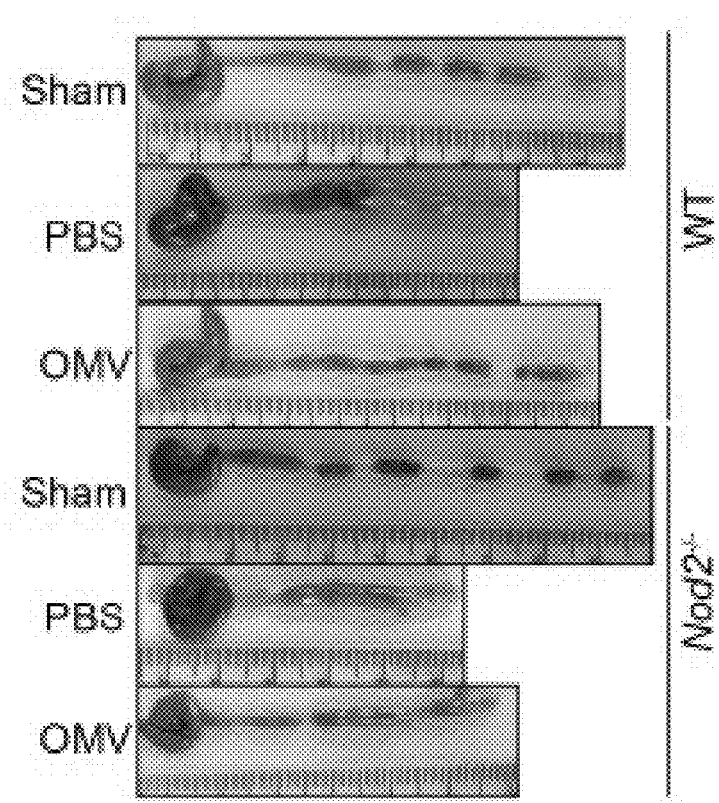
Figures 19A, 19B:
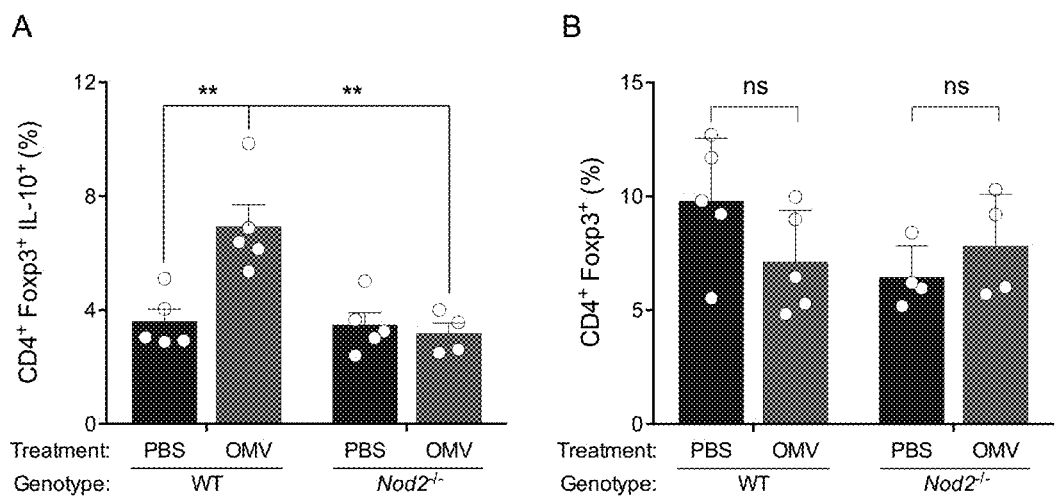
FIG. 19A-FIG. 19B is a series of bar graphs showing induction of CD4$^+$Foxp3$^+$IL-10$^+$ T$_{regs}$ in the colon during colitis is impaired in Nod2$^{-/-}$ mice.
Figure 20:
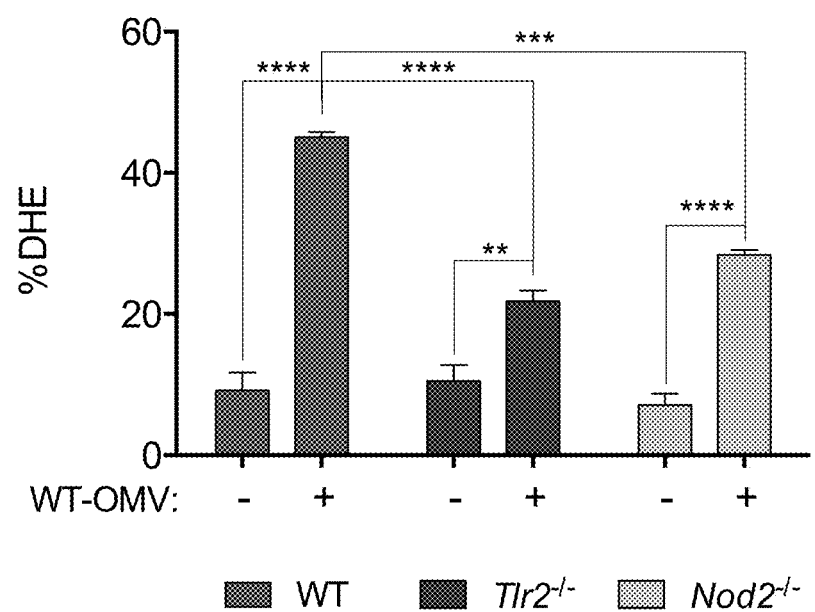
FIG. 20 is a bar graph showing TLR2 and NOD2 are involved in OMV-mediated induction of reactive nitrogen species (ROS), a feature of LAP. WT, Tlr2$^{-/-}$, or Nod2$^{-/-}$ BMDCs were pulsed with WT-OMVs for 2 h and ROS production was assessed by dihydroethidium (DHE), as measured for flow cytometry. Error bars represent S.E.M.  $p<0.01$, * $p<0.001$, **** $p<0.0001$. Data are representative of 3 independent experiments.

NOD2 encodes for an intracellular sensor of bacterial peptidoglycan, and polymorphisms in this gene contribute to the largest fraction of genetic risk for CD. NOD2 has been shown to physically recruit ATG16L1, a process that is impaired in human cells homozygous for a NOD2 frameshift mutation (20). Accordingly, Nod2$^{-/-}$ BMDCs pulsed with WT-OMVs are unable to support IL-10 production from Foxp3$^+$ T$_{regs}$ during in vitro co-cultures (FIG. 18A and FIG. 18B), revealing a crucial role for NOD2 signaling in microbiome-mediated immune tolerance. This notion is supported with in vivo studies showing that Nod2$^{-/-}$ mice are not protected from colitis by WT-OMV treatment (FIG. 18C and FIG. 18D). Similar to Atg16L1$^{\Delta CD11c}$ animals, Nod2$^{-/-}$ mice produce significantly less IL-10 from Foxp3$^+$ T$_{regs}$ of the MLN following WT-OMV treatment (FIG. 19A), while proportions of T$_{regs}$ remain unchanged during DNBS colitis (FIG. 19B). Previous studies have shown that Toll-like receptor 2 (TLR2) is required for the PSA response (33, 37). While the role of NOD2 in inducing LAP is currently unknown, signaling through TLR2 potently activates LAP. *B. fragilis* OMVs induce reactive oxygen species (ROS) from WT DCs, a known product of LAP activation (36), but at significantly reduced levels in Nod2$^{-/-}$ or Tlr2$^{-/-}$ DCs (FIG. 20). Though further studies are needed to define the mechanism of LAP activation by OMVs, these data reveal that NOD2 and ATG16L1 may cooperate as part of a common pathway to promote anti-inflammatory immune responses to the microbiome.

Figure 21A:
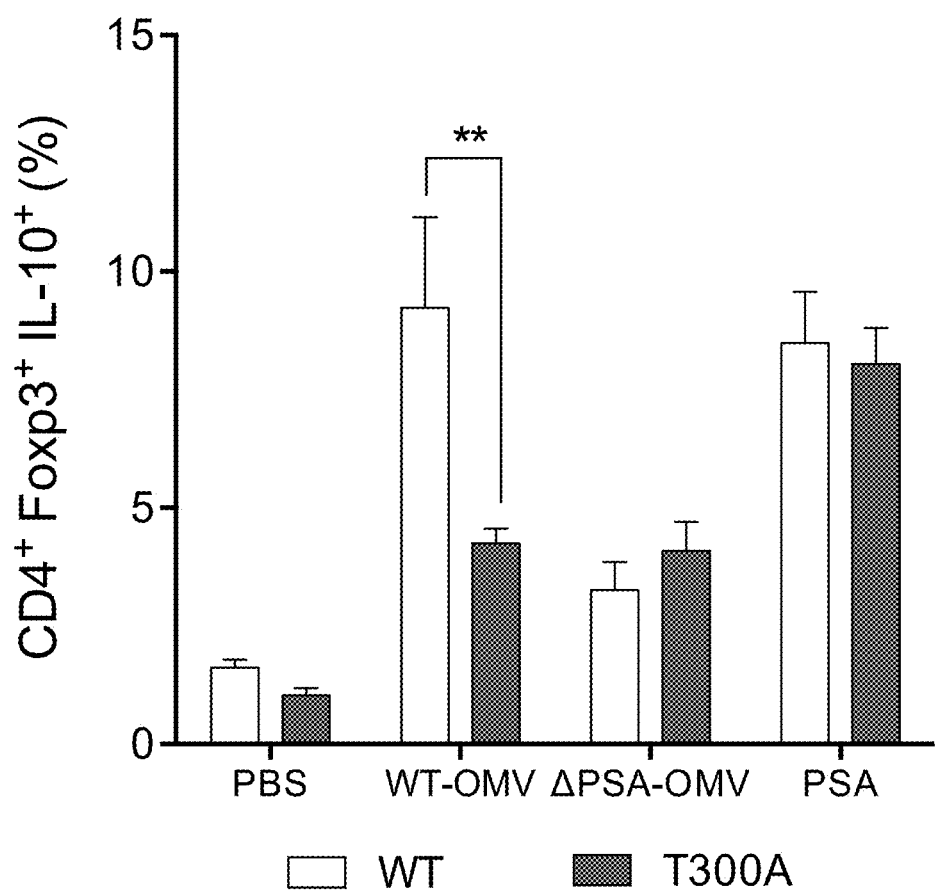
FIG. 21A-FIG. 21B is a series of bar graphs, line and scatter plots, images, and histology images showing ATG16L1 T300A transgenic mice are not protected from colitis by *B. fragilis* OMVs.
Figure 21B:
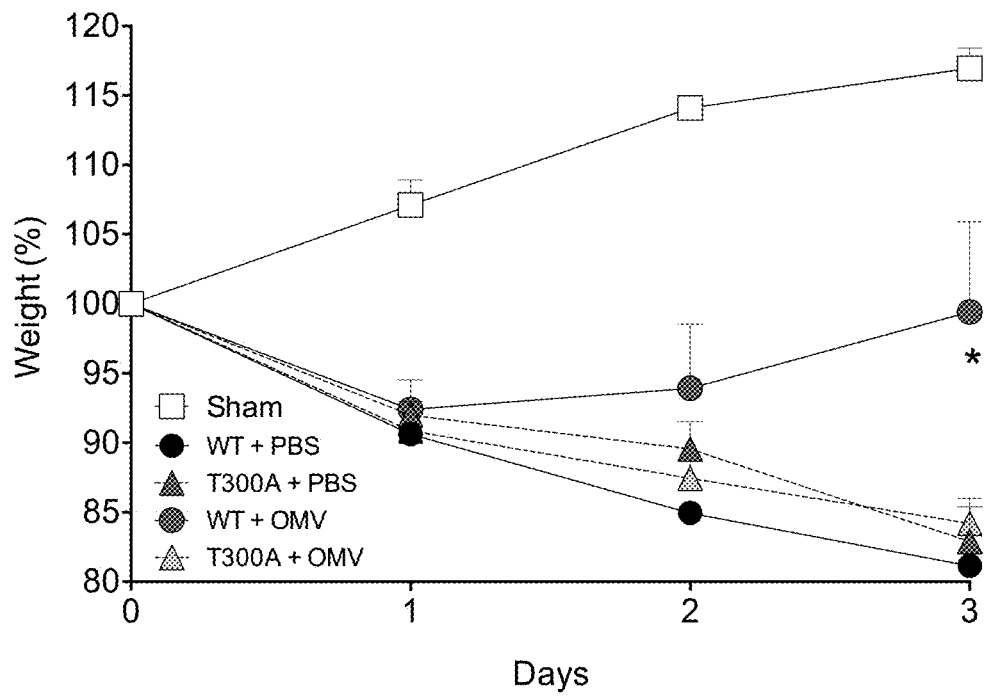
Figure 21B:
Figure 21C:
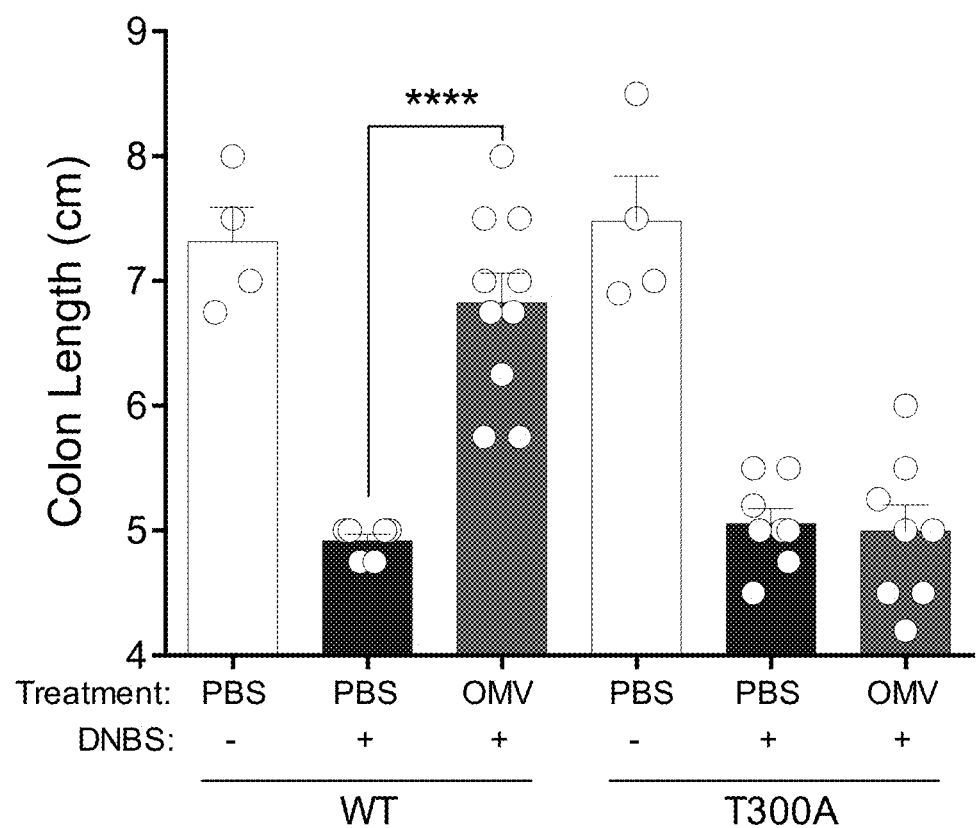
Figure 21D:
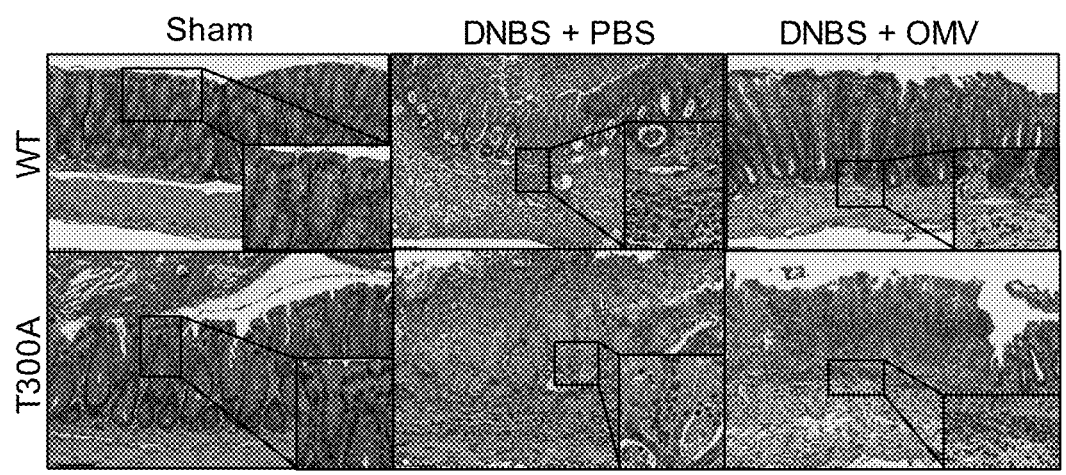
Figure 21E:
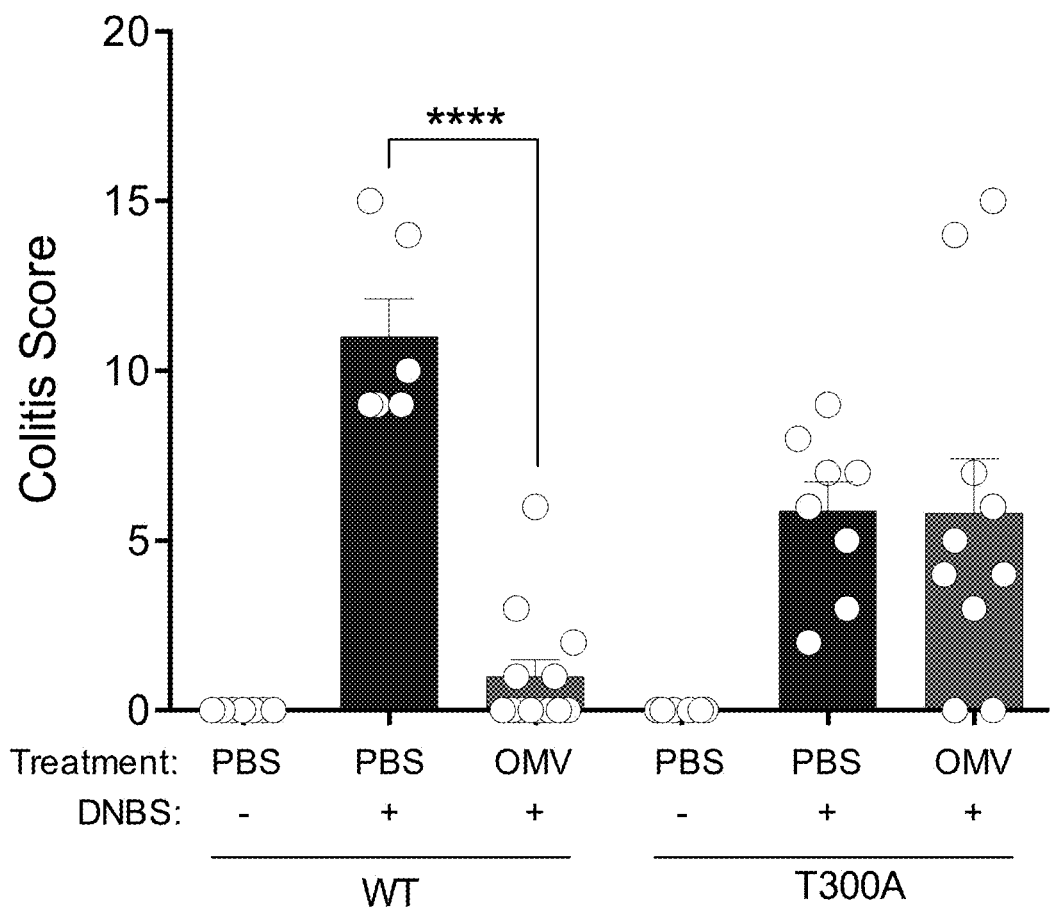
Figure 21F:
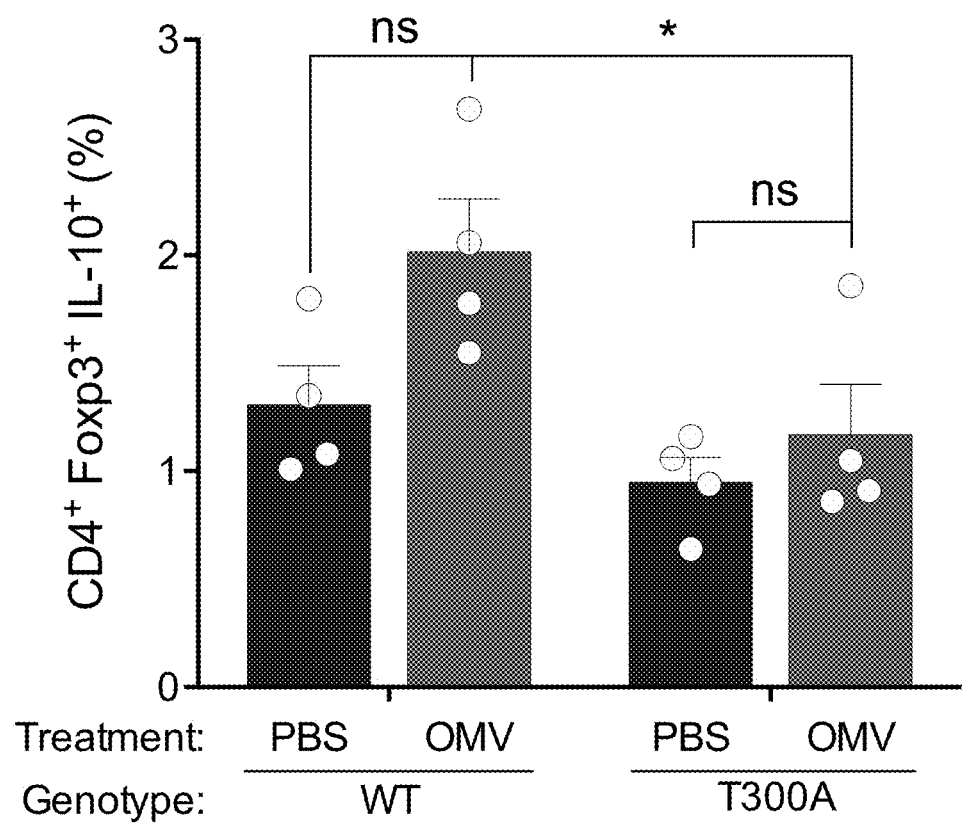
Figure 21G:
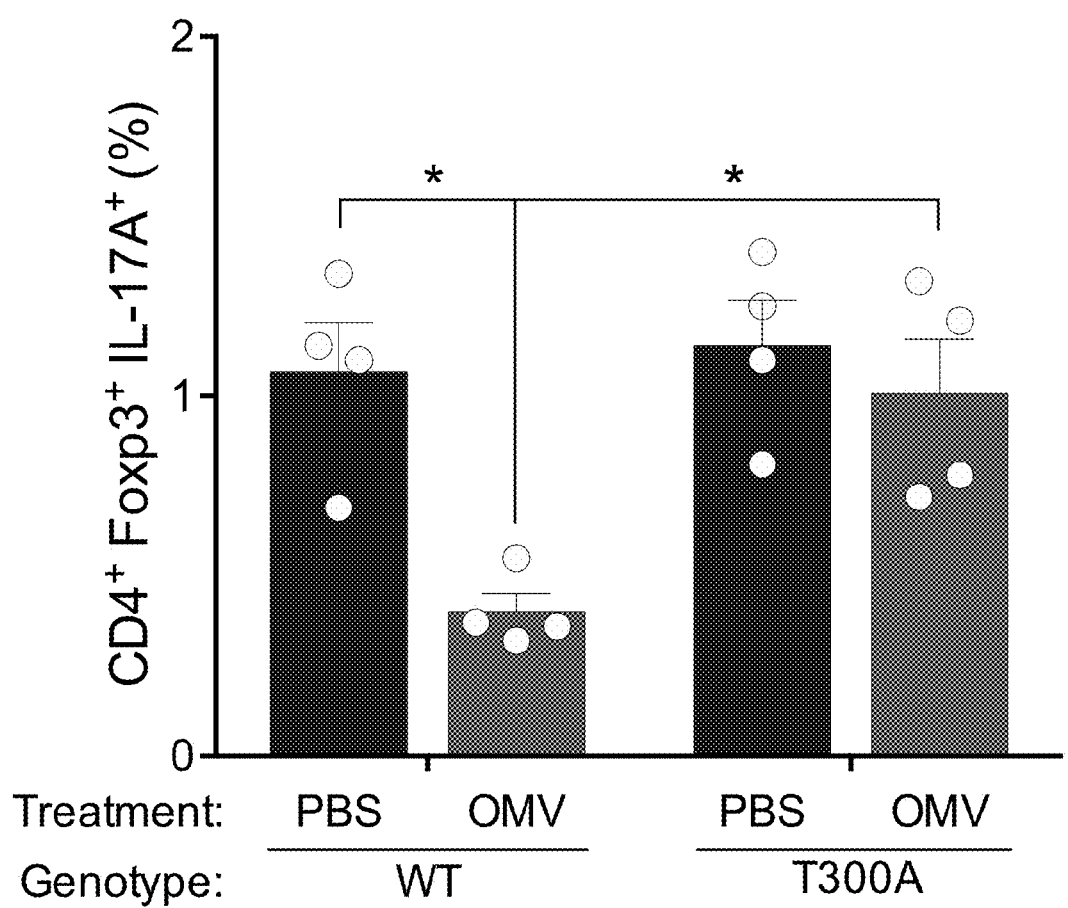
Figure 22A:
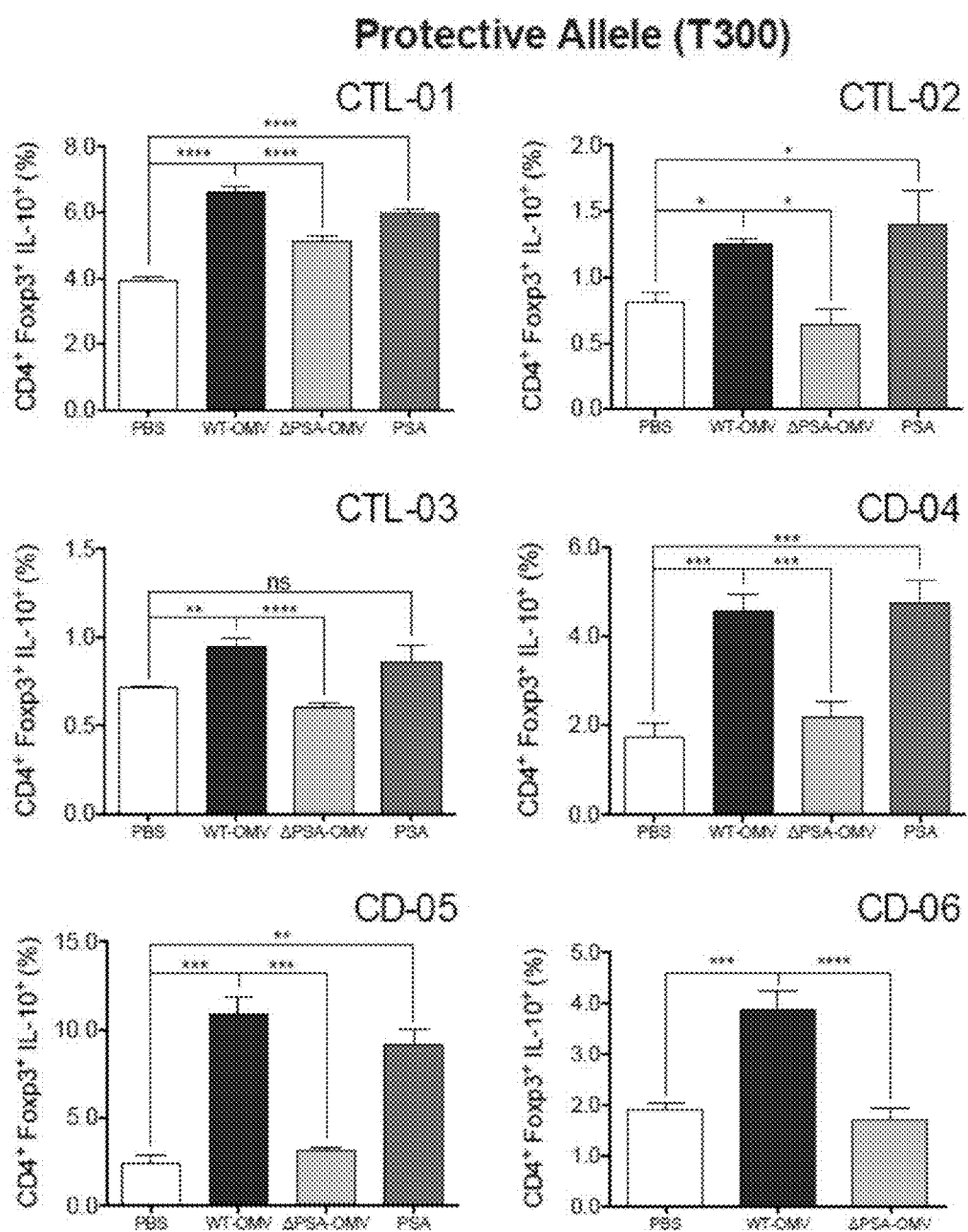
FIG. 22A-FIG. 22B is a series of bar graphs showing the T300A risk variant of ATG16L1 in human cells is unable to support OMV responses.
Figure 22B:
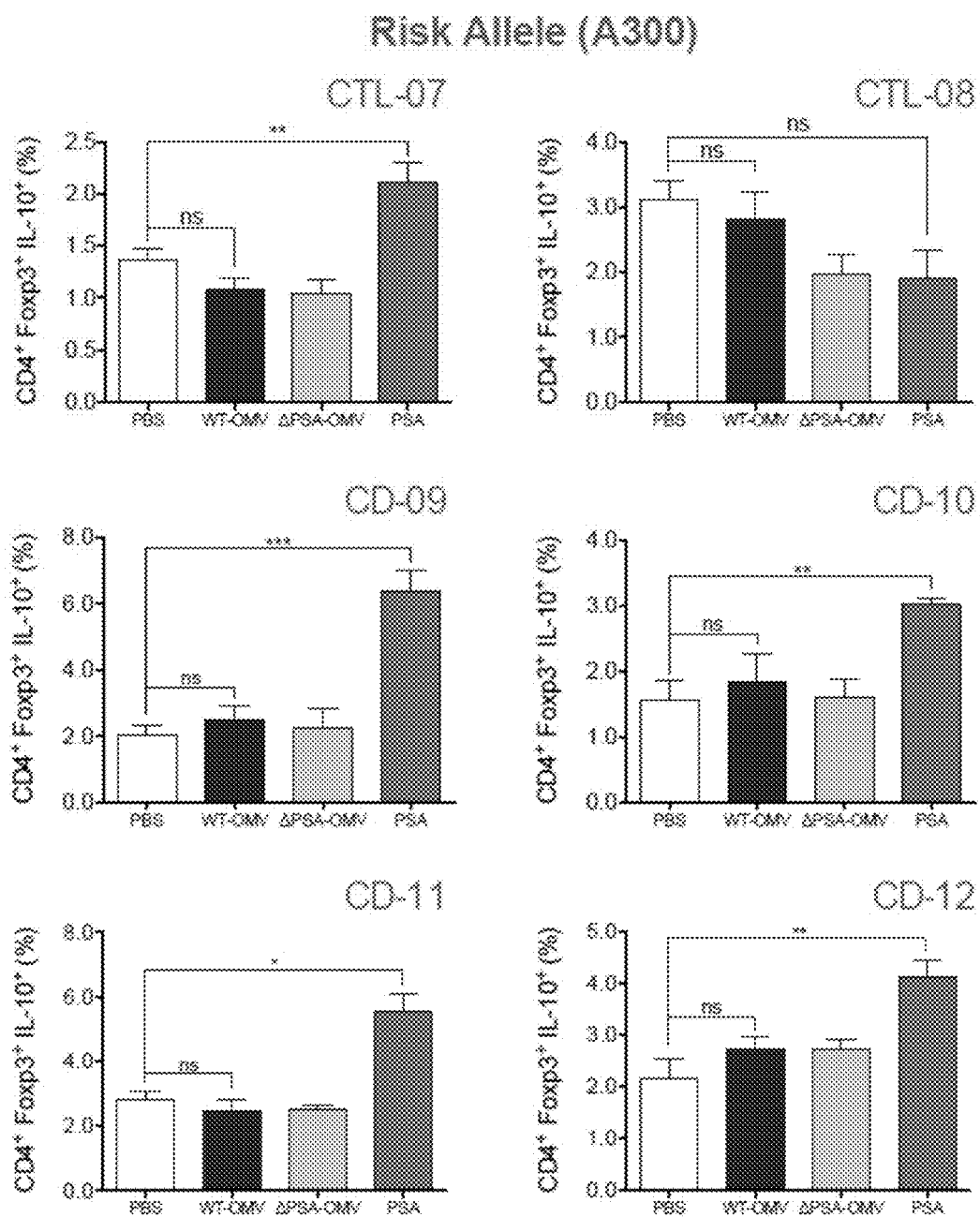

To extend and validate gene deletion approaches, responses to OMVs by immune cells carrying the CD-associated variant of ATG16L1 were tested. The ATG16L1 T300A variant leads to protein instability and altered cellular responses. BMDCs from transgenic mice expressing the T300A allele are also unable to promote IL-10 expression from Foxp3$^+$T$_{regs}$ in response to WT-OMVs (FIG. 21A). Further, ATG16L1 T300A transgenic mice are not protected from DNBS colitis and do not mount a potent T$_{reg}$ response when administered WT-OMV compared to WT mice (FIG. 21B to FIG. 21F). These findings prompted us to investigate if human immune cells from CD patients with the ATG16L1 T300A risk variant (TABLE 1) are also defective in promoting Foxp3$^+$ T$_{reg}$ development by *B. fragilis* OMVs. Monocyte-derived dendritic cells (MoDC) from CD patients and healthy controls harboring either the protective allele (T300) or the risk allele (T300A) were pulsed with OMVs or PSA and co-cultured with syngeneic CD4$^+$ T cells. Consistent with the mouse data, human cells homozygous for the risk allele are unable to support induction of IL-10 from Foxp3$^+$ T$_{regs}$ by WT-OMVs compared to MoDCs carrying the protective allele (FIG. 22). Remarkably, all samples tested display the predicted outcome based on genotype, and not disease status. However, cells from most subjects, regardless of genotype, respond to purified PSA (FIG. 22). Collectively, it was concluded that mouse and human DCs require functional ATG16L1 for induction of CD4$^+$Foxp3$^+$IL-10$^+$ T$_{regs}$ in response to *B. fragilis* OMVs.

In summary, the above example describes the interactions between genetic (ATG16L1/NOD2) and environmental (microbiome) factors cooperating to promote beneficial immune responses. *B. fragilis* OMVs utilize LAP, an ATG16L1-dependent cellular trafficking and signaling pathway, to induce mucosal tolerance. The hyper-inflammatory responses that occur with mutations in ATG16L1 likely alter antigen-processing pathways and impair signaling by DCs to T cells, and may explain why CD-associated polymorphisms abrogate T$_{reg}$ induction by OMVs. Collectively, discovery of genetic circuits co-opted by the microbiome to engender health provides unprecedented functional insights into gene-environment interaction relevant to the pathogenesis of IBD. Here, is proposed an additional role for genes previously implicated in killing bacteria—namely, mutations in genetic pathways linked to IBD result in an inability to sense and/or respond to beneficial microbes. This hypothesis may represent a new perspective for the etiology of microbiome-related diseases.

Example 3: Treatment

The following example describes treatment methods for patients with a defective capacity to generate Treg cells.

Patients with a defective capacity to generate Treg cells will be treated with small molecules that restore the Atg gene-dependent process of Treg generation identified and proven to be relevant to human disease, as described herein. The treatment will induce upregulation of Atg-gene-dependent presentation of commensal microbe materials to Tregs to increase those secreting IL10 or other anti-inflammatory molecules or changing the expression of co-stimulatory molecules involved in Treg generation.

Example 4: Screening

The following example describes a screening method for small molecule therapeutics.

Screening for small molecules with (i) targeting the Atg gene-dependent process of presentation of bacterial pathogen associated molecular patterns (as embodied by PSA herein) to Treg cells to optimize the production of immunoregulatory Treg cells or screening for small molecules with (ii) targeting the specific genes identified herein as essential to this process such as for example Rubicon, Atg16L1 (including the disease-related mutation Atg16L1T300A), Atg7, and Atg5 with small molecules to optimize their function in this pathway.

Such screens would involve co-culture of wild type or Atg gene-mutant dendritic cells or ATG16L1-deficient macrophages with Treg precursors (e.g, CD4+ T cells, BMDCs) as described in (H. Chu et al., Science 10.1126/science.aad9948 (2016)) and analysis of the number and cytokine secretion properties of Tregs (H. Chu et al., Science 10.1126/science.aad9948 (2016)). Such screens would involve fragment screens for chemical moieties that interact with purified proteins involve in Treg generation and evaluation of their effects, or the effects of combinations of such moieties on Treg induction.

REFERENCES

1. D. A. Peterson, D. N. Frank, N. R. Pace, J. I. Gordon, Metagenomic approaches for defining the pathogenesis of inflammatory bowel diseases. Cell Host Microbe 3, 417-427 (2008); published online Epub June 12.
2. D. A. Hill, D. Artis, Intestinal bacteria and the regulation of immune cell homeostasis. Annu Rev Immunol 28, 623-667 (2010)10.1146/annurev-immunol-030409-101330).
3. K. Honda, D. R. Littman, The microbiome in infectious disease and inflammation. Annu Rev Immunol 30, 759-795 (2012)10.1146/annurev-immunol-020711-074937).
4. E. M. Brown, M. Sadarangani, B. B. Finlay, The role of the immune system in governing host-microbe interactions in the intestine. Nat Immunol 14, 660-667 (2013); published online Epub July (10.1038/ni.2611).
5. Y. Belkaid, T. W. Hand, Role of the microbiota in immunity and inflammation. Cell 157, 121-141 (2014); published online Epub March 27 (10.1016/j.cell.2014.03.011).
6. L. V. Hooper, D. R. Littman, A. J. Macpherson, Interactions between the microbiota and the immune system. Science 336, 1268-1273 (2012); published online Epub June 8 (10.1126/science.1223490).
7. S. R. Brant, Update on the heritability of inflammatory bowel disease: the importance of twin studies. Inflamm Bowel Dis 17, 1-5 (2011); published online Epub January (10.1002/ibd.21385).
8. M. Orholm, V. Binder, T. I. Sorensen, L. P. Rasmussen, K. O. Kyvik, Concordance of inflammatory bowel disease among Danish twins. Results of a nationwide study. Scandinavian journal of gastroenterology 35, 1075-1081 (2000); published online Epub October.
9. J. Halfvarson, L. Bodin, C. Tysk, E. Lindberg, G. Jarnerot, Inflammatory bowel disease in a Swedish twin cohort: a long-term follow-up of concordance and clinical characteristics. Gastroenterology 124, 1767-1773 (2003); published online Epub June.
10. C. Tysk, E. Lindberg, G. Jarnerot, B. Floderus-Myrhed, Ulcerative colitis and Crohn's disease in an unselected population of monozygotic and dizygotic twins. A study of heritability and the influence of smoking. Gut 29, 990-996 (1988); published online Epub July.
11. L. Jostins, S. Ripke, R. K. Weersma, R. H. Duerr, D. P. McGovern, K. Y. Hui et al., Host-microbe interactions have shaped the genetic architecture of inflammatory bowel disease. Nature 491, 119-124 (2012).
12. M. Wlodarska, A. D. Kostic, R. J. Xavier, An integrative view of microbiome-host interactions in inflammatory bowel diseases. Cell Host Microbe 17, 577-591 (2015); published online Epub May 13 (10.1016/j.chom.2015.04.008).
13. J. Hampe, A. Franke, P. Rosenstiel, A. Till, M. Teuber, K. Huse et al., A genome-wide association scan of non-synonymous SNPs identifies a susceptibility variant for Crohn disease in ATG16L1. Nat Genet 39, 207-211 (2007); published online Epub February (ng1954 [pii] 10.1038/ng1954).
14. J. D. Rioux, R. J. Xavier, K. D. Taylor, M. S. Silverberg, P. Goyette, A. Huett et al., Genome-wide association study identifies new susceptibility loci for Crohn disease and implicates autophagy in disease pathogenesis. Nat Genet 39, 596-604 (2007); published online Epub May (ng2032 [pii] 10.1038/ng2032).
15. M. Parkes, J. C. Barrett, N. J. Prescott, M. Tremelling, C. A. Anderson, S. A. Fisher et al., Sequence variants in the autophagy gene IRGM and multiple other replicating loci contribute to Crohn's disease susceptibility. Nat Genet 39, 830-832 (2007); published online Epub July (ng2061 [pii] 10.1038/ng2061).
16. A. Gardet, R. J. Xavier, Common alleles that influence autophagy and the risk for inflammatory bowel disease. Curr Opin Immunol 24, 522-529 (2012); published online Epub October (S0952-7915(12)00124-0 [pii] 10.1016/j.coi.2012.08.001).
17. J. P. Hugot, M. Chamaillard, H. Zouali, S. Lesage, J. P. Cezard, J. Belaiche et al., Association of NOD2 leucine-rich repeat variants with susceptibility to Crohn's disease. Nature 411, 599-603 (2001); published online Epub May 31 (10.1038/3507910735079107 [pii]).
18. Y. Ogura, D. K. Bonen, N. Inohara, D. L. Nicolae, F. F. Chen, R. Ramos et al., A frameshift mutation in NOD2 associated with susceptibility to Crohn's disease. Nature 411, 603-606 (2001); published online Epub May 31 (10.1038/3507911435079114 [pii]).
19. K. S. Kobayashi, M. Chamaillard, Y. Ogura, O. Henegariu, N. Inohara, G. Nunez et al., Nod2-dependent regulation of innate and adaptive immunity in the intestinal tract. Science 307, 731-734 (2005); published online Epub February 4 (10.1126/science.1104911).
20. L. H. Travassos, L. A. Carneiro, M. Ramjeet, S. Hussey, Y. G. Kim, J. G. Magalhaes et al., Nod1 and Nod2 direct autophagy by recruiting ATG16L1 to the plasma membrane at the site of bacterial entry. Nat Immunol 11, 55-62 (2010); published online Epub January (ni.1823 [pii] 10.1038/ni.1823).
21. R. Cooney, J. Baker, O. Brain, B. Danis, T. Pichulik, P. Allan et al., NOD2 stimulation induces autophagy in dendritic cells influencing bacterial handling and antigen presentation. Nat Med 16, 90-97 (2010); published online Epub January (nm.2069 [pii] 10.1038/nm.2069).
22. A. Murthy, Y. Li, I. Peng, M. Reichelt, A. K. Katakam, R. Noubade et al., A Crohn's disease variant in Atg16l1 enhances its degradation by caspase 3. Nature 506, 456-462 (2014); published online Epub February 27 (10.1038/nature13044).
23. K. G. Lassen, P. Kuballa, K. L. Conway, K. K. Patel, C. E. Becker, J. M. Peloquin et al., Atg16L1 T300A variant decreases selective autophagy resulting in altered cytokine signaling and decreased antibacterial defense. Proc Natl Acad Sci USA 111, 7741-7746 (2014); published online Epub May 27 (10.1073/pnas.1407001111).
24. T. Saitoh, N. Fujita, M. H. Jang, S. Uematsu, B. G. Yang, T. Satoh et al., Loss of the autophagy protein Atg16L1 enhances endotoxin-induced IL-1beta production. Nature 456, 264-268 (2008); published online Epub November 13 (nature07383 [pii] 10.1038/nature07383).
25. K. Cadwell, K. K. Patel, N. S. Maloney, T. C. Liu, A. C. Ng, C. E. Storer et al., Virus-plus-susceptibility gene interaction determines Crohn's disease gene Atg16L1 phenotypes in intestine. Cell 141, 1135-1145 (2010); published online Epub June 25 (S0092-8674(10)00545-3 [pii] 10.1016/j.cell.2010.05.009).
26. V. M. Hubbard-Lucey, Y. Shono, K. Maurer, M. L. West, N. V. Singer, C. G. Ziegler et al., Autophagy gene Atg16L1 prevents lethal T cell alloreactivity mediated by dendritic cells. Immunity 41, 579-591 (2014); published online Epub October 16 (10.1016/j.immuni.2014.09.011).
27. S. Park, M. D. Buck, C. Desai, X. Zhang, E. Loginicheva, J. Martinez et al., Autophagy Genes Enhance Murine Gammaherpesvirus 68 Reactivation from Latency by Preventing Virus-Induced Systemic Inflammation. Cell Host Microbe 19, 91-101 (2016); published online Epub January 13 (10.1016/j.chom.2015.12.010).
28. Q. Lu, C. C. Yokoyama, J. W. Williams, M. T. Baldridge, X. Jin, B. DesRochers et al., Homeostatic Control of Innate Lung Inflammation by Vici Syndrome Gene Epg5 and Additional Autophagy Genes Promotes Influenza Pathogenesis. Cell Host Microbe 19, 102-113 (2016); published online Epub January 13 (10.1016/j.chom.2015.12.011).
29. J. M. Kimmey, J. P. Huynh, L. A. Weiss, S. Park, A. Kambal, J. Debnath et al., Unique role for ATG5 in neutrophil-mediated immunopathology during M. tuberculosis infection. Nature 528, 565-569 (2015); published online Epub December 24 (10.1038/nature16451).
30. S. K. Mazmanian, J. L. Round, D. L. Kasper, A microbial symbiosis factor prevents intestinal inflammatory disease. Nature 453, 620-625 (2008); published online Epub May 29 (nature07008 [pii] 10.1038/nature07008).
31. J. L. Round, S. K. Mazmanian, Inducible Foxp3+ regulatory T-cell development by a commensal bacterium of the intestinal microbiota. Proc Natl Acad Sci USA 107, 12204-12209 (2010); published online Epub July 6 (0909122107 [pii] 10.1073/pnas.0909122107).
32. S. E. Allan, R. Broady, S. Gregori, M. E. Himmel, N. Locke, M. G. Roncarolo et al., CD4+ T-regulatory cells: toward therapy for human diseases. Immunol Rev 223, 391-421 (2008); published online Epub June (IMR634 [pii] 10.1111/j.1600-065X.2008.00634.x).
33. Y. Shen, M. L. Giardino Torchia, G. W. Lawson, C. L. Karp, J. D. Ashwell, S. K. Mazmanian, Outer membrane vesicles of a human commensal mediate immune regulation and disease protection. Cell Host Microbe 12, 509-520 (2012); published online Epub October 18 (S1931-3128(12)00275-2 [pii]10.1016/j.chom.2012.08.004).
34. J. Wei, L. Long, K. Yang, C. Guy, S. Shrestha, Z. Chen et al., Autophagy enforces functional integrity of regulatory T cells by coupling environmental cues and metabolic homeostasis. Nat Immunol 17, 277-285 (2016); published online Epub March (10.1038/ni.3365).
35. A. M. Kabat, O. J. Harrison, T. Riffelmacher, A. E. Moghaddam, C. F. Pearson, A. Laing et al., The autophagy gene Atg16l1 differentially regulates Treg and TH2 cells to control intestinal inflammation. eLife 5, (2016); published online Epub February 24 (10.7554/eLife.12444).
36. J. Martinez, R. K. Malireddi, Q. Lu, L. D. Cunha, S. Pelletier, S. Gingras et al., Molecular characterization of LC3-associated phagocytosis reveals distinct roles for Rubicon, NOX2 and autophagy proteins. Nature cell biology 17, 893-906 (2015); published online Epub July (10.1038/ncb3192).
37. J. L. Round, S. M. Lee, J. Li, G. Tran, B. Jabri, T. A. Chatila et al., The Toll-like receptor 2 pathway establishes colonization by a commensal of the human microbiota. Science 332, 974-977 (2011); published online Epub May 20 (science.1206095 [pii]10.1126/science.1206095).
38. M. A. Sanjuan, C. P. Dillon, S. W. Tait, S. Moshiach, F. Dorsey, S. Connell et al., Toll-like receptor signalling in macrophages links the autophagy pathway to phagocytosis. Nature 450, 1253-1257 (2007); published online Epub December 20 (nature06421 [pii]10.1038/nature06421).
39. C. Wellcome Trust Case Control, Genome-wide association study of 14,000 cases of seven common diseases and 3,000 shared controls. Nature 447, 661-678 (2007); published online Epub June 7 (10.1038/nature05911).
40. C. D. Packey, R. B. Sartor, Commensal bacteria, traditional and opportunistic pathogens, dysbiosis and bacterial killing in inflammatory bowel diseases. Curr Opin Infect Dis 22, 292-301 (2009); published online Epub June.
41. N. A. Molodecky, I. S. Soon, D. M. Rabi, W. A. Ghali, M. Ferris, G. Chernoff et al., Increasing incidence and prevalence of the inflammatory bowel diseases with time, based on systematic review. Gastroenterology 142, 46-54 e42; quiz e30 (2012); published online Epub January (S0016-5085(11)01378-3 [pii]10.1053/j.gastro.2011.10.001).
42. N. A. Molodecky, I. S. Soon, D. M. Rabi, W. A. Ghali, M. Ferris, G. Chernoff, E. I. Benchimol, R. Panaccione, S. Ghosh, H. W. Barkema, G. G. Kaplan, Increasing incidence and prevalence of the inflammatory bowel diseases with time, based on systematic review. Gastroenterology 142, 46-54 e42; quiz e30 (2012); published online Epub January (S0016-5085(11)01378-3 [pii]10.1053/j.gastro.2011.10.001).
43. L. V. Hooper, D. R. Littman, A. J. Macpherson, Interactions between the microbiota and the immune system. Science 336, 1268-1273 (2012); published online Epub June 8 (10.1126/science.1223490).
44. J. L. Round, S. K. Mazmanian, The gut microbiota shapes intestinal immune responses during health and disease. Nat Rev Immunol 9, 313-323 (2009); published online Epub May (nri2515 [pii]10.1038/nri2515).
45. S. Hwang, N. S. Maloney, M. W. Bruinsma, G. Goel, E. Duan, L. Zhang, B. Shrestha, M. S. Diamond, A. Dani, S. V. Sosnovtsev, K. Y. Green, C. Lopez-Otin, R. J. Xavier, L. B. Thackray, H. W. Virgin, Nondegradative role of Atg5-Atg12/Atg16L1 autophagy protein complex in antiviral activity of interferon gamma. Cell Host Microbe 11, 397-409 (2012); published online Epub April 19 (S1931-3128(12)00094-7 [pii]10.1016/j.chom.2012.03.002).
46. K. Matsunaga, T. Saitoh, K. Tabata, H. Omori, T. Satoh, N. Kurotori, I. Maejima, K. Shirahama-Noda, T. Ichimura, T. Isobe, S. Akira, T. Noda, T. Yoshimori, Two Beclin 1-binding proteins, Atg14L and Rubicon, reciprocally regulate autophagy at different stages. Nature cell biology 11, 385-396 (2009); published online Epub April (10.1038/ncb1846).
47. M. J. Coyne, A. O. Tzianabos, B. C. Mallory, V. J. Carey, D. L. Kasper, L. E. Comstock, Polysaccharide biosynthesis locus required for virulence of *Bacteroides* fragilis. Infection and immunity 69, 4342-4350 (2001); published online Epub July (10.1128/IAI.69.7.4342-4350.2001).
48. S. Patrick, J. H. Reid, Separation of capsulate and non-capsulate *Bacteroides fragilis* on a discontinuous density gradient. Journal of medical microbiology 16, 239-241 (1983); published online Epub May.
49. C. C. Kurtz, I. Drygiannakis, M. Naganuma, S. Feldman, V. Bekiaris, J. Linden, C. F. Ware, P. B. Ernst, Extracellular adenosine regulates colitis through effects on lymphoid and nonlymphoid cells. American journal of physiology. Gastrointestinal and liver physiology 307, G338-346 (2014); published online Epub August 1 (10.1152/ajpgi.00404.2013).
50. J. L. Round, S. M. Lee, J. Li, G. Tran, B. Jabri, T. A. Chatila, S. K. Mazmanian, The Tolllike receptor 2 pathway establishes colonization by a commensal of the human microbiota. Science 332, 974-977 (2011); published online Epub May 20 (science.1206095 [pii] 10.1126/science.1206095).

What is claimed is:

1. A method of screening a test compound, comprising:
   (a) incubating a wild type dendritic cell, an autophagy-related (Atg) gene-mutant dendritic cell, a wild type macrophage, or an Atg gene-mutant macrophage with regulatory T cell ($T_{reg}$) precursors in the presence of at least one test compound or salt thereof;
   (b) detecting a level of $T_{reg}$ cells generated or detecting a level of cytokine secretions; and
   (c) (i) comparing the level of $T_{reg}$ cells generated or cytokine secretions in the Atg gene-mutant dendritic cell in the presence of a test compound to the level of $T_{reg}$ cells generated or cytokine secretions in the in the Atg gene-mutant dendritic cell in the absence of the test compound or (ii) comparing the level of $T_{reg}$ cells generated or cytokine secretions in the Atg gene-mutant dendritic cell in the presence of a test compound to the level of $T_{reg}$ cells generated or cytokine secretions in the in the Atg wild-type dendritic cell in the presence of the test compound; or
   (d) (i) comparing the level of $T_{reg}$ cells generated or cytokine secretions in the Atg gene-mutant macrophage in the presence of a test compound with the level of $T_{reg}$ cells generated or cytokine secretions in the Atg gene-mutant macrophage in the absence of the test compound or (ii) comparing the level of $T_{reg}$ cells generated or cytokine secretions in the Atg gene-mutant macrophage in the presence of a test compound to the level of $T_{reg}$ cells generated or cytokine secretions in the in the Atg wild-type macrophage in the presence of the test compound; and
   (e) determining if the test compound restores $T_{reg}$ generation;
   wherein the test compound may or may not restore $T_{reg}$ generation.

2. The method of claim 1, comprising comparing the level of $T_{reg}$ cells generated in the presence of a test compound to the level of $T_{reg}$ cells generated in the absence of the test compound and selecting a test compound that increased the level of $T_{reg}$ cells generated.

3. The method of claim 1, comprising comparing the level of cytokine secretions in the presence of a test compound to the level of cytokine secretions in the absence of the test compound.

4. The method of claim 1, wherein the Atg gene-mutant is Atg16L1T300A.

5. The method of claim 1, wherein the $T_{reg}$ cell generation is Atg gene-dependent.

6. The method of claim 1, wherein the test compound targets a gene selected from one or more of the group consisting of: Rubicon, Atg16L1, Atg16L1T300A, Atg7, and Atg5.

7. The method of claim 1, wherein the cytokine secretions are IL-10, IL-17A, IL-12, IL-1β, IL-6, or TNFα.

8. The method of claim 1, comprising
incubating wild type dendritic cells; and
comparing the level of $T_{reg}$ cells generated in the Atg gene-mutant dendritic cell to the level of $T_{reg}$ cells generated in the wild type dendritic cells.

9. The method of claim 1, comprising
incubating wild type macrophages; and
comparing the level of $T_{reg}$ cells generated in the Atg gene-mutant macrophage with the level of $T_{reg}$ cells generated in the wild type macrophages.

10. The method of claim 1, wherein the screening comprises small molecule fragment screening.

11. A method of screening a test compound, comprising:
(a) obtaining one or more proteins associated with $T_{reg}$ generation;
(b) incubating the proteins associated with $T_{reg}$ generation in the presence or absence of at least one test compound or salt thereof;
(c) detecting a ligand-protein interaction;
(d) comparing the ligand-protein interaction of the protein in the presence of at least one test compound to the ligand-protein interaction of the protein in the absence of at least one test compound; and
(e) determining if the test compound restores $T_{reg}$ generation;
wherein,
the test compound may or may not restore $T_{reg}$ generation; and
the test compound targets a protein selected from one or more of the group consisting of: RUBICON, ATG16L1, ATG16L1T300A, ATG7, and ATG5.

12. The method of claim 11, wherein the screening comprises small molecule fragment screening.

13. The method of claim 11, wherein the one or more proteins do not comprise ATG16L1 or ATG16L1T300A.

14. The method of claim 11, wherein the one or more proteins are selected from one or more of the group consisting of: RUBICON, ATG7, and ATG5.

* * * * *